United States Patent
Tezcan et al.

(10) Patent No.: US 12,195,620 B2
(45) Date of Patent: Jan. 14, 2025

(54) CONTROLLED ENTRAPMENT AND RELEASE OF MOLECULAR CARGO

(71) Applicant: THE REGENTS OF THE UNIVERSITY OF CALIFORNIA, Oakland, CA (US)

(72) Inventors: Faik Akif Tezcan, La Jolla, CA (US); Ling Zhang, La Jolla, CA (US); Youjeong Na, La Jolla, CA (US); Kenneth Han, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/253,766

(22) PCT Filed: Nov. 19, 2021

(86) PCT No.: PCT/US2021/060221
§ 371 (c)(1),
(2) Date: May 19, 2023

(87) PCT Pub. No.: WO2022/125293
PCT Pub. Date: Jun. 16, 2022

(65) Prior Publication Data
US 2023/0331975 A1 Oct. 19, 2023

Related U.S. Application Data

(60) Provisional application No. 63/116,637, filed on Nov. 20, 2020.

(51) Int. Cl.
*C08L 51/10* (2006.01)
*A61K 9/48* (2006.01)
*A61K 38/47* (2006.01)
*C08F 292/00* (2006.01)

(52) U.S. Cl.
CPC ........... *C08L 51/10* (2013.01); *A61K 9/4833* (2013.01); *A61K 38/47* (2013.01); *C08F 292/00* (2013.01); *C12Y 302/01017* (2013.01); *C08F 2438/03* (2013.01)

(58) Field of Classification Search
None
See application file for complete search history.

(56) References Cited

U.S. PATENT DOCUMENTS

| | | |
|---|---|---|
| 2001/0026946 A1 | 10/2001 | Asher |
| 2004/0018160 A1 | 1/2004 | Hu et al. |
| 2004/0115132 A1 | 6/2004 | Young et al. |
| 2007/0258889 A1 | 11/2007 | Douglas et al. |

FOREIGN PATENT DOCUMENTS

WO 2022/125293 A2 6/2022

OTHER PUBLICATIONS

Han, et al. (J. Am. Chem. Soc. 2022, 144, 10139-10144).*
International Search Report and Written Opinion for International Application No. PCT/US2021/060221, mailed on Jul. 20, 2022, 7 pages.
Zhang, L. et al. "Hyperexpandable, self-healing macromolecular crystals with integrated polymer networks," HHS Public Access, vol. 557, No. 7703, pp. 86-91 (2018).
Abendroth, J. et al., "Controlling Motion at the Nanoscale: Rise of the Molecular Machines," ACS Nano, vol. 9. No. 8, pp. 7768-7768 (2015).
Russell, M. et al., "Trapping and release of cargo molecules from a micro-stamped mesoporous thin film controlled by Poly(NIPAAm-co-AAm)," J Solgel Sci Technol., vol. 70, No. 2, pp. 278-285 (2014).
Burns, J. et al., "A biomimetic DNA-made channel for the ligand-controlled and selective transport of small-molecule cargo through a biological membrane," 1-2, 4, 19. Department of Chemistry, Institute of Structural Molecular Biology, University College London, Web. 2016; p. 16, third paragraph; Figure 4.
Cai, Z. et al., "Photonic crystal protein hydrogel sensor materials enabled by conformationally induced volume phase transition," Chemical Science, Issue 7, pp. 4557-4562 (2016).
Jia, X. et al., "Hybrid Multicomponent Hydrogels for Tissue Engineering," Macomol Biosci., vol. 9, No. 2, pp. 140-156 (2009).
Han, K. et al., "Anisotropic Dynamics and Mechanics of Macromolecular Crystals Containing Lattice-Patterned Polymer Networks," Journal of the American Chemical Society, vol. 142, pp. 19402-19410 (2020).
Abe, S. et al., Encapsulated Protein Containeres by In Vivo Crystal Engineering. Adv. Mater. 2015, 27(48), 7951-7956.
Adams, P. D. et al., Phenix: a comprehensive Python-based system for macromolecular structure solution. *Acta Crystallogr. D* 2010, 66, 213-221.
Akcora, P. et al., Anisotropic self-assembly of spherical polymer-grafted nanoparticles. Nat. Mater. 2009, 8 (4), 354-359.
Alberstein, R. et al., Engineering the entropy-driven free-energy landscape of a dynamic nanoporous protein assembly. Nat. Chem. 2018, 10 (7), 732-739.
Ayala, M. et al., Cross-linked crystals of chloroperoxidase. Biochem. Biophys. Res. Commun. 2002, 295 (4), 828-831.
Barthelat, F. et al., Structure and mechanics of interfaces in biological materials. Nat. Rev. Mater. 2016, 1 (4), 16007.
Basu, S. K. et al., Protein crystals for the delivery of biopharmaceuticals. Expert Opin. Biol. Ther. 2004, 4 (3), 301-317.
Battye, T. G. G. et al., iMOSFLM: a new graphical interface for diffraction-image processing eith MOSFLM. *Acta Crystallogr. D* 2011, 67, 271-281.

(Continued)

*Primary Examiner* — Patricia Duffy
*Assistant Examiner* — Garen Gotfredson
(74) *Attorney, Agent, or Firm* — Perkins Coie LLP

(57) ABSTRACT

Disclosed are reversibly-expandable polymer-integrated crystals (PIX) materials, devices, and methods for controllably encapsulating and releasing molecular cargo. The disclosed PIX materials are engineered crystalline materials with large pores that can entrap macromolecules, such as proteins and nanoparticles. The material expands and contracts reversibly, allowing controlled encapsulation and release of guest/cargo molecules.

30 Claims, 47 Drawing Sheets
Specification includes a Sequence Listing.

(56) References Cited

OTHER PUBLICATIONS

Boyer, C. et al., Bioapplications of RAFT Polymerization. Chem. Rev. 2009, 109 (11), 5402-5436.
Buehler, M. J. et al., Deformation and failure of protein materials in physiologically extreme conditions and disease. Nat. Mater. 2009, 8 (3), 175-188.
Caruso, F. et al., Enzyme encapsulation in layer-by-layer engineered polymer multilayer capsules. Langmuir 2000, 16 (4), 1485-1488.
Chen, J. et al., Artificial musclelike function from hierarchical supramolecular assembly of photoresponsive molecular motors. Nat. Chem. 2018, 10 (2), 132-138.
Chen, Q. et al., A controllable gate effect in cobalt (II) organic frameworks by reversible structure transformations. Angew. Chem., Int. Ed. 2013 52 (44), 11550-11553.
Chen, V. B. et al., MolProbity: all-atom structure validation for macromolecular crystallography. Acta Crystallogr. D 2010, 66, 12-21.
Chen, Y. C. et al., Thermal stability, storage and release of proteins with tailored fit in silica. Sci Rep 2017, 7, 8.
Chiefari, J. et al., Living Free-Radical Polymerization by Reversible Addition-Fragmentation Chain Transfer: The RAFT Process. Macromolecules 1998, 31 (16), 5559-5562.
Chin, S. M. et al., Covalent-supramolecular hybrid polymers as muscle-inspired anisotropic actuators. Nat. Commum. 2018, 9 (1), 2395.
Cobo, I. et al., Smart hybrid materials by conjugation of responsive polymers to biomacromolecules. Nat. Mater. 2015, 14 (2), 143-159.
Commins, P. et al., Efficiently self-healing boronic ester crystals. Chem. Sci. 2020, 11 (10), 2606-2613.
Commins, P. et al., Self-Healing Molecular Crystals. Angew. Chem., Int. Ed. 2016, 55 (42), 13028-13032.
Couck, S. et al., An Amine-Functionalized MIL-53 Metal-Organic Framework with Large Separation Power for CO2 and CH4. J. Am. Chem. Soc. 2009, 131 (18), 6326-6327.
De, P. et al., Temperature—Regulated Activity of Responsive Polymer-Protein Conjugates Prepared by Grafting-from via RAFT Polymerization. J. Am. Chem. Soc. 2008, 130 (34), 11288-11289.
Dutta, S., Exoskeleton for Biofunctionality Protection of Enzymes and Proteins for Intracellular Delivery. Advanced Nanobiomed Research 2020, 2000010.
Emsley, P. et al., Coot: model-building tools for molecular graphics. Acta Crystallogr. Sect. D-Struct. Biol. 2004, 60, 2126-2132.
Erb, R. M. et al., Self-shaping composites with programmable bioinspired microstructures. Nat. Commun. 2013, 4 (1), 1712.
Espinosa, H. D. et al., Merger of structure and material in nacre and bone—Perspectives on de novo biomimetic materials. Prog. Mater. Sci. 2009, 54 (8), 1059-1100.
Evans, P. R. et al., How good are my data and what is the resolution? Acta Crystallogr. D 2013, 69, 1204-1214.
Fernandez-Lafuente, R., Stabilization of multimeric enzymes: Strategies to prevent subunit dissociation Enzyme and Microbial Technology 2009, 45 (6-7), 405-418.
Fratzl, P. et al., Nature's hierachical materials. Prog. Mater. Sci. 2007, 52 (8), 1263-1334.
Ghosh, S. et al., Elastic and Bendable Caffeine Cocrystals: Implications for the Design of Flexible Organic Materials. Angew., Chem., Int. Ed. 2012, 51 (41), 10319-10323.
Goddard, T. D. et al.; UCSF ChimeraX: Meeting modern challenges in visualization and analysis. Prot. Sci. 2018, 27 (1), 14-25.
Han, Y. J. et al., Mesoporous silicate sequestration and release of proteins. J. Am. Chem. Soc. 1999, 121 (42), 9897-9898.
Hanefeld, U. et al., Understanding enzyme immobolisation. Chem. Soc. Rev. 2009, 38 (2), 453-468.
Hashimoto, T. et al., Encapsulation of biomacromolecules by soaking and co-crystallization into porous protein crystals of hemocyanin. Biochem. Biophys. Res. Commun. 2019, 509 (2), 577-584.
Heater, B. et al., In Vivo Enzyme Entrapment in a Protein Crystal. J. Am. Chem. Soc. 2020, 142 (22), 9879-9883.

Horike, S. et al. Soft porous crystals. Nat. Chem. 2009, 1 (9), 695-704.
Huang, S. M. et al., "Armor-Plating" Enzymes with Metal-Organic Frameworks (MOFs). Angew. Chem.-Int. Edit. 2020, 59 (23), 8786-8798.
Huard, D. J. et al., Re-engineering protein interfaces yields copper-inducible ferritin cage assembly. Nat. Chem. Biol. 2013, 9 (3), 169-76.
Hudson, S. et al., Proteins in Mesoporoous Silicates. Angew. Chem.-Int. Edit. 2008, 47 (45), 8582-8594.
Huo, J. et al., Magnetic MOF microreactors for recyclable size-selective biocatalysis. Chem. Sci. 2015, 6 (3), 1938-1943.
Iwaso, K. et al., Fast response dry-type artificial molecular muscles with [c2]daisy chains. Nat. Chem. 2016, 8 (6), 625-632.
Jeon, S.-J. et al., Shape-Morphing Materials from Stimuli-Responsive Hydrogel Hybrids. Acc. Chem. Res. 2017, 50 (2), 161-169.
Jia, Z. F. et al., Multifunctional Nanoworks and Nanorods through a One-Step Aqueous Dispersion Polymerization. J. Am. Chem. Soc. 2014, 136 (16), 5824-5827.
Jiang, S. et al., Unusual and Superfast Temperature-Triggered Actuators. Adv. Mater. 2015, 27 (33), 4865-4870.
Karothu, D. P. et al., Global Performance Indices for Dynamic Crystals as Organic Thermal Actuators. Adv. Mater., 1906216.
Ke, N. et al., Visualization of Periplasmic and Cytoplasmic Proteins with a Self-Labeling Protein Tag. J. Bacteriol. 2016, 198 (7), 1035-1043.
Keller, O. et al., Preparation and Some Properties of Maleimido Acids and Maleoyl Derivatives of Peptides. Helv. Chim. Acta 1975, 58 (2), 531-541.
Kirkman, H. N. et al., Catalase—A Tetrameric Enzyme with 4 Tightly Bound Molecules of NADPH. Proceedings of the National Academy of Sciences of the United States of America-Biological Sciences 1984. 81 (14), 4343-4347.
Kobatake, S. et al., Rapid and reversible shape changes of molecular crystals on photoirradiation. Nature 2007, 446 (7137), 778-781.
Kushner, A. M. et al., Modular Design in Natural and Biomimetic Soft Materials. Angew. Chem., Int. Ed. 2011, 50 (39), 9026-9057.
Laothanachareon, T. et al., Cross-linked enzyme crystals of organophosphate hydrolase for electrochemical detection of organophosphorus compounds. World J. Microbiol. Biotechnol. 2008, 24 (12), 3049-3055.
Lawson, D. M. et al., Solving the structure of human H ferritin by genetically engineering intermolecular crystal contacts. Nature 1991, 349 (6309), 541-4.
Li, M. M. et al., Fabricating Covalent Organic Framework Capsules with Commodious Microenvironment for Enzymes. J. Am. Chem. Soc. 2020, 142 (142) (14), 6675-6681.
Liang, K. et al., Biomimetic mineralization of metal-organic framework as protective coatings for biomacromolecules. Nat. Commum. 2015, 6, 8.
Lin, J. L. et al., Water-Soluble Flexible Organic Frameworks That Include and Deliver Proteins. J. Am. Chem. Soc. 2020, 142 (7), 3577-3582.
Liu, M. et al., An anisotrpic hydrogel with electrostatic repulsion between cofacially aligned nanosheets. Natue 2015, 517 (7532), 68-72.
Lu, C. et al., Stimuli-responsive polymer non-science: Shape anisotropy, responsiveness, applications. Prog. Polym. Sci. 2018, 78, 24-46.
Ma, Y. et al., Nanoclustered Cascaded Enzymes for Targeted Tumor Starvation and Deoxygenation-Activated Chemotherapy without Systemic Toxicity. ACS Nano 2019, 13 (8), 8890-8902.
Majewski, M. B. et al., Enzyme encapsulation in metal-organic frameworks for applications in catalysis. Crystengcomm 2017, 19 (29), 4082-4091.
Margolin, A. L. et al., Protein crystals as novel catalytic materials. Angew. Chem.-Int. Edit 2001, 40 (12), 2204-2222.
Mason, J. A. et al., Methane storage in flexible metalorganic frameworks with intrinsic thermal management. Nature 2015, 527 (7578), 357-361.
Mccoy, A. J. et al., Phaser crystallographic software. J. Appl. Crystallogr. 2007, 40, 658-674.

(56) References Cited

OTHER PUBLICATIONS

McKinlay, A. C. et al., Nitric Oxide Adsorption and Delivery in Flexible MIL-88(Fe) Metal-Organic Frrameworks. Chem. Mater. 2013, 25 (9), 1592-1599.

Mehta, J. et al., Recent advances in enzyme immobilization techniques: Metal-organic frameworks as novel substrates. Coord. Chem. Rev. 2016, 322, 30-40.

Naumov, P. et al., Mechanically Responsive Molecular Crystals. Chem. Rev. 2015, 2015, 115 (22), 12440-12490.

Olshansky, L. et al., Artificial Metalloproteins Containing Co4O4 Cubane Active Sites. J. Am. Chem. Soc. 2018, 140 (8), 2739-2742.

Panda, M. K. et al., Spatially resolved analysis of shortrange structure perturbations in a plastically bent molecular crystal. Nat. Chem. 2015, 7 (1), 65-72.

Pang, J. et al., Solvent-Assisted, Thermally Triggered Structural Transformation in Flexible Mesoporous Metal-Organic Frameworks. Chem. Mater. 2019, 31 (21), 8787-8793.

Panganiban, B. et al., Random heteropolymers preserve protein function in foreign environments, Science 2018, 359 (6381), 1239-1243.

Park, N. et al., Hydrogel-Based Artificial Muscles: Overview and Recent Progress. Adv. Intell. Sys. 2020, 2 (4), 1900135.

The PyMOL Molecular Graphics System Version 1.3 https://pymol.org/2/support.html (Schrodinger LLC); web page visited Sep. 9, 2024.

Qiao, L. et al., A nanoporous reactor for efficient proteolysis. Chem.-Eur. J. 2008, 14 (1), 151-157.

Qin, H. et al., Anistrophic and self-healing hydrogels with multiresponsive actuating capability. Nat. Commun. 2019, 10 (1), 2202.

Renggli, K. et al., Selective and Responsive Nanoreactors. Adv. Funct. Mater. 2011, 21 (7), 1241-1259.

Roy, J. J. et al., Biosensor for the determination of phenols based on Cross-Linked Enzyme Crystals (CLEC) of laccase. Biosens. Bioelectron. 2005, 21 (1), 206-211.

Sano, K. et al., Synthesis of Anisotropic Hydrogels and Their Applications. Angew. Chem., Int. Ed. 2018, 57 (10), 2532-2543.

Sato, H. et al., Self-Accelerating CO Sorption in a Soft Nanoporous Crystal. Science 2014, 343 (6167), 167-170.

Sato, O., Dynamic molecular crystals with switchable physical properties. Nat. Chem. 2016, 8 (7), 644-656.

Schmid, A. et al., Industrial biocatalysis today and tomorrow. Nature 2001, 409 (6817), 258-268.

Schneemann, A. et al., Flexible metal-organic frameworks. Chem. Soc. Rev. 2014, 43 (16), 6062-6096.

Seeman, N. C. et al., Emulating biology: Building nanostructures from the bottom up. Proc. Natl. Acad. Sci. U. S. A. 2002, 99, 6451-6455.

Serre, C. et al., Role of Solvent-Host Interactions That Lead to Very Large Swelling of Hybrid Frameworks. Science 2007, 315 (5820), 1828-1831.

Sheldon, R. A. et al., Enzyme immobilisation in biocatalysis: why, what and how. Chem. Soc. Rev. 2013, 42 (15), 6223-6235.

Sheldon, R. A., Enzyme immobilization: The quest for optimum performance. Adv. Synth. Catal. 2007, 349 (8-9), 1289-1307.

Shen, S. H. et al., High drug-loading nanomedicines: progress, current status, and prospects. Int. J. Nanomed. 2017, 12 4085-4109.

Shieh, F.-K. et al., Imparting Functionality to Biocatalysts via Embedding Enzymes into Nanoporous Materials by a de Novo Approach: Size-Selective Sheltering of Catalase in Metal-Organic Framework Microcrystals. J. Am. Chem. Soc. 2015, 137 (13), 4276-4279.

Slowing, II et al., Mesoporous silica nanoparticles for intracellular delivery of membrane-impermeable proteins. J. Am. Chem. Soc. 2007, 129 (28), 8845-8849.

Sontz, P. A. et al., A Metal Organic Framework with Spherical Protein Nodes: Rational Chemical Design of 3D Protein Crystals. *J. Am. Chem. Soc.* 2015, 137 (36), 11598-11601.

Su, C. K. et al., Partitioning and purification of lysozyme from chicken egg white usng acqueous two-phase system. Process Biochem. 2006, 41 (2), 257-263.

Suzuki, Y. et al., Self-assembly of coherently dynamic, auxetic, twodimensional protein crystals. Nature 2016, 533 (7603), 369-373.

Takashima, Y. et al., Molecular decoding using luminescence from an entangled porous framework. Nat. Commun. 2011. 2 (1), 168.

Theil, E. C., Ferritin: structure, gene regulation, and cellular function in animals, plants and microorganisms. Annu. Rev. Biochem. 1987, 56 (1), 289-315.

Uehara, T. et al., Ga-67/68-Labeling Agent That Liberates Ga-67/68-NOTA-Methionine by Lysosomal Proteolysis of Parental Law Molecular Weight Polypeptide to Reduce Renal Radioactivity Levels. *Bioconj. Chem.* 2014, 25 (11), 2038-2045.

Volodkin, D. V. et al., Protein encapsulation via porous CaCO3 microparticles templating. Biomacromolecules 2004, 5 (5), 1962-1972.

Wang, H. R. et al., Protein-Structure-Directed Metal-Organic Zeolite-like Networks as Biomacromolecule Carriers. Angew. Chem.-Int. Edit. 2020, 59 (15), 6263-6267.

Wei, T. H. et al., Rapid mechanochemical encapsulation of biocatalysts into robust metal-organic frameworks. Nat. Commun. 2019, 10, 8.

Wei, Y.-S. et al., Turning on the flexibility of isoreticular porous coordination frameworks for drastically tunable framework breathing and thermal expansion. Chem. Sci. 2013, 4 (4), 1539-1546.

Worthy A. et al., Atomic resolution of structural changes in elastic crystals of copper (II) acetylacetonate. Nat. Chem. 2018, 10, 65-69.

Yang, X. Y. et al., "Fish-in-Net" Encapsulation of Enzymes in Macroporous Cages for Stable, Reusable, and Active Heterogeneous Biocatalysts. Adv. Mater. 2006, 18 (4), 410-414.

Ye, C. et al., A review of recent progress in drug and protein encapsulation: Approaches, applications and challenges. Mater. Sci. Eng. C-Mater. Biol. Appl. 2018, 83, 233-246.

Yijing Chen, F.J.-A. et al., Insights into the Enhanced Catalytic Activity of Cytochrome c When Encapsulated in a Metal—Organic Framework. J. Am. Chem. Soc. 2020, 142 (43).

Yu, J. et al., Preparation of two dimensional layererd double hydroxide nanosheets and their applications. Chem. Soc. Rev. 2017, 46 (19), 5950-5974.

Yu, Y. et al., Directed bending of a polymer film by light. Nature 2003, 425 (6954), 145-145.

Zhang, Y. S. et al., Advances in engineering hydrogels. Science 2017, 356 (6337), No. eaaf3627.

\* cited by examiner

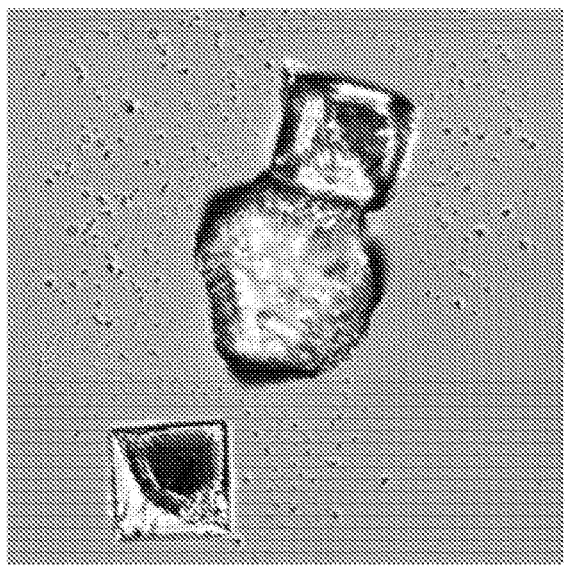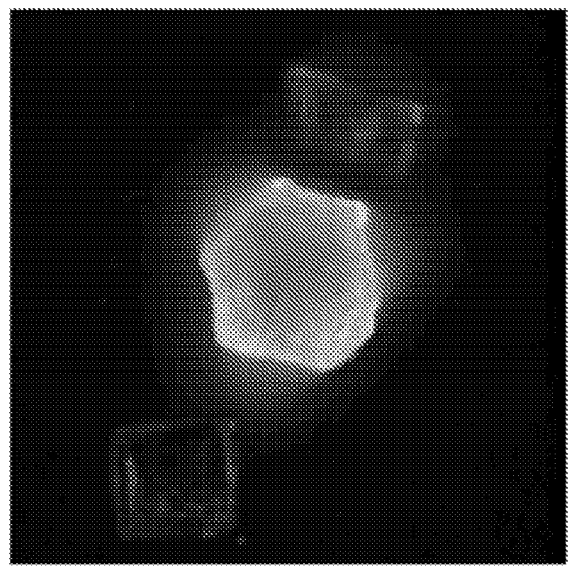
FIG. 9

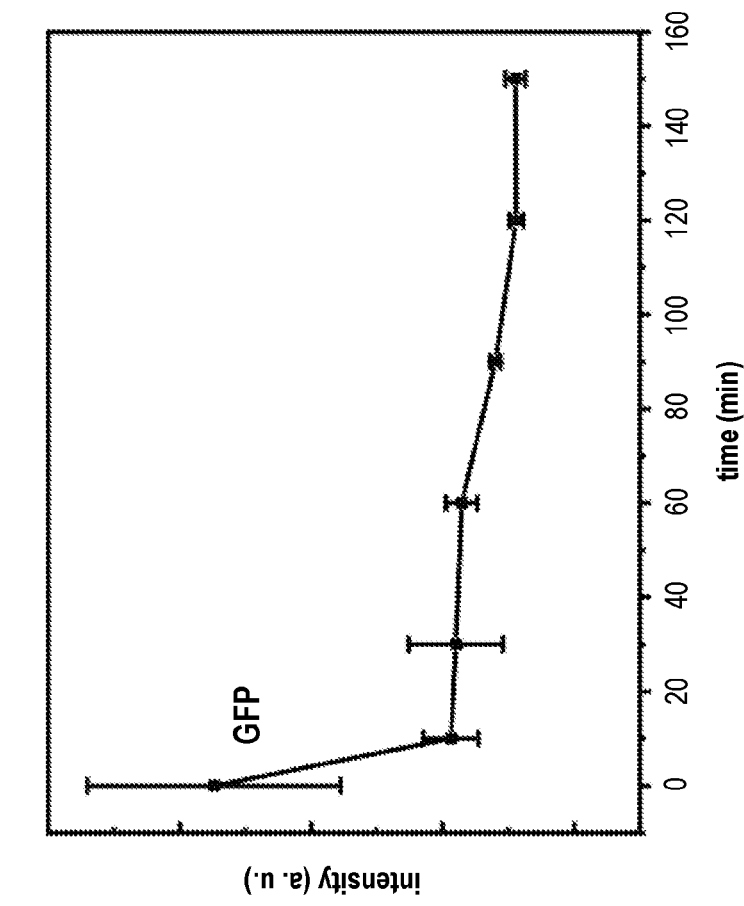
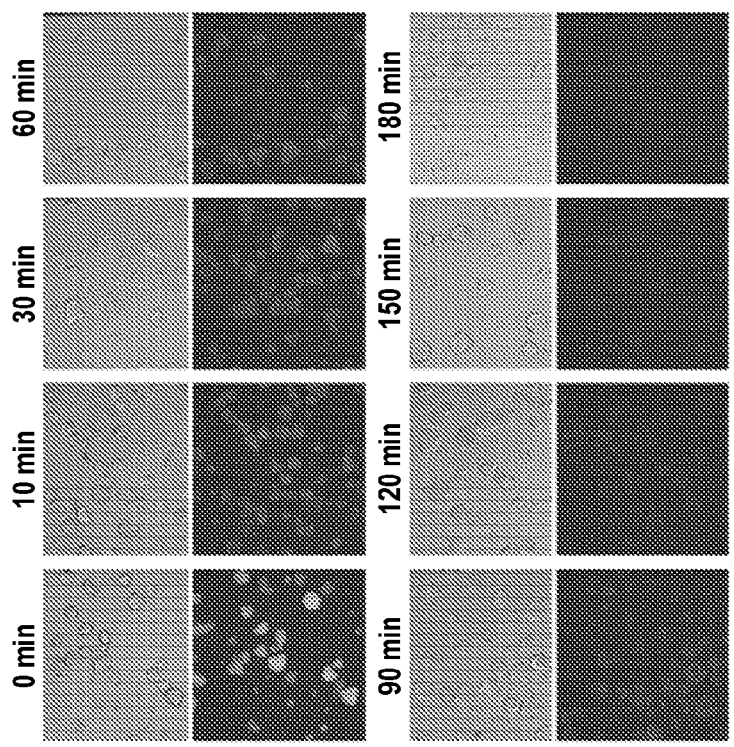
FIG. 10

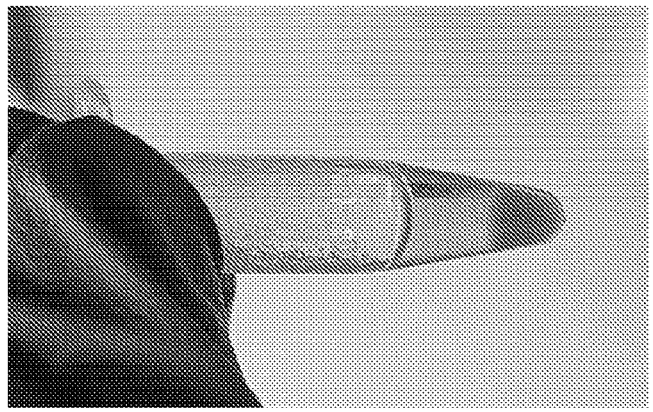
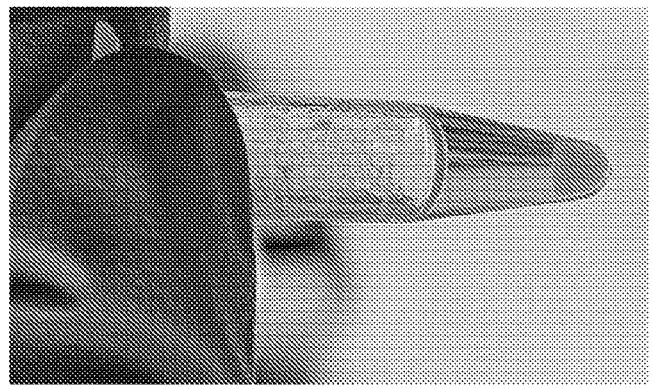
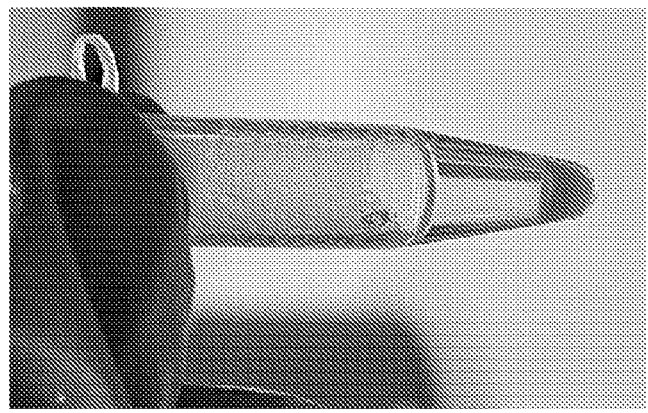
pH 6 – uptake
pH 3 – release
pH 6 – uptake
FIG. 13

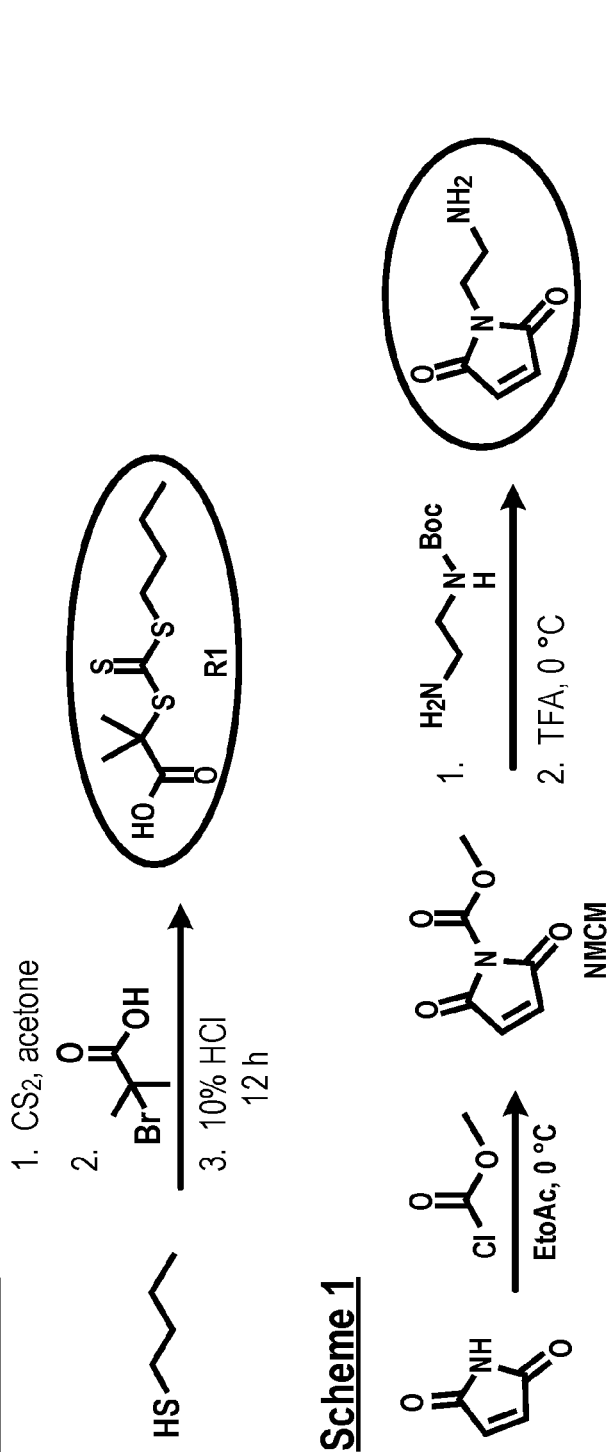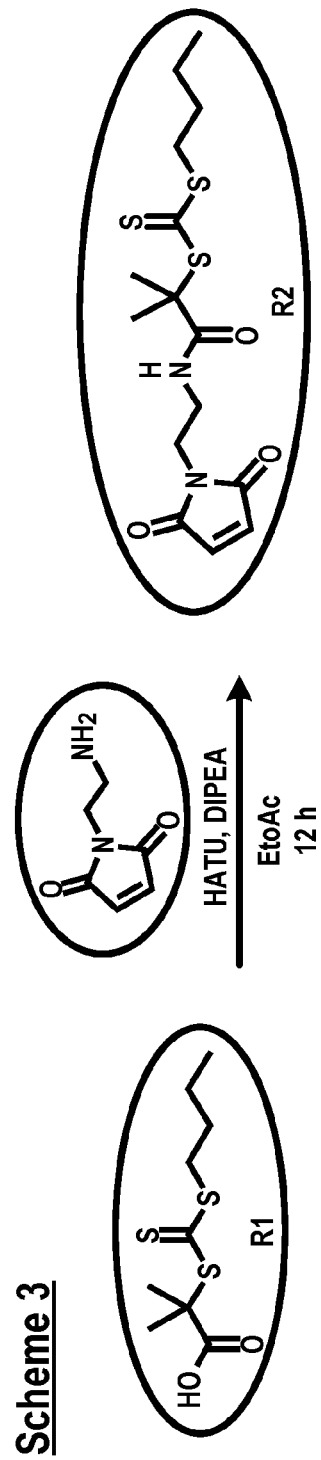
FIG. 25

Table 2. Self-assembly conditions for: (1) cubic (F432) and rhombohedral (H32) $^{RAFT}$ferritin crystals and (2) trigonal (P3121) and cubic (F432) $^{\Delta C}$ferritin crystals.

| | | |
|---|---|---|
| F432 $^{RAFT}$ferritin | Stock protein solution | 25 µM in 15 mM HEPES (pH 7.0) |
| | Reservoir | 500 µL total volume: 25 mM HEPES (pH 8.0), 10 mM CaCl₂, 140 mM NaCl |
| | Sitting drop | 5 µL reservoir, 5 µL of 25 µM $^{RAFT}$ferritin |
| H32 $^{RAFT}$ferritin | Stock protein solution | 25 µM in 15 mM HEPES (pH 7.0) |
| | Reservoir | 500 µL total volume: 50 mM MES (pH 6.5), 6 mM CaCl₂ |
| | Sitting drop | 5 µL reservoir, 5 µL of 25 µM $^{RAFT}$ferritin |
| P3121 $^{\Delta C}$ferritin | Stock protein solution | 25 µM in 50 mM Tris (pH 7.5), 1 M NaCl |
| | Reservoir | 525 µL total volume: 100 µL of 500 mM HEPES (pH 7.0), 125 µL of 1 M NH4OAc, 300 µL 2-Methyl-2,4-pentanediol |
| | Sitting drop | 5 µL reservoir, 5 µL of 25 µM $^{\Delta C}$ferritin |
| F432 $^{\Delta C}$ferritin | Stock protein solution | 25 µM in 150 mM Tris (pH 7.4), 150 mM NaCl |
| | Reservoir | 500 µL total volume: 50 mM HEPES (pH 7.0), 12 mM CaCl₂ |
| | Sitting drop | 5 µL reservoir, 5 µL of 25 µM $^{\Delta C}$ferritin |

FIG. 26

2800 providing, in an environment containing molecules of a molecular cargo, a reversibly-expandable polymer-integrated crystal (PIX) material, comprising: a crystal comprising a plurality of protein molecules organized in a crystal lattice; and a polymer matrix formed within the crystal lattice of the crystal such that the polymer matrix encompasses molecules from the plurality of protein molecules
2810 triggering an expansion of the PIX material by applying a first stimulus to the environment to cause the crystal lattice of the PIX material to expand
2820 loading the molecules of the molecular cargo within the expanded crystal lattice of the PIX material
2830 entrapping the molecular cargo within the PIX material by triggering a contraction of the PIX material by applying a second stimulus to the environment to cause the crystal lattice of the PIX material to contract with the loaded molecules of the molecular cargo contained within the crystal lattice
2840

```
providing, in an environment containing charged molecules of the molecular cargo, a
polymer-integrated crystal (PIX) material, comprising: a crystal comprising a plurality
of protein molecules organized in a crystal lattice; and a polymer matrix formed within
the crystal lattice of the crystal such that the polymer matrix encompasses molecules
from the plurality of protein molecules
2910
```

↓

```
keeping the PIX material in the environment for an amount of time without expanding
the crystal lattice of the crystal of the PIX material
2920
```

↓

```
removing, without expanding the crystal lattice of the crystal of the PIX material, the
PIX material from the environment immediately after said keeping the PIX material in
the environment for the amount of time
2930
```

FIG. 29

CONTROLLED ENTRAPMENT AND RELEASE OF MOLECULAR CARGO

RELATED APPLICATIONS

This patent document is a U.S.C § 371 National Stage of International Application No. PCT/US2021/060221 titled "CONTROLLED ENTRAPMENT AND RELEASE OF MOLECULAR CARGO" and filed on Nov. 19, 2021, which claims priority to and benefits of U.S. Provisional Patent Application No. 63/116,637 entitled "CONTROLLED ENTRAPMENT AND RELEASE OF MOLECULAR CARGO" and filed on November 20, 2020. The entire contents of the before-mentioned patent applications are incorporated by reference as part of the disclosure of this patent document.

STATEMENT REGARDING FEDERALLY SPONSORED RESEARCH OR DEVELOPMENT

This invention was made with government support under W911NF-19-1-0228 awarded by the Department of ARMY Research aka Army Research Office and under DE-SC0003844 awarded by the Department of Energy (DOE). The U.S. government has certain rights in the invention.

REFERENCE TO SEQUENCE LISTING SUBMITTED VIA EFS-WEB

This application includes an electronically submitted sequence listing in .txt format. The .txt file contains a sequence listing entitled "009062-8444. WO00 ST25.txt" created on Jun. 16, 2022 and is 735 bytes in size. The sequence listing contained in the .txt file is part of the specification and is hereby incorporated by reference herein in its entirety.

TECHNICAL FIELD

This patent document relates to materials for entrapment and release of molecules.

BACKGROUND

Crystalline materials are often stiff and brittle, and polymer-based soft materials often have little molecular structure, each being unsuitable for many applications, particularly for the controlled encapsulation and release of biomolecules. As such, new materials would help bridge the gap between crystalline materials and flexible materials to enable new functionalities such as controlled encapsulation and release of biomolecules.

SUMMARY

The techniques disclosed herein can be implemented in various embodiments to provide reversibly-expandable polymer-integrated crystal (PIX) materials, devices, and methods for controllably encapsulating and releasing molecular cargo.

An aspect of the disclosed embodiments relates to a reversibly-expandable polymer-integrated crystal (PIX) material for controllably entrapping and releasing a molecular cargo that includes a crystal comprising a plurality of protein molecules organized in a crystal lattice and a polymer matrix formed within the crystal lattice of the crystal such that the polymer matrix encompasses molecules from the plurality of protein molecules. In the PIX material, the polymer matrix is configured to cause the crystal lattice to expand in response to a first stimulus and configured to cause the crystal lattice to contract, when the crystal lattice is expanded, in response to a second stimulus which is different from the first stimulus. Furthermore, the PIX material is operable to capture the molecular cargo by loading the molecules of the molecular cargo within the crystal lattice of the PIX material when the crystal lattice is expanded and is operable to entrap the molecules of the molecular cargo within the PIX material by contracting the crystal lattice with the loaded molecules of the molecular cargo contained within the crystal lattice. The PIX material is also operable to release the molecules of the molecular cargo which includes re-expanding the crystal lattice after entrapment of the molecules of the molecular cargo within the PIX material.

Another aspect of the disclosed embodiments relates to a method of controllably entrapping a molecular cargo within a material that includes providing, in an environment containing molecules of the molecular cargo, a reversibly-expandable polymer-integrated crystal (PIX) material that includes a crystal comprising a plurality of protein molecules organized in a crystal lattice and a polymer matrix formed within the crystal lattice of the crystal such that the polymer matrix encompasses molecules from the plurality of protein molecules. The method further includes triggering an expansion of the PIX material by applying a first stimulus to the environment to cause the crystal lattice of the PIX material to expand. The method also includes loading the molecules of the molecular cargo within the expanded crystal lattice of the PIX material. Furthermore, the method includes entrapping the molecular cargo within the PIX material by triggering a contraction of the PIX material by applying a second stimulus to the environment to cause the crystal lattice of the PIX material to contract with the loaded molecules of the molecular cargo contained within the crystal lattice.

Yet another aspect of the disclosed embodiments relates to a method of controllably entrapping a charged molecular cargo in a material that includes providing, in an environment containing charged molecules of the molecular cargo, a reversibly-expandable polymer-integrated crystal (PIX) material that includes a crystal comprising a plurality of protein molecules organized in a crystal lattice and a polymer matrix formed within the crystal lattice of the crystal such that the polymer matrix encompasses molecules from the plurality of protein molecules. In the method, each molecule from the charged molecules has a first electric charge and the polymer matrix of the PIX material has a second electric charge having a sign opposite to a sign of the first electric charge. The method further includes keeping the PIX material in the environment for an amount of time without expanding the crystal lattice of the crystal of the PIX material. The method also includes removing, without expanding the crystal lattice of the crystal of the PIX material, the PIX material from the environment immediately after said keeping the PIX material in the environment for the amount of time.

BRIEF DESCRIPTION OF THE DRAWINGS

FIG. 9 shows image data from an example implementation of the disclosed PIX materials demonstrating encapsulation of an inorganic nanoparticle within an example PIX material.

FIG. 10 shows image data and a data plot depicting example results from an example implementation demonstrating controlled release of cargo molecules from an example PIX material.

FIG. 13 illustrates a cycle of pH-dependent protein uptake, release and re-uptake by an example embodiment of a PIX material according to the disclosed technology.

FIG. 25 shows a schematic representation of the synthesis of RAFT agent (R2).

FIG. 26 shows example self-assembly conditions for different ferritin crystals according to the disclosed technology.

FIG. 28 shows a flow diagram of an example embodiment of a method of controllably entrapping a molecular cargo within a material according to the disclosed technology.

FIG. 29 shows a flow diagram of an example embodiment of a method of controllably entrapping a charged molecular cargo in a material according to the disclosed technology.

DETAILED DESCRIPTION

Figure 1:
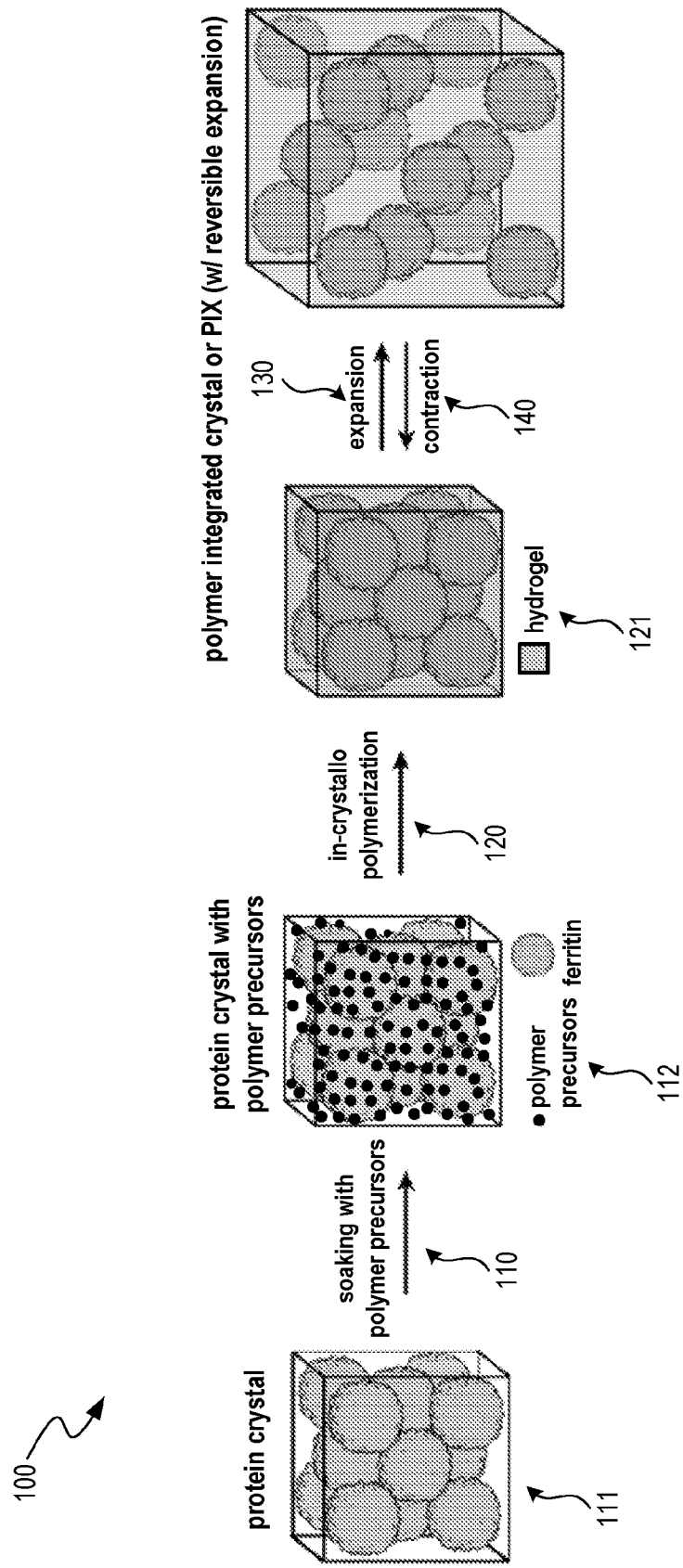
FIG. 1 shows a diagram illustrating formation of a reversibly-expandable polymer-integrated crystal (PIX) material in accordance with the present disclosure.

The techniques disclosed herein overcome the shortcomings of prior technology and can be implemented in various embodiments to provide materials which combine the stability and order of crystalline materials with the flexibility and responsiveness of polymer-based (also referred to as "soft") materials. Methods and system according to the present disclosure allow performing controlled encapsulation and release of cargo molecules and/or particles (e.g., nanoparticles) via reversible expansion and contraction of polymer-integrated crystal (PIX) materials disclosed herein.

Current methods to entrap/release cargo (such as, e.g., proteins) generally involve the use of either amorphous polymer systems or rigid, crystalline constructs, such as metal-organic frameworks (MOFs) or porous inorganic particles. Polymer systems can display dynamic properties by expanding and contracting. However, due to their intrinsically amorphous network, polymeric materials may suffer from unintentional passive leaching of the cargo, difficulty in controlling release of the cargo, and difficulty in maintaining their structural integrity.

On the other end of the spectrum, MOFs and porous inorganic particles such as, e.g., vaterite, silica or iron oxide crystals are examples of rigid materials with defined pore sizes. However, the required molecular interconnectivity thwarts MOFs and porous inorganic particles from being dynamic (i.e., from expanding and contracting on demand or at all). The MOF material's pore size dictates which biomolecules can be entrapped in it and limits the type of proteins available for entrapment. Generally, this method requires passive diffusion of proteins into the material. Another approach involves de novo encapsulation where the protein is included in the MOF precursor mixture. Upon incubation, the MOF forms and the proteins are trapped inside the MOF material. However, this limits the types of MOFs available to use, due to the protein requiring compatible conditions-extreme conditions will denature the protein cargo.

Disclosed herein are reversibly-expandable polymer-integrated crystal (PIX) materials, devices, and methods for controllably encapsulating and releasing molecular cargo. The reversibly-expandable nature of the disclosed materials means that they can change (e.g., increase) their size (e.g., along one or more dimensions) and then revert to their original size which they had prior to the size change. The disclosed PIX materials are engineered crystalline materials with large pores that can entrap macromolecules, such as proteins and nanoparticles. The material can expand and contract reversibly, allowing controlled encapsulation and release of cargo molecules (also referred to as guest molecules). The disclosed PIX materials combine the stability and order of crystalline materials with the flexibility and responsiveness of polymer-based soft materials.

Importantly, there are no other biological materials that combine the simultaneous crystallinity, flexibility, stimuli-responsiveness and modularity of PIX. Implementations of the disclosed materials, devices, and methods can include one or more of the following features in various implementations described in this patent document. For example, the disclosed materials, devices, and methods can provide controlled loading and release of pharmaceutical and/or diagnostic agents, stable and/or cold-chain-free preservation of biologics, sensing of various analytes, biocatalysis of different molecular species, and/or sequestration of toxic molecules and can be used as stimuli-responsive delivery systems. The polymer-integrated crystal (PIX) materials which include polymer-integrated crystals according to the present disclosure seamlessly combine the structural order and periodicity of crystals with the adaptive and tunable mechanical properties of polymeric networks.

A PIX material according to an example embodiment may include a single polymer-integrated crystal or a plurality of polymer-integrated crystals which, like grains of sand, can be aggregated together but, at the same time, not necessarily strongly bound to each other. In some example embodiments, polymer-integrated crystals of the PIX material may be put or embedded into a matrix (e.g., a solid or a liquid one). In this patent document, the processes of expansion and contraction of a PIX material include expansion or contraction of at least one polymer-integrated crystal of the material, respectively.

The disclosed PIX materials can capture and release molecular cargo such as, e.g., organic and/or non-organic molecules in a wide range of molecular weights (e.g., from small organic molecules to proteins or deoxyribonucleic acid (DNA) and/or ribonucleic acid (RNA) molecules), or nanoparticles. These PIX materials have several unique properties, including but not limited to, the following. The pore size of the polymer-integrated crystal is not a limitation on what size cargo it can capture because the PIX material can expand and contract. The reversible expandability and contractibility allows active and/or externally-controllable and/or stimuli-responsive capture and release of cargo (e.g., molecules or nanoparticles). The polymeric network in a PIX material can be changed or modified with specific functional groups, thus allowing more selective binding of different molecules of interest (e.g., proteins) to the polymeric network of the PIX material. The polymer component of a PIX material can be changed or modified (e.g., chemically) to change efficiencies and/or kinetics of the encapsulation and/or release of different molecular species by the PIX material. In an example implementation of a PIX material according to the present disclosure, the protein crystals may be composed of human heavy chain ferritin. This is a non-immunogenic protein, which itself can be used for targeting of certain tissues or cancer cells and can be used to store cargo (e.g., a therapeutic agent) in its interior. Ferritin can be modified genetically and/or chemically to alter its interactions with the polymer matrix in a PIX material, thus providing additional means to change the PIX encapsulation and/or release efficiencies and/or kinetics. In addition, PIX materials may be made using protein crystals made using proteins other than ferritin, which in turn would allow other protein-based functions to be exploited, the PIX encapsulation and/or release properties to be further modulated, and further increase the scope of cargo molecules to be encapsulated in the PIX materials.

FIG. 1 shows a diagram illustrating a method 100 of formation of a reversibly-expandable polymer-integrated crystal (PIX) material in accordance with the present technology. The method 100 includes a process 110 of soaking macromolecular (e.g., protein) crystals (e.g., ferritin crystals such as a crystal 111 shown in FIG. 1) with polymer precursors (e.g., acrylic acid, acrylamide) such that the polymer precursors are infused into the macromolecular crystal lattice of the macromolecular crystal. In some example embodiments, the macromolecular crystal lattice may include amino acids, deoxyribonucleic acid (DNA), or ribonucleic acid (RNA). For example, the crystal lattice may be configured as a face centered cubic (fcc) structure or another crystal structure. The fcc structure may be characterized by a mesoporous network including cube-shaped chambers that are interconnected by octahedron shaped cavities in some example embodiments. FIG. 1 shows a protein crystal 112 which includes (e.g., permeated with) with polymer precursors. The method 100 further includes a process 120 of polymerizing the polymer precursors within the macromolecular (e.g., protein) crystals to form a polymer material (e.g., a hydrogel) matrix around the macromolecules (e.g., protein molecules) in the lattice of the crystal. As, for example, the poly(acrylate-acrylamide) copolymer hydrogel forms, it integrates into void spaces in the protein crystal. FIG. 1 shows a polymer-integrated crystal (PIX) 121 which includes a hydrogel matrix formed from the polymer precursors around the protein molecules in the lattice of the protein crystal. For example, the hydrogel matrix may include poly(acrylate-acrylamide). A polymer-integrated crystal (PIX) material which includes polymer-integrated crystals such as the crystal 121 shown in FIG. 1 can undergo a process 130 of reversible expansion (e.g., by up to 600 percent in volume or more in some example embodiments) followed by a process 140 of reversible contraction without losing crystallinity, such that, e.g., each time the PIX material contracts, the crystal lattice of the crystals in the material reforms. In some example embodiments, the process 140 may be accompanied by a process of self-healing of the polymer-integrated crystals of the PIX material.

In an example embodiment, the process 130 of reversible expansion of a polymer-integrated crystal (PIX) material according to the present disclosure may include exposing the PIX material to water, wherein the water causes a breaking of bonds of the protein crystal with an expansion of the polymer material component of the PIX material due to water absorption. According to an example embodiment, the process 140 of reversible contraction a polymer-integrated crystal (PIX) material according to the present disclosure may include exposing the PIX material to a sodium chloride solution, wherein the sodium chloride solution causes a contraction of the polymer material component of the PIX material due to the removal of water from the polymer material. Reversible expansion and contraction of a PIX material may be used to store large biological agents like, e.g., antibodies or nucleic or ribonucleic acids within the material, and then to release them in desired locations in the body for therapeutic purposes. Reversible expansion and contraction (also referred to as swelling-deswelling behavior) of a PIX material according to the disclosed technology can be modulated or controlled by external stimuli including but not limited to change of ionic strength or change in pH of the environment (e.g., a fluid) containing the PIX material, or other stimuli, according to some example embodiments.

A PIX material according to an example embodiment includes macromolecular ferritin crystals with integrated hydrogel polymers which can isotropically expand their original dimensions and their original volume while retaining periodic order and faceted Wulff morphologies. For example, in some example embodiments, macromolecular ferritin crystals with integrated hydrogel polymers may expand to 180% of their original dimensions and >500% of their original volume. After the separation of neighboring ferritin molecules by, for example, 50 Å upon lattice expansion, specific molecular contacts between them can be reformed upon lattice contraction, resulting in the recovery of atomic-level periodicity. Dynamic bonding interactions between the hydrogel network and the ferritin molecules endow the crystals with the ability to resist fragmentation and self-heal efficiently, while the chemical tailorability of the ferritin molecules enables the creation of chemically and mechanically differentiated domains within single crystals.

In some example embodiments, the polymer (e.g., hydrogel)-expandable polymer-integrated molecular crystals according to the present disclosure, may have one or more of the following properties: 1) mesoporous lattices to enable the polymer (e.g., hydrogel) network to penetrate efficiently and, e.g., uniformly into the crystals; 2) intermolecular interactions between the constituents of the lattices that are reversible and chemically specific (i.e., contain directional and dynamic bonds), such that they disengage with case during expansion and re-engage with high fidelity upon contraction; 3) interactions between the constituents of the lattice and the polymer (e.g., hydrogel) network that are extensive that maintain the integrity of the crystal-polymer hybrid and sufficiently dynamic to minimize the build-up of local strain and to enable self-healing.

The integration of two macromolecular crystal and polymer components in a PIX material circumvents the fundamental limitation that ordered substances (e.g., crystals) are brittle and inflexible, and flexible materials (e.g., polymers) are devoid of order.

Figure 2:
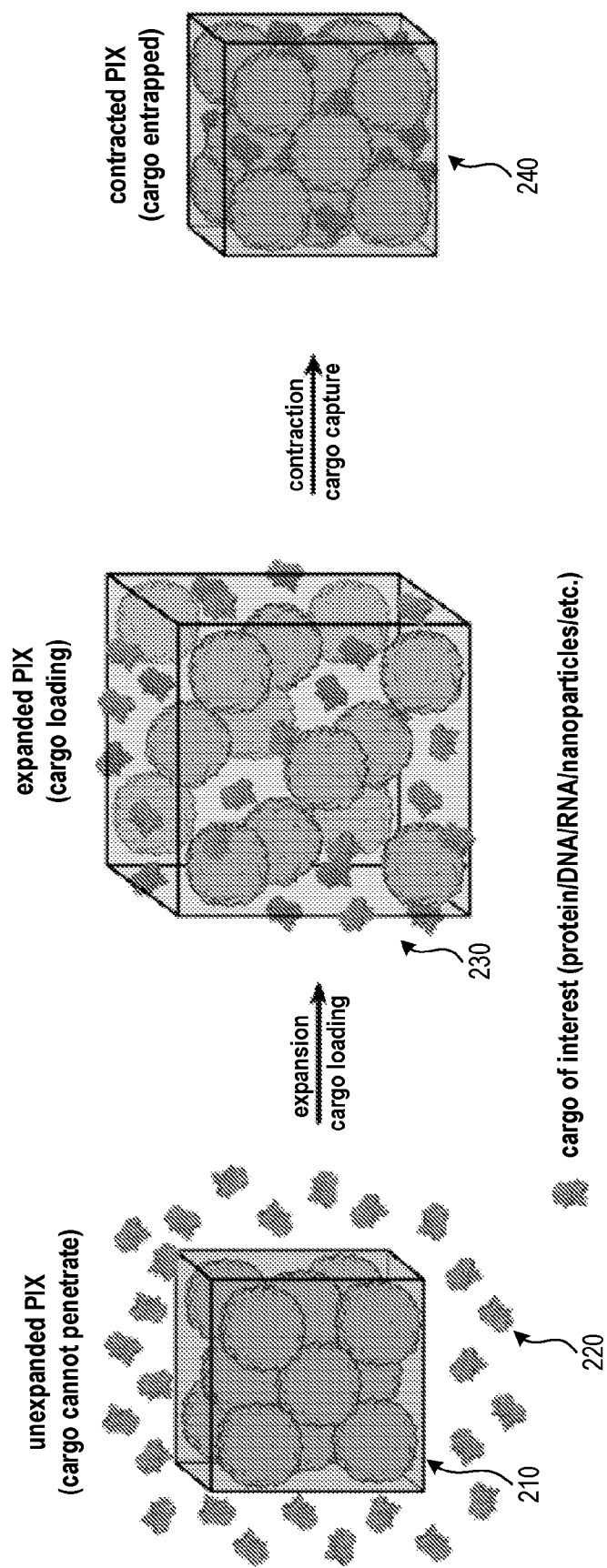
FIGS. 2 and 3 show diagrams illustrating the engineered reversibly-expandable and contractible properties of the disclosed PIX materials, in accordance with the disclosed technology.

The disclosed PIX materials can be configured to have reversible expandability, as illustrated in FIG. 2, for example, and can be tailored to have certain chemical properties of the protein lattice and the hydrogel networks that can enable them to (1) encapsulate molecules, including large macromolecular cargo of interest (e.g., proteins, DNA/RNA, nanoparticles, and others), and (2) release the encapsulated cargo upon demand.

Typically, large molecules or nanoparticles cannot penetrate into a normal protein crystal because (a) they are either larger than the interstitial spaces or the channels between the protein molecules in the crystal lattice, and/or (b) they are electrostatically repelled by the protein lattice. Yet, in implementations of the disclosed PIX materials, for example, upon expansion of the PIX material (e.g., through transfer of the PIX material into a low-ionic-strength environment (e.g., a solution)), the polymer-integrated crystals of the PIX material can allow the cargo molecules of interest to diffuse into the lattice of the crystal. Upon contraction of the PIX material (e.g., through transfer of the PIX material into a high-ionic strength environment (e.g., solution)), the polymer-integrated crystals of the PIX material can stably entrap the guest/cargo molecules within the crystals. The same result can also be achieved in some example embodiments even without PIX expansion, if the polymer matrix in a PIX material has, for example, an opposite charge to that of the guest molecules of interest (such as, e.g., sufficiently small guest proteins), thus allowing them to partition into the polymer-integrated crystals of the PIX material through favorable electrostatic interactions.

Figure 3:
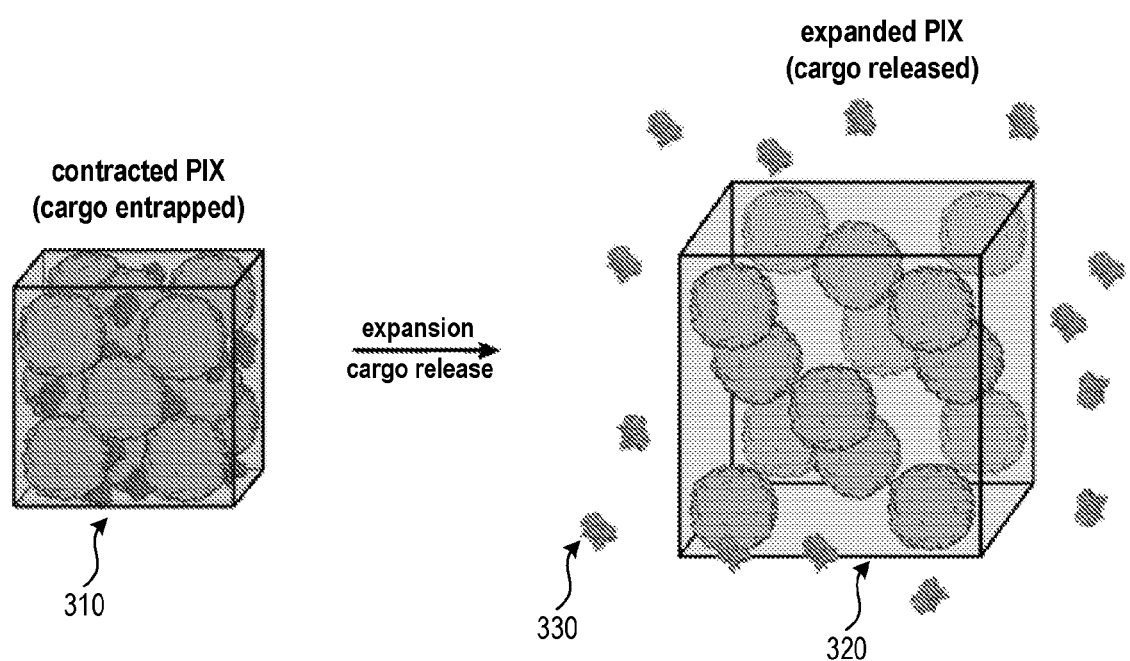

FIGS. 2 and 3 show diagrams illustrating the engineered reversibly-expandable and contractible properties of the disclosed PIX materials, in accordance with the present technology.

The diagram of FIG. 2 illustrates a process of controlled expansion of a PIX material according to the present disclosure to load a cargo of interest, such as, e.g., a protein, DNA, RNA, nanoparticle, or other large or small molecular cargo entities into the polymer-integrated crystals of the PIX material. After expansion of the polymer-integrated crystals and loading the cargo into the crystals, the PIX material can be controllably contracted to entrap the cargo within the polymer-integrated crystals of the material. In some example embodiments, expansion of the polymer-integrated crystals may be achieved, e.g., through transfer of the crystals into a low-ionic-strength environment such as, e.g., a low-ionic-strength solution. According to some example embodiments, contraction of the polymer-integrated crystals may be achieved, e.g., via transfer of the crystals into a high-ionic strength environment such as, e.g., a high-ionic strength solution. FIG. 2 shows a polymer-integrated crystal (PIX) 210 according to an example embodiment which is surrounded by entities (e.g., molecules) of molecular cargo, including an entity 220. FIG. 2 further illustrates that after expansion of the polymer-integrated crystal 210, the molecular cargo may enter and spread through the inner space of the expanded crystal thus forming an expanded crystal 230 which includes the molecular cargo in its inner volume (the crystal 230 can be viewed as a state or a configuration of the crystal 210). FIG. 2 also shows that, upon contraction of the crystal 230, the molecular cargo remains trapped within the contracted crystal configuration 240.

As shown in FIG. 3, the PIX material loaded with cargo molecules or particles is stable in the contracted state. The cargo molecules/particles are only released from the polymer-integrated crystals upon their re-expansion in response to external stimuli including but not limited to, e.g., the lowering of ionic strength, change in pH, or other stimuli. In this manner, the disclosed PIX materials represent an advanced biocompatible platform for the controlled entrapment and release of large biological and non-biological cargo. FIG. 3 shows that expansion of a polymer-integrated crystal which incorporates cargo particles (e.g., molecules and/or nanoparticles) from a contracted configuration 310 into an expanded configuration 320 leads to release of the cargo particles 330 from the polymer-integrated crystal.

For example, in implementations of the reversibly-expandable PIX material, external stimuli can be applied within an external environment of the PIX material. Examples of the external stimuli that can trigger cargo entrapment and/or release into/from a PIX material according to the present disclosure include: (i) changing the ionic strength of the external environment, e.g., where a decrease in ionic strength causes expansion of the polymer and thereby the PIX material, and an increase in ionic strength causes contraction of the polymer and thereby the PIX material; (ii) changing the pH of the external environment, e.g., where protonation states of the protein and polymer species affect the PIX material integrity, leading to cargo release; (iii) adding organic solvents or detergents (e.g. dimethyl sulfoxide, acetonitrile, dimethylformamide, sodium dodecyl sulfate) to the external environment, as these may cause the protein components of the polymer-integrated crystals to be disrupted; (iv) adding metal chelating agents (e.g., ethylenediaminetetraacetic acid) to the external environment, as these can disrupt both protein-protein interactions in the lattice and polymer structure within the polymer-integrated crystals; and (v) and changing the temperature of the external environment. In some implementations, for example, more than one stimuli parameter can be varied (e.g., pH and ionic strengths changes) to trigger cargo release.

The example external stimuli (also referred to as triggers) can act by either directly disrupting (i) the structural integrity of the PIX material (e.g., through altered protein-protein interactions, protein-polymer interactions or the folding of protein (e.g., ferritin) itself) or (ii) the interactions between the PIX and the encapsulated molecular cargo, e.g., causing the release of the molecular cargo.

Figure 4:
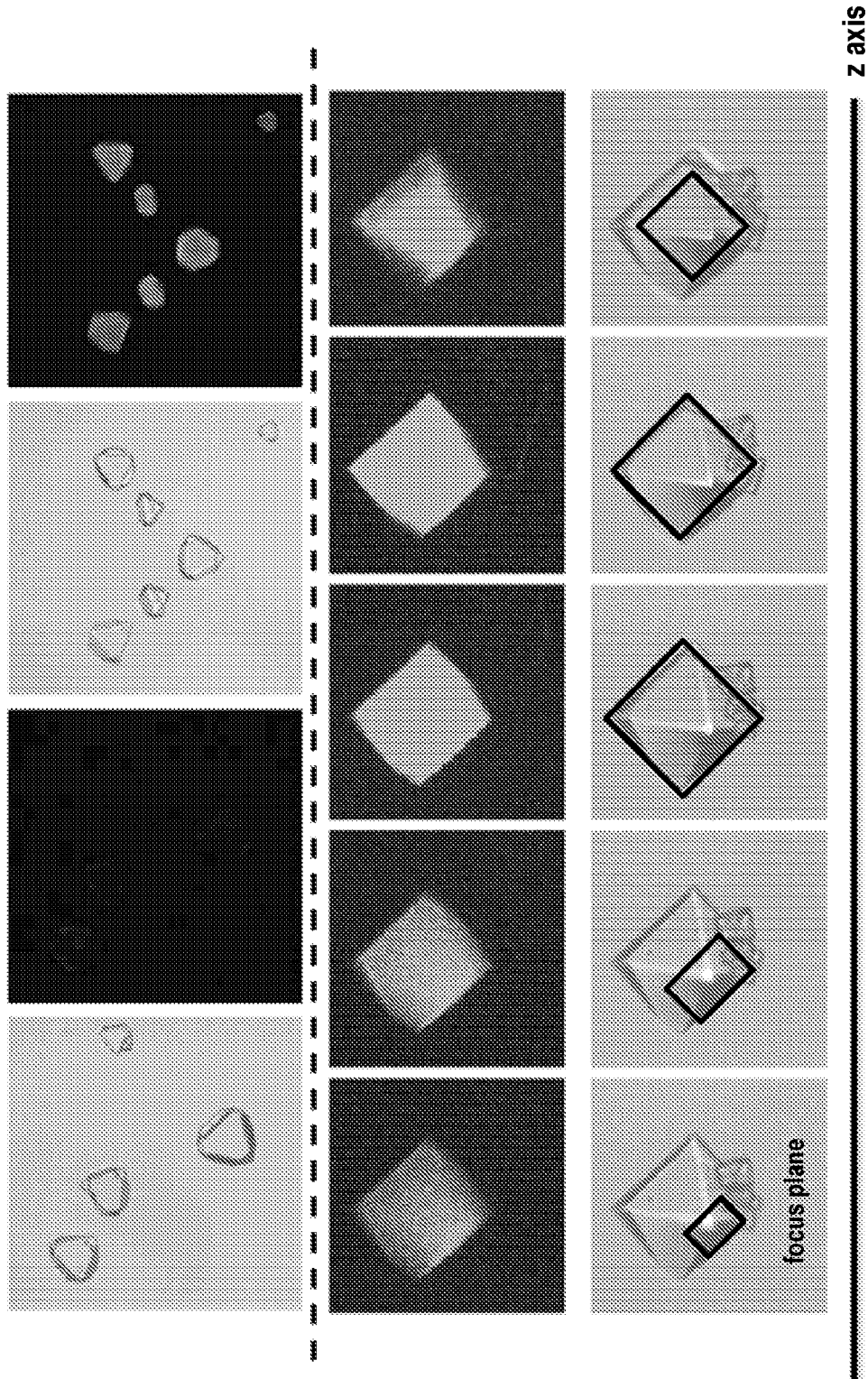
FIG. 4 shows image data from an example implementation of the disclosed PIX materials demonstrating encapsulation of green fluorescent protein (GFP) by an example embodiment of a PIX material.

FIG. 4 shows image data from an example implementation of the disclosed PIX materials demonstrating encapsulation of green fluorescent protein (GFP) by an example embodiment of a ferritin-PIX material (a PIX material which includes polymer-integrated ferritin crystals). The top portion of FIG. 4 shows confocal microscopy images of control experiments for GFP encapsulation (brightfeld-left; fluorescence-right). Non-expanded polymer-integrated crystals soaked in a GFP solution supplemented with CaCl$_2$) are shown in the left two images, and expanded polymer-integrated crystals soaked in a GFP solution are shown in the right two images in the top portion of FIG. 4. As data in FIG. 4 demonstrates, GFP cannot penetrate into non-expanded PIX material, but is efficiently incorporated upon expansion of the PIX material.

The bottom two panels in FIG. 4 show confocal microscopy images of cross-sections of an example polymer-integrated ferritin crystal of a ferritin-PIX material according to the present disclosure with encapsulated green fluorescent protein (GFP). Brightfield channel images are shown below the fluorescence images. The cross-section images confirm that GFP has fully permeated the crystal.

Figure 5:
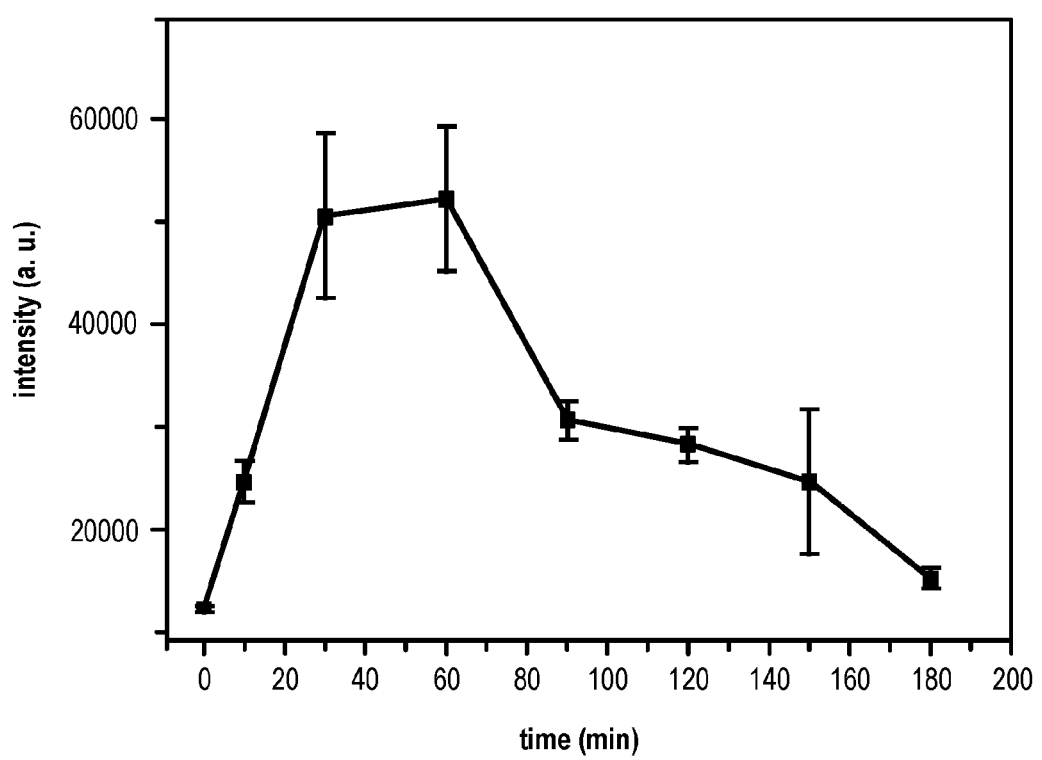
FIG. 5 shows a data plot depicting GFP encapsulation yield in an example PIX material.

FIG. 5 shows a data plot depicting optimization of GFP encapsulation yield in an example ferritin-PIX material. For example, ferritin-PIX samples were incubated in a GFP-containing solution (with simultaneous expansion) and then imaged by confocal microscopy at different time points to determine the optimal duration for GFP encapsulation. The example results shown in the plot demonstrate that GFP encapsulation in ferritin-PIX is maximized at 30-60 min of expansion/incubation. Notably, for example, longer expansion times can lead to the disintegration of PIX, thus lowering the yield of GFP encapsulation.

Figure 6:
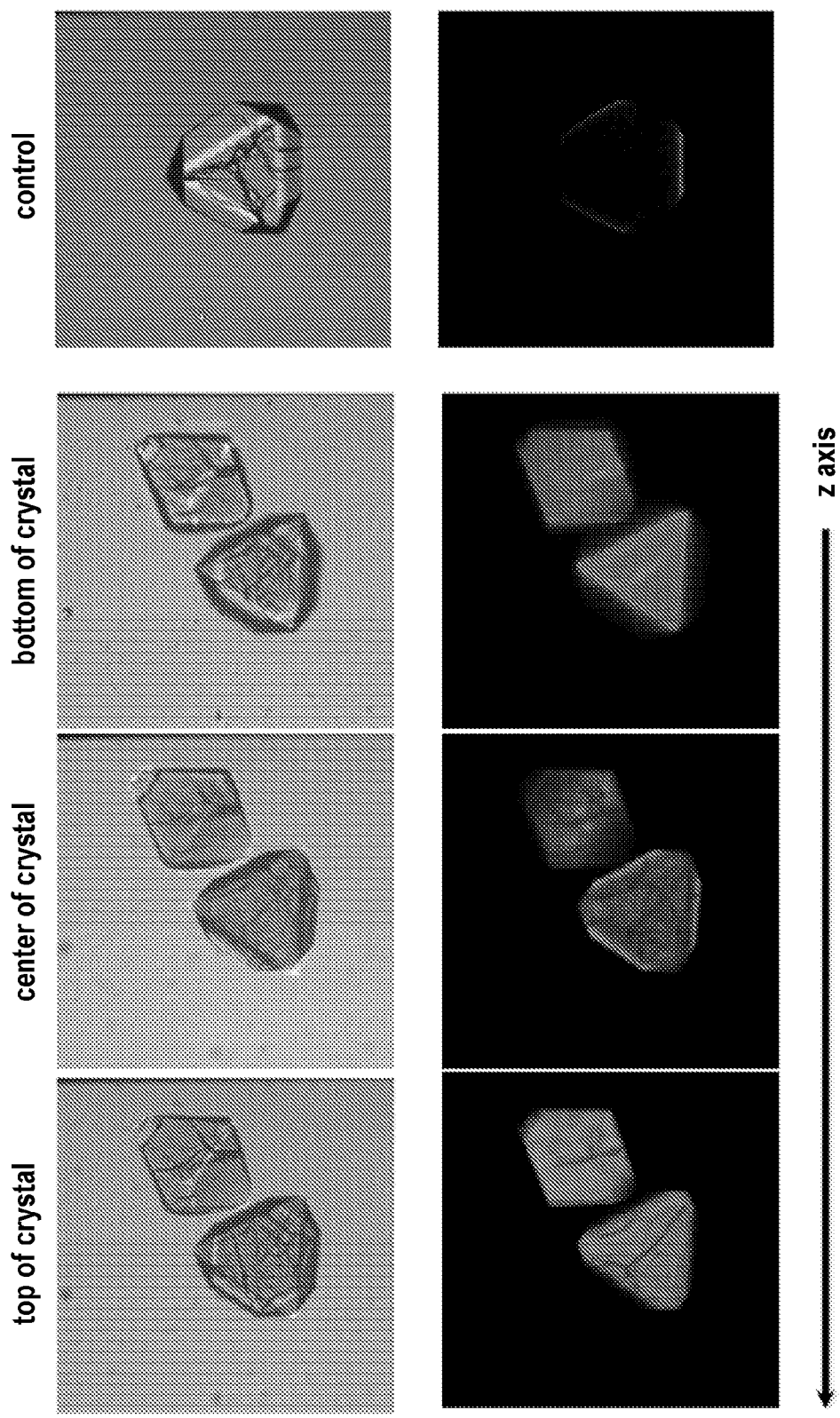
FIG. 6 shows image data from an example implementation of the disclosed PIX materials demonstrating encapsulation of bovine serum albumin (BSA) within an example PIX material.

FIG. 6 shows image data from an example implementation of the disclosed PIX materials demonstrating encapsulation of bovine serum albumin (BSA) within an example ferritin-PIX material. The image data of FIG. 6 shows confocal microscopy images of cross-sections of two polymer-integrated ferritin crystals with encapsulated BSA. BSA was covalently labeled with a rhodamine fluorophore for fluorescence imaging. Cross-section images confirm that BSA has fully permeated the crystals. The corresponding brightfield channel images are in the above panel in FIG. 6.

Figure 7A:
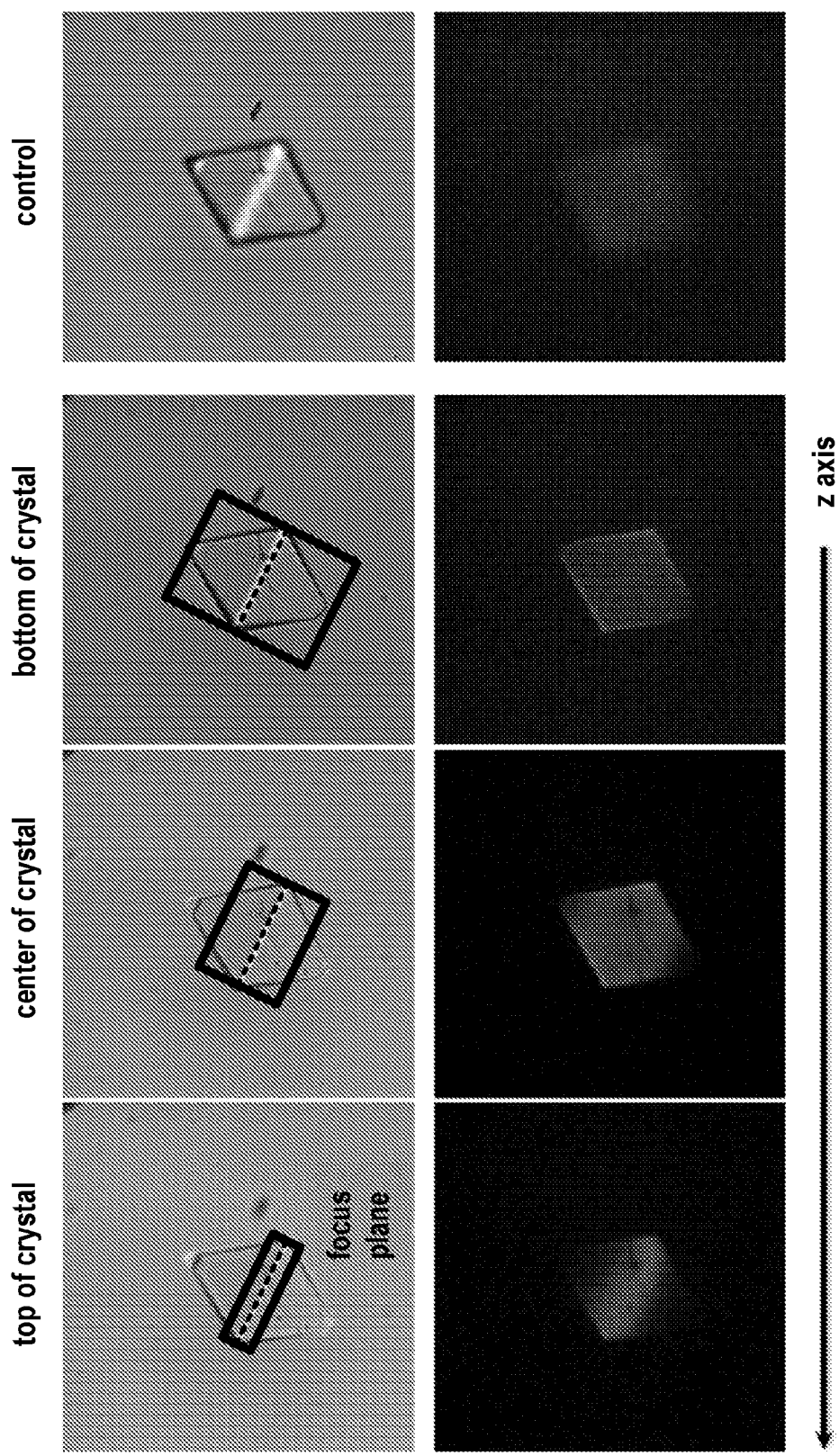
FIG. 7A shows image data from an example implementation of the disclosed PIX materials demonstrating encapsulation of lysozyme within an example PIX material.

FIG. 7A shows image data from an example implementation of the disclosed PIX materials demonstrating encapsulation of lysozyme within an example ferritin-PIX material. The image data of FIG. 7A shows confocal microscopy images of cross-sections of a polymer-integrated ferritin crystal with encapsulated lysozyme. Lysozyme was covalently labeled with a rhodamine fluorophore for fluorescence imaging. Cross-section images confirm that Lysozyme has fully permeated the crystal. The corresponding brightfield channel images are in the above panel in FIG. 7A.

Figure 7B:
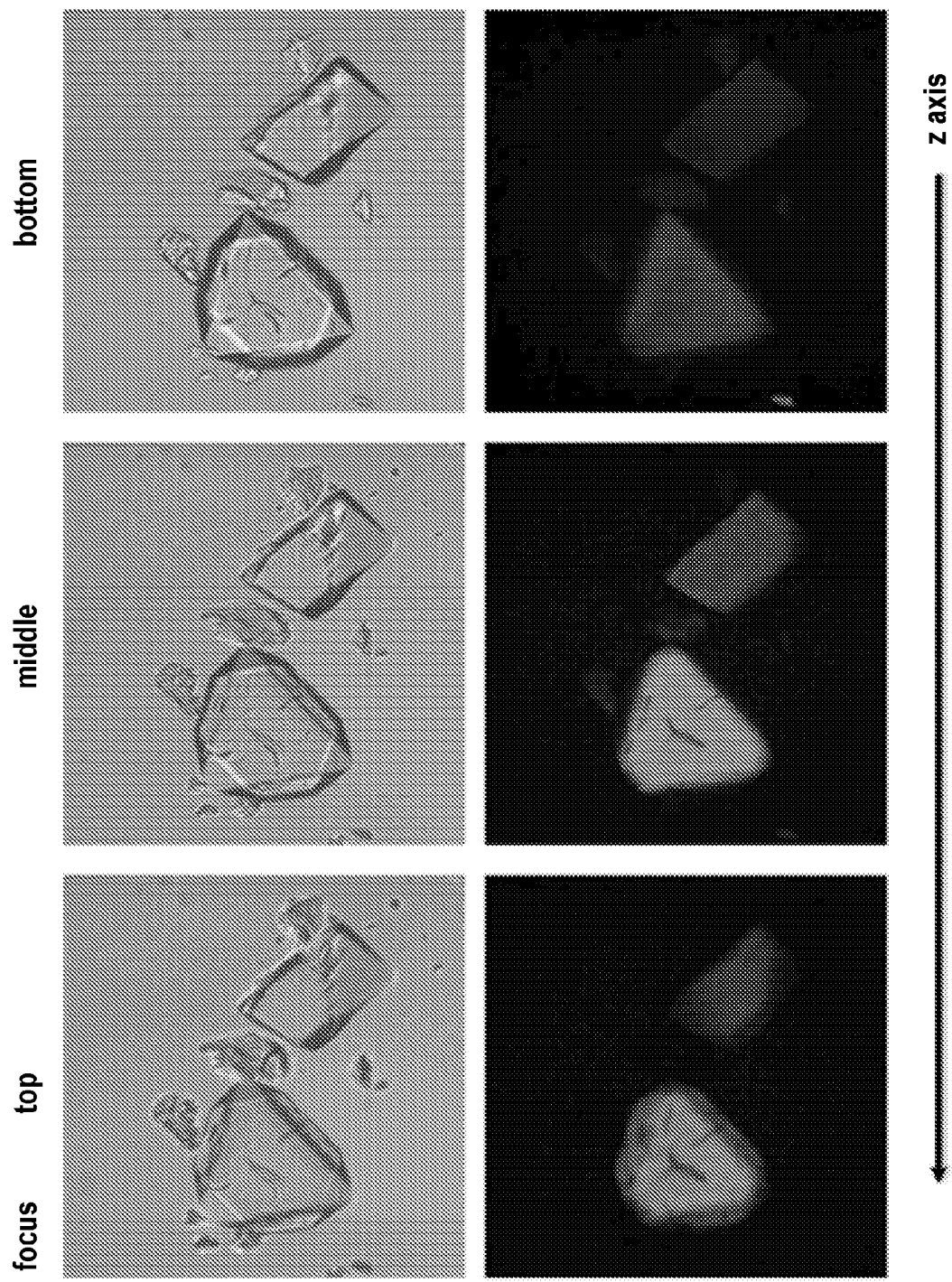
FIG. 7B shows image data from an example implementation of the disclosed PIX materials demonstrating encapsulation of insulin within an example PIX material.

FIG. 7B shows image data from an example implementation of the disclosed PIX materials demonstrating encapsulation of insulin within an example ferritin-PIX material. Insulin was covalently labeled with a rhodamine fluorophore for fluorescence imaging. Cross-section images confirm that insulin has fully permeated the crystals. The corresponding brightfield channel images are in the above panel in FIG. 7B.

In some implementations of the disclosed PIX materials, small, charged molecules like, e.g., lysozyme (which is small and positively charged protein, MW<20 kDa, pI~11) were able to be entrapped inside the PIX material without the explicit expansion/contraction process described above. This is enabled, at least partially, by the negative charge of the polymer matrix of the PIX material that attracts the positively charged cargo. Notably, without the polymer formation, lysozyme cannot penetrate into the ferritin crystals of the example PIX material structure. This example result suggests that other small, charged cargo can also be entrapped inside the PIX materials according to the present disclosure—for example, if the polymer matrix is positively charged, then negatively charged molecules like DNA and RNA can be trapped inside—further enabling the use of the disclosed PIX materials for controllably entrapping and releasing molecular cargo.

Figure 8A:
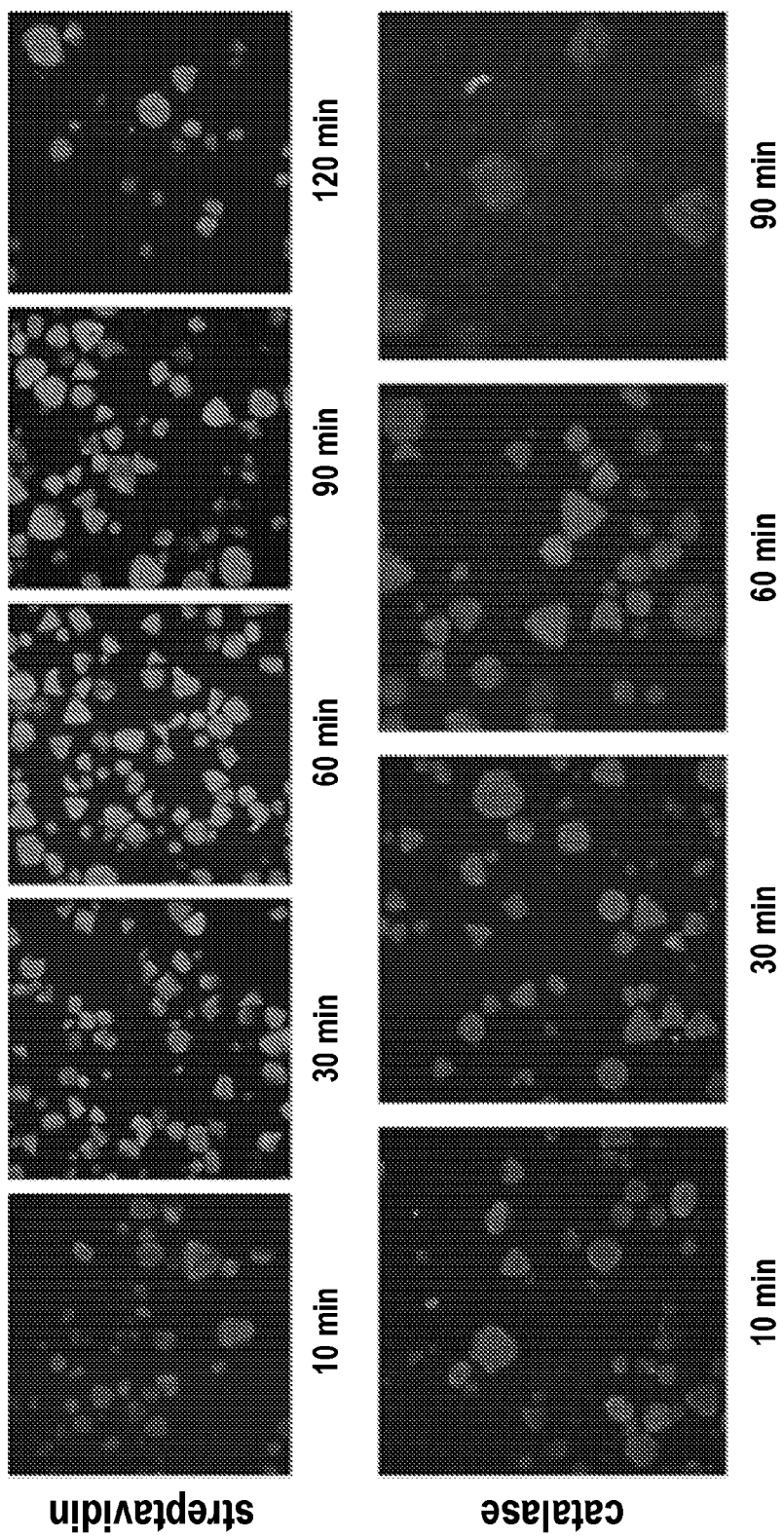
FIGS. 8A and 8B show image data and a data plot, respectively, depicting example results from an example implementation of the disclosed PIX materials, showing encapsulation yields of catalase and streptavidin within an example PIX material.
Figure 8B:
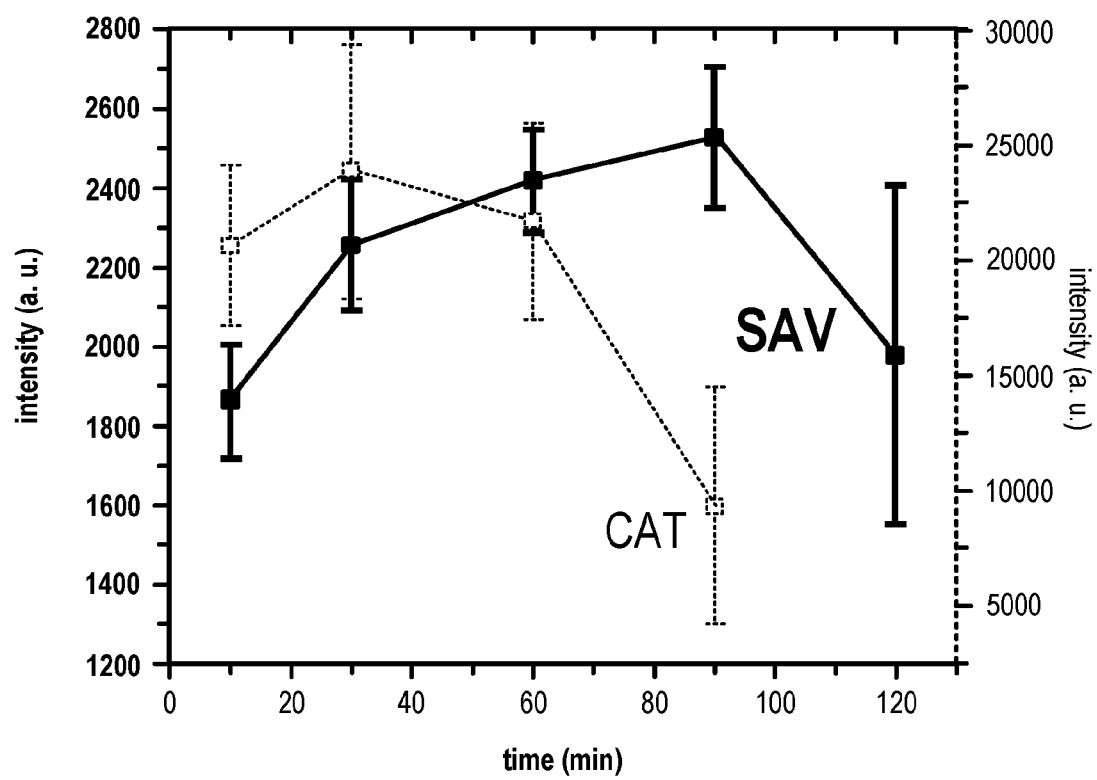

FIGS. 8A and 8B show image data and a corresponding data plot depicting example results from an optimization implementation, showing encapsulation yields of catalase and streptavidin within an example ferritin-PIX material according to the present disclosure. Ferritin-PIX samples were incubated in streptavidin-or catalase-containing solutions (with simultaneous expansion) and then imaged by confocal microscopy at different time points to determine the optimal duration for guest encapsulation, as shown in FIG. 8A. Prior to these experiments, streptavidin and catalase were functionalized with rhodamine. As shown in the graph in FIG. 8B, the encapsulation in ferritin-PIX is maximized at ~30 min of incubation for catalase and ~90 min for streptavidin.

FIG. 9 shows confocal microscopy images of a ferritin-PIX material according to an example embodiment encapsulated with gold nanoparticles of, e.g., 5 nm in diameter. The reflective image (right) confirms that nanoparticles are entrapped within the PIX, and the corresponding brightfield channel image is shown on the left in FIG. 9.

FIG. 10 shows image data and a data plot illustrating example results from an example implementation demonstrating controlled release of cargo molecules from an example ferritin-PIX material. Polymer-integrated ferritin crystals containing encapsulated GFP were transferred into low ionic strength solution to enable re-expansion of the crystals and then imaged by confocal microscopy at different time points to monitor GFP release. As also shown in the graph on the right. GFP release is nearly complete within 10 min of expansion. Time lapse brightfield channel images and fluorescent images are shown on the left of FIG. 10.

Figure 11B:
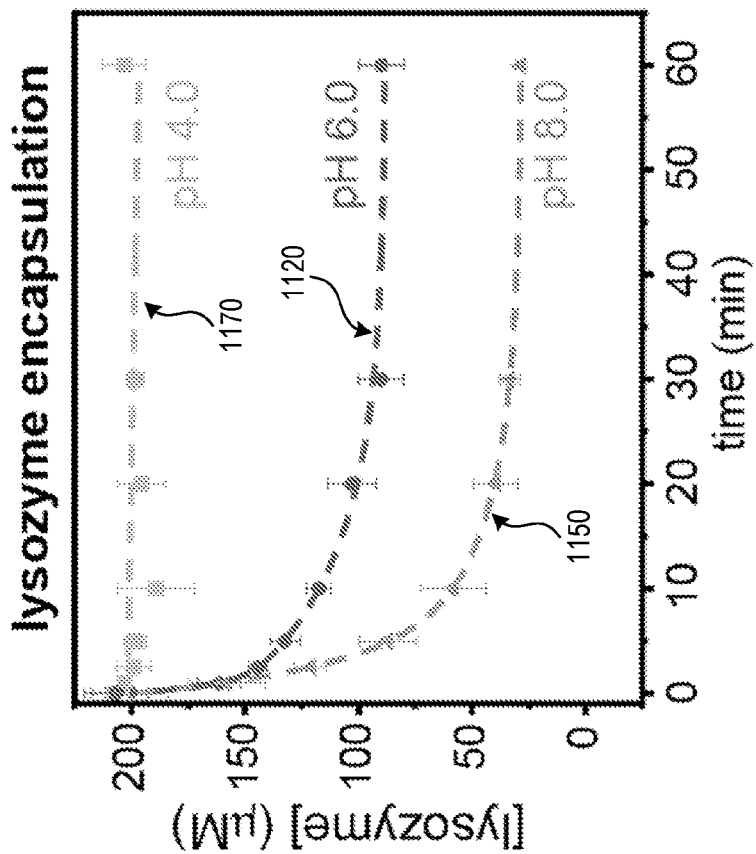
FIGS. 11A and 11B illustrate uptake of cytochrome c and lysozyme by an example embodiment of a PIX material according to the present disclosure.
Figure 11A:
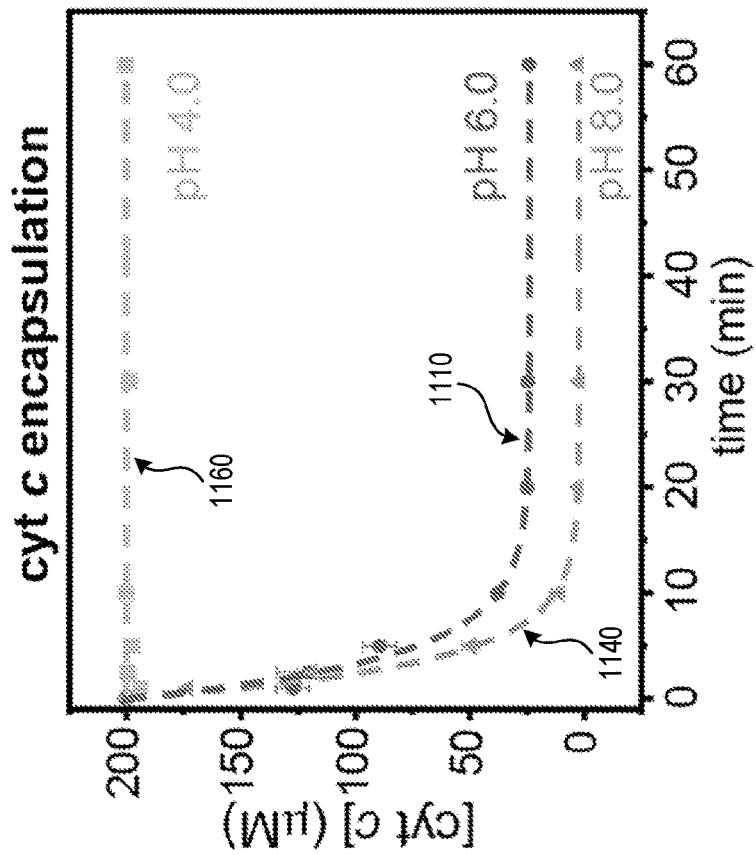
Figure 12:
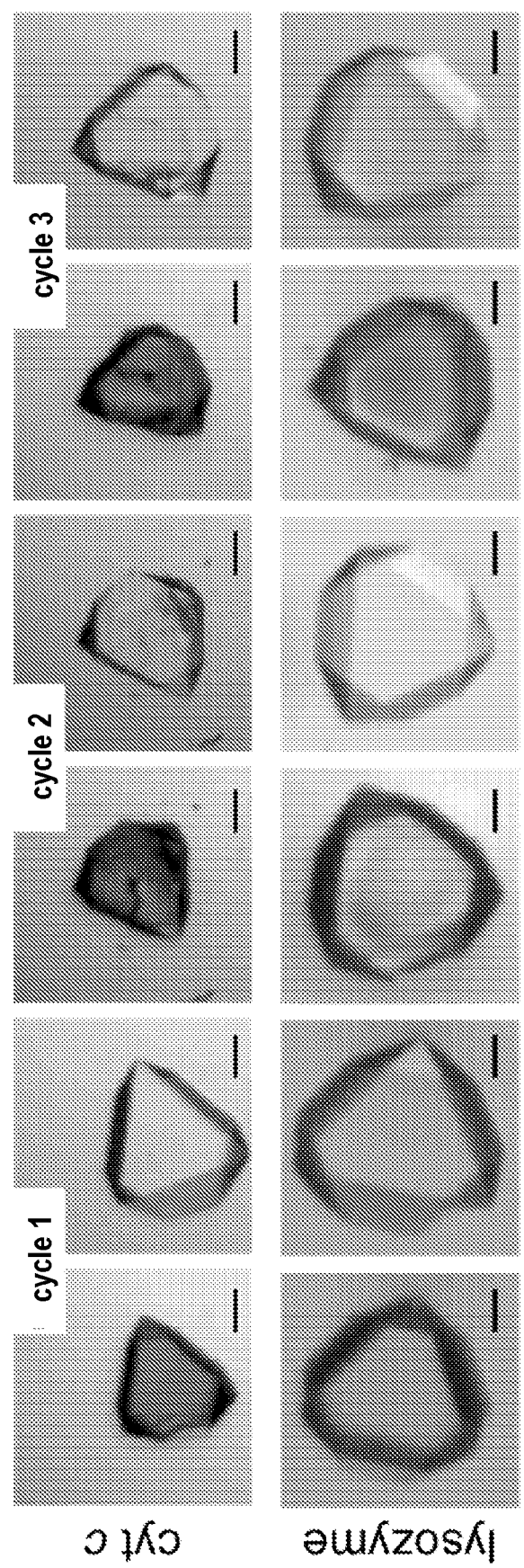
FIG. 12 shows image data obtained during three consecutive cycles of uptake and release of cytochrome c (top) and lysozyme (bottom) by an example embodiment of a PIX material according to the disclosed technology.

FIGS. 11A and 11B illustrate uptake of cytochrome c (FIG. 11A) and lysozyme (FIG. 11B) by an example embodiment of a PIX material according to the present disclosure. PIX materials (e.g., ferritin-PIX materials) according to the present disclosure can be used for highly-efficient, reversible uptake and release of guest molecules (e.g., proteins) or particles (e.g., nanoparticles). Given the fact that ferritin-PIX are negatively charged at neutral pH (ferritin pI=5.1, polyacrylate polymer pKa ~4.5), they can display particularly high uptake capacities for positively charged guest species (e.g., proteins). For example, ferritin-PIX can rapidly sequester both cytochrome c (pI=10.3) and lysozyme (pI=10.8) within minutes at pH 6 (lines 1110 and 1120 in FIGS. 11A and 11B, respectively). The uptake efficiency could be further augmented (e.g., accelerated) at pH 8 (lines 1140 and 1150 in FIGS. 11A and 11B for cytochrome c and lysozyme, respectively), which resulted in a total uptake capacity of 23% (w/w) for cytochrome c and 30% (w/w) for lysozyme. To obtain data shown in FIGS. 11A and 11B, ferritin PIX (which are opaque crystals) were placed in a 200 mM guest protein solution, and the uptake was monitored by measuring the UV-Vis absorbance spectra of the supernatant. Both cytochrome c and lysozyme proteins were labeled with rhodamine molecules for visualization, giving these guest proteins a red-purple color. Data shown in FIGS. 11A and 11B also indicate that at pH 4, ferritin-PIX become positively charged and can no longer uptake guest proteins (lines 1160 and 1170 in FIGS. 11A and 11B for cytochrome c and lysozyme, respectively). The sequestered guest proteins can be efficiently released from ferritin-PIX upon lowering the pH below 3 without losing the crystallinity of ferritin PIX. This reversible, pH-dependent uptake and release cycle could be repeated multiple times, as illustrated in FIG. 12 without loss of efficiency. FIG. 12 shows image data obtained during three consecutive cycles of uptake and release of cytochrome c (top) and lysozyme (bottom) by an example embodiment of a PIX material according to the disclosed technology. FIG. 13 illustrates a cycle of pH-dependent protein uptake, release and re-uptake by an example embodiment of a PIX material according to the disclosed technology.

In some example implementations, for preparing the example PIX material, ferritin crystals were formed through sitting drop vapor diffusion technique. For example, octahedron-shaped ferritin crystals were formed over 1-2 days in a buffered solution containing 25 mM HEPES pH 7.0, 3-14.5 µM protein (per 24meric ferritin cage), and 4.5-7.5 mM $CaCl_2$). Once the crystals were large enough (within 1-2 days), they were transferred into a polymer precursor solution containing, e.g., 25 mM HEPES (pH 7.0), 30 mM $CaCl_2$), 8.625% (w/v) sodium acrylate, 2.5% (w/v) acrylamide, and (0.2% w/v) N,N'-methylenebis(acrylamide) for, e.g., >10 hours (e.g., at least 12 h) to ensure full infusion of the polymer monomers into the ferritin crystals. The crystals were then either individually transferred using a mounted CryoLoop (Hampton) to the polymerization solution (e.g., 1% (w/v) ammonium persulfate (APS), 1% (v/v) tetramethylethylenediamine (TEMED), and 4 M NaCl) for 5-10 min or the polymer precursor solution was exchanged for the polymerization solution for 5-10 min for the bulk polymerization of many crystals at once, to initiate radical polymerization and effectively form a hydrogel network within the crystal lattice. Protein crystals can also be prepared for example, in bulk without a reservoir solution and further processed into a PIX using 24-well culture plates.

Also, for example, in some implementations for entrapping molecular cargo within the example PIX material, freshly prepared ferritin-PIX were transferred into a 1.5 mL Eppendorf tube and washed twice with 500 µL of 50 mM MES (pH 6.0). The supernatant was discarded after mild centrifugation. A 500 µL solution containing 100 UM of guest protein (in 50 mM MES, pl 6.0) or nanoparticles were added to the crystals and the tube was placed on a gel rocker. After 10-30 min, 100 µL of 4 M NaCl was added portion-wise-25 µL every 10 s—to induce PIX contraction. Similarly, an additional 100 µL of 1 M $CaCl_2$) was added portionwise, effectively entrapping the protein/nanoparticle of interest. The excess protein solution was washed away with 1 M $CaCl_2$) and the PIX was stored in 1 M $CaCl_2$).

FIGS. 14A-14D depict an example packing arrangement in ferritin crystals according to the disclosed technology.

Ferritin has one or more of the following characteristics: it is a 24-meric, quasi-spherical protein with 432 symmetry, an outer diameter of 12 nm, an inner diameter of 8 nm, and a molecular weight of >500,000 Da. Human heavy-chain ferritin can form highly ordered, face-centered cubic (fcc) crystals that grow to >200 µm in size and diffract to <2.0 Å. The fcc lattice (FIG. 14A) is characterized by a mesoporous network consisting of cube-shaped, 6-nm wide chambers (FIG. 14B) that are interconnected by smaller, octahedron-shaped cavities that taper to a pore size of about 2 nm at their narrowest (FIG. 14C). The lattice is formed through highly specific, metal-mediated contacts between neighboring ferritin molecules (FIG. 14D), which are promoted through the K86Q surface mutation to enable metal coordination. The absence of any other interprotein contacts means that the lattice bonding framework of ferritin molecules can be formed or broken via binding or removal of metal ions (e.g., $Ca^{2+}$). Furthermore, ferritin can bear a small negative charge, with a zeta potential ranging from -5.5 mV at pH 6.0 to -7.3 mV at pH 7.5. The exterior surface of ferritin presents a diffuse distribution of both negatively and positively charged residues, which can enable uniform association with the poly(acrylate-acrylamide), also referred to as p(Ac-Am), network through a combination of ionic and H-bonding interactions.

Figure 14A:
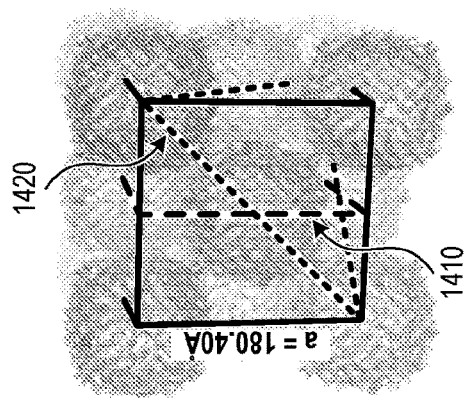
FIGS. 14A-14D depict an example packing arrangement in ferritin crystals according to the disclosed technology.
Figure 14B:
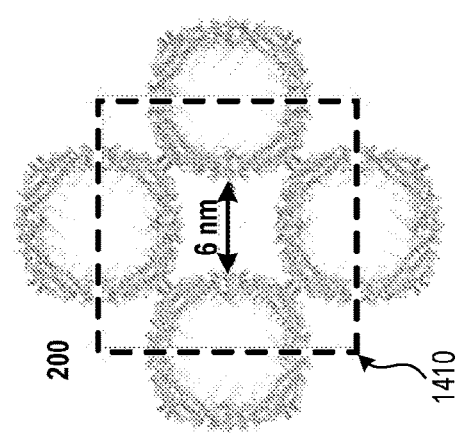
Figure 14C:
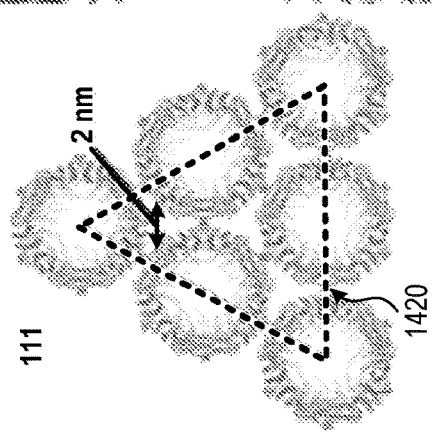
Figure 14D:
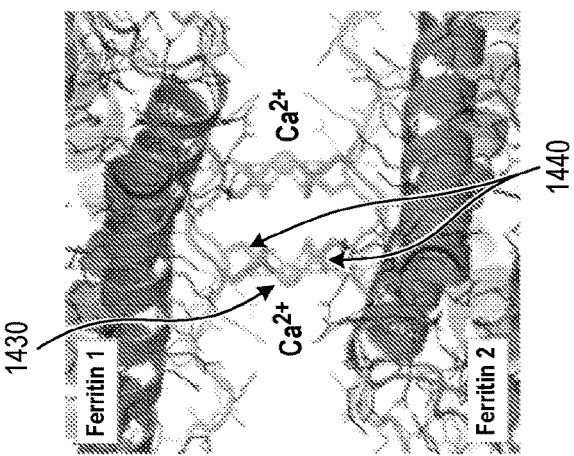

FIGS. 14A-14C depict a face-centered cubic packing arrangement of ferritin crystals according to an example embodiment. FIGS. 14A-14C show the 111 plane (1410 in FIGS. 14A-14C) and the 200 plane (1420 in FIGS. 14A-14C). FIG. 14D depicts Ca-mediated intermolecular interactions between ferritin molecules in the lattice. Each of the $Ca^{2+}$ ions 1430 is coordinated by a pair of D84 and Q86 sidechains 1440. The cubic lattice is formed through the $Ca^{2+}$-D84/Q86-mediated association of the C2 symmetric interfaces of each ferritin molecule with 12 neighbors. The cubic ferritin lattice, like many protein crystals, is mesoporous, with continuously linked, nm-sized channels that account for an interstitial solvent content of 39%. This porosity allows the full permeation of ferritin crystals with acrylate polymer precursors and the subsequent formation of a pervasive polyacrylate (pA) hydrogel network within the lattice. Owing to the extensive noncovalent interactions between pA side chains and the surfaces of ferritin molecules, the resulting materials according to the present disclosure behave essentially as singular chemical units that exhibit unprecedented material properties. For example, pA-ferritin PIX can reversibly expand and/or contract in response to changes in ionic strength by more than 100% and, in some example embodiments, by more than 500% (e.g., nearly 600%) in volume without losing crystalline order and display efficient self-healing.

The mechanical and functional properties of many crystalline materials depend on cooperative changes in lattice arrangements in response to external perturbations. However, the flexibility and adaptiveness of crystalline materials are limited. Additionally, the bottom-up, molecular-level design of crystals with desired dynamic and mechanical properties at the macroscopic level remains a considerable challenge. PIX materials according to the present disclosure, such as the ones which include mesoporous cubic ferritin crystals with integrated hydrogel networks, address these challenges resulting in hybrid materials (polymer-integrated crystals or PIX) which can undergo dramatic structural changes while maintaining crystalline periodicity and display efficient self-healing.

Directionality is an important attribute of many molecular and macroscopic materials and devices. Directionality can be achieved in the PIX materials according to the present disclosure through, e.g., the use of ferritin crystals with anisotropic symmetries (rhombohedral or trigonal), which enable the templated formation of patterned hydrogel networks in crystallo. The resulting PIX can expand and contract anisotropically without losing crystallinity, undergo prompt bending motions in response to stimuli, and self-heal efficiently, capturing some of the essential features of sophisticated biological devices like skeletal muscles.

Figure 15:
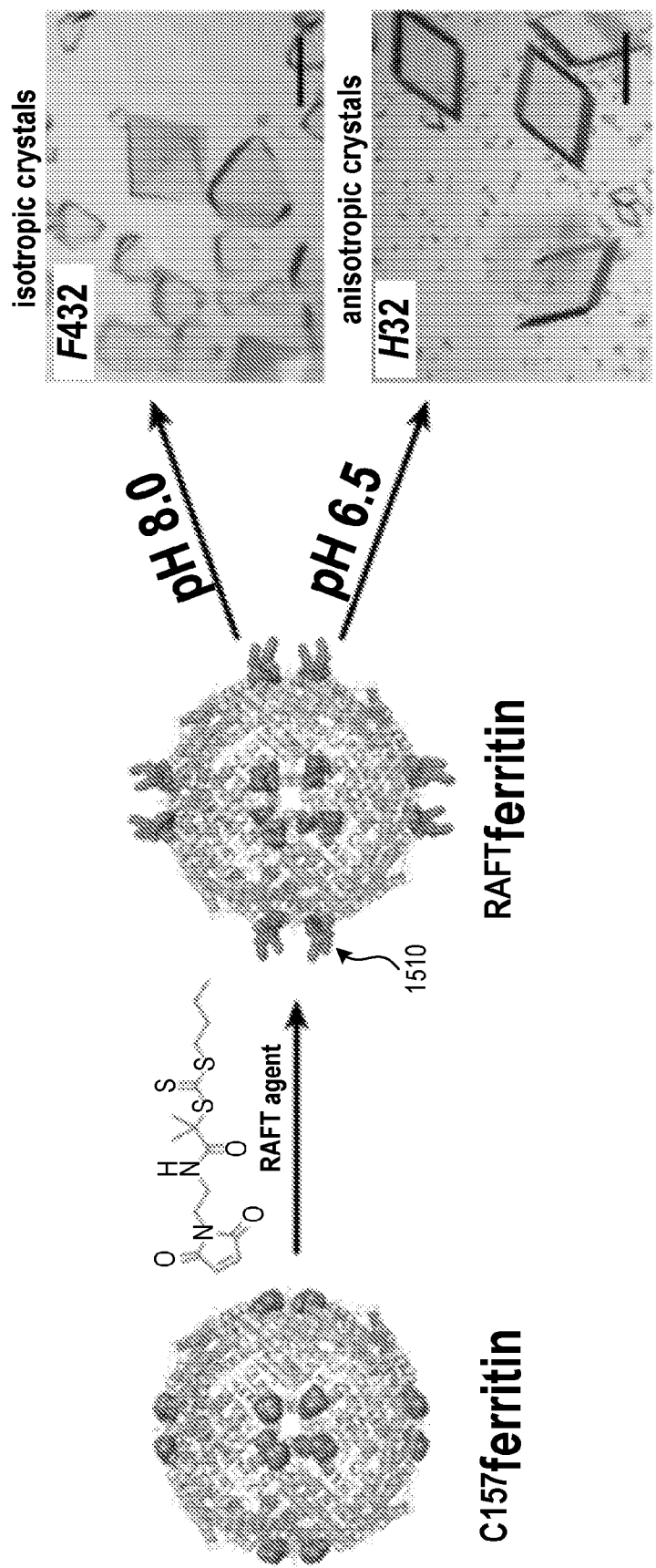
FIG. 15 shows a schematic for the site-specific conjugation of a maleimide-functionalized reversible addition-fragmentation chain-transfer (RAFT) agent to C157 ferritin to form a conjugate, $^{RAFT}$ferritin, which can assemble into isotropic (e.g., cubic) or anisotropic (e.g., rhombohedral) crystals in a pH-dependent manner, according to the disclosed technology.

A ferritin variant that is site-selectively modified with RAFT (reversible addition-fragmentation chain-transfer) agents can be used to generate anisotropic ferritin-PIX materials according to some example embodiments. The RAFT-modified ferritins can enable the controlled growth of polymer networks in spatially well-defined locations within the protein lattice. RAFT polymerization provides excellent compatibility with aqueous solutions and acrylate monomers, does not require transition metal ions (which may interfere with ferritin self-assembly), and can be used to generate covalent protein-polymer hybrids with high efficiency via graft-from strategies. Accordingly, we synthesized a cysteine-specific (Cys-specific) maleimide-functionalized trithiocarbonate RAFT agent (FIGS. 15 and 25). We used this agent to site-selectively label the ferritin variant, $^{C157}$ferritin, which bears a single set of surface-exposed Cys residues (24 total, at positions 157) flanking the ferritin C4 symmetry axes (FIG. 15). A RAFT agent molecule 1510 conjugated with $^{C157}$ferritin is indicated in FIG. 15. The graft-from growth of the polyacrylate (pA) polymer from the modified variant (termed $^{RAFT}$ferritin) could be induced by the radical initiators VA-044 or APS/TEMED and was confirmed by SDS-PAGE electrophoresis and gel permeation chromatography (GPC).

FIG. 15 shows a schematic for the site-specific conjugation of a maleimide-functionalized RAFT agent to $^{C157}$ferritin. The resulting conjugate, $^{RAFT}$ferritin, can assemble into isotropic (cubic, described above) or anisotropic (rhombohedral) crystals in a pH-dependent manner (scale bars: 100 μm).

Figure 16A:
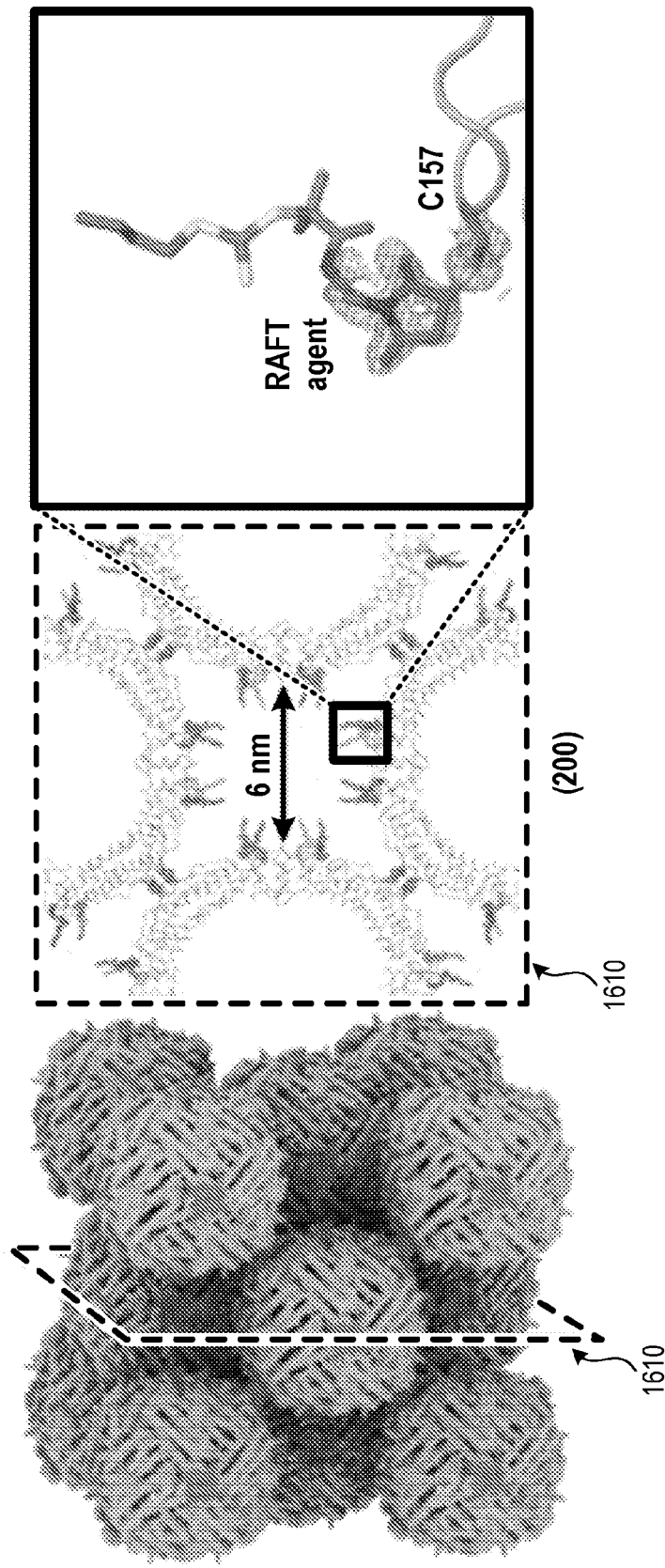
FIG. 16A shows the fcc (F432) packing arrangement of isotropic RAFT ferritin crystals according to an example embodiment.

We next examined the self-assembly of RAFT ferritin into 3D crystals. Under typical conditions used for $Ca^{2+}$-mediated ferritin crystallization (≥5 mM $CaCl_2$), pH 8.0), we obtained octahedron-shaped, fcc crystals (F432, a=179.9 Å, PDB ID: 6WYF) of $^{RAFT}$ferritin that were isomorphous with those of unmodified $^{C157}$ferritin (FIGS. 15 and 16A). RAFT agents attached to the C157 side chains extend into the 6 nm wide, cube-shaped cavities in the lattice and can be discerned in the 1.25-Å resolution crystal structure up to the amide group (FIG. 16A). When the solution pH is lowered to, e.g., ≤6.5, $^{RAFT}$ferritin molecules self-assemble into large (>60 μm) rhombohedron-shaped crystals (H32, a=b=127.0 Å, c=281.7 Å, PDB ID: 6WYG) which lack the 3D isotropy of the fcc crystals (FIGS. 15 and 16B).

FIG. 16A shows the fcc (F432) packing arrangement of the isotropic $^{RAFT}$ferritin crystals according to an example embodiment, along with a view of the lattice along the (200) plane 1610 and a close-up view of the RAFT agents attached to C157 positions. The 2Fo-Fc electron density map for a single conformation of the RAFT-labeled C157 site is contoured at 0.70 in FIG. 16A.

Figure 16B:
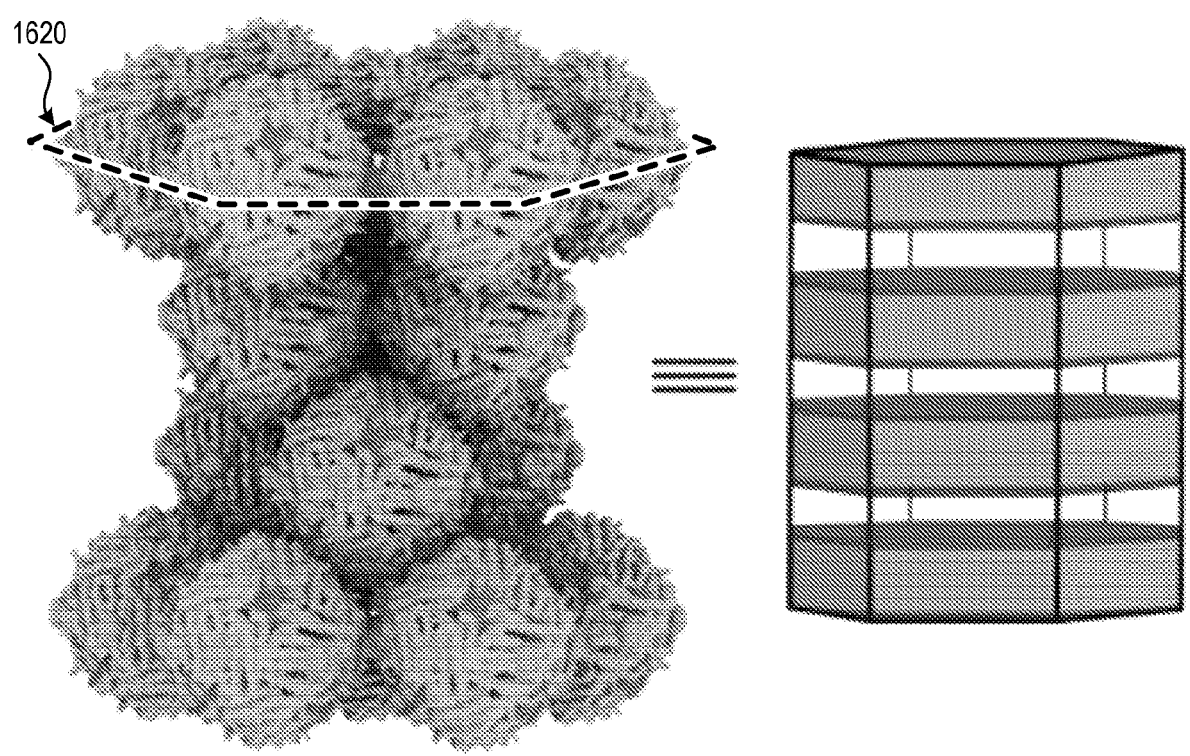
FIG. 16B shows the hexagonal-layered (H32) packing arrangement of anisotropic $^{RAFT}$ferritin crystals according to an example embodiment.

FIG. 16B shows the hexagonal-layered (H32) packing arrangement of the anisotropic $^{RAFT}$ferritin crystals. The (0001) plane is shown as a hexagon 1620.

The rhombohedral (anisotropic) $^{RAFT}$ferritin crystal lattice can be considered as a layered structure (FIG. 16B, right). In the rhombohedral crystal lattice, the hexagonal layers in the ab-plane are mediated by $Ca^{2+}$-D84/Q86 interactions between each ferritin molecule and six neighbors (FIG. 16C), as in the cubic (isotropic) crystals. In contrast, the interlayer interactions along the c-axis are formed by contacts between the hydrophobic patches consisting of groups of four C157-RAFT moieties surrounding the ferritin $C_4$ axes (FIG. 16D). These interactions further connect each ferritin molecule with six additional neighbors in the c-direction, yielding a quasihexagonal close-packed arrangement with a denser packing (interstitial solvent content=32.5%) than the cubic crystals. Electrostatic calculations show that at pH=8, C4 surfaces of ferritin are highly negatively charged and thus self-repulsive, accounting for the fcc arrangement. Upon lowering the pH to, e.g., ≤6.5, the negative charge is mostly mitigated, promoting hydrophobic interlayer interactions. Thus, although each $^{RAFT}$ferritin molecule is inherently isotropic, the energetic balance/competition between different interactions (metal-mediated and hydrophobic) governing its self-assembly yield both isotropic and anisotropic lattice arrangements in a condition-dependent manner.

Figure 16C:
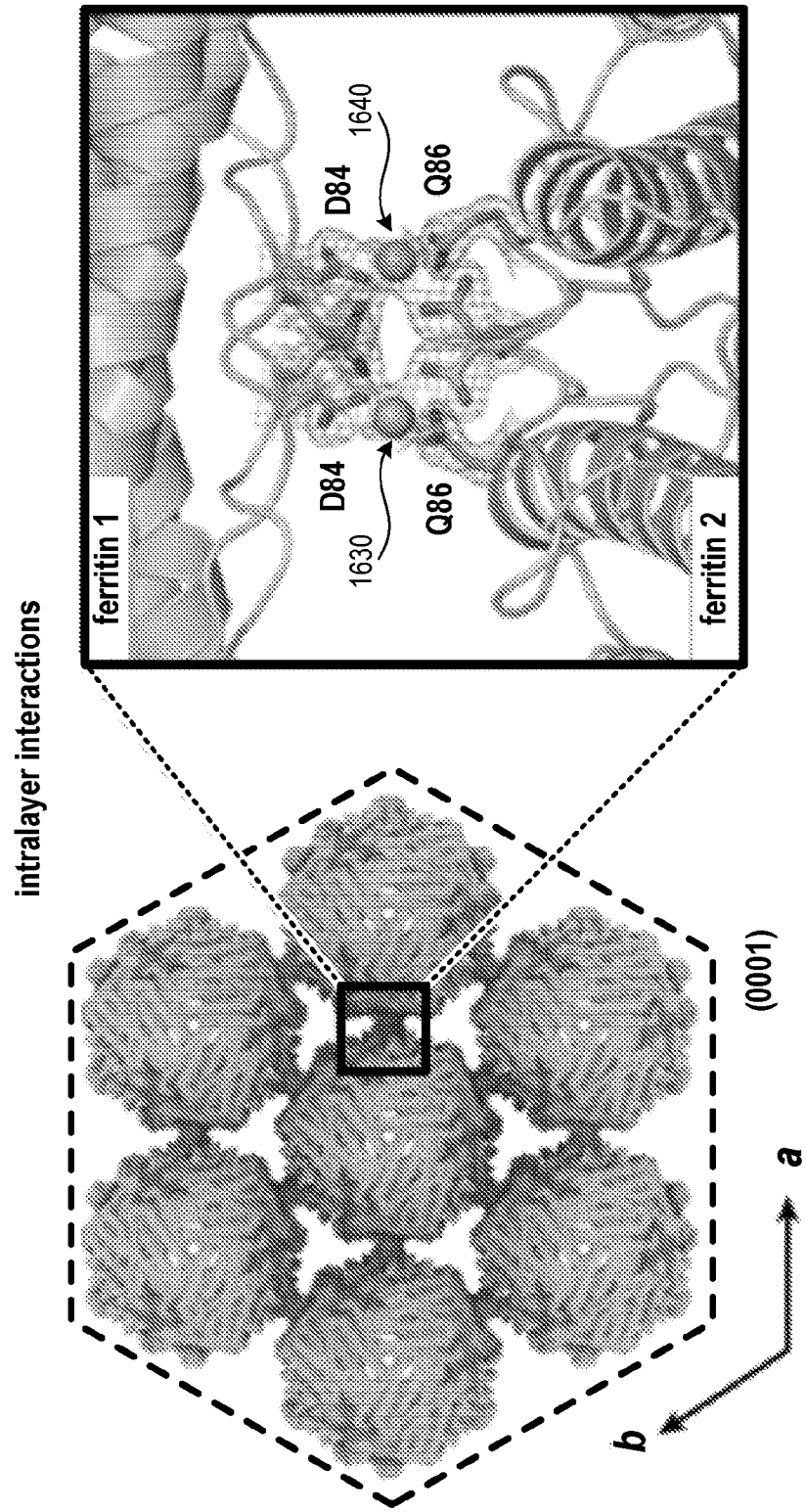
FIG. 16C shows that, in the rhombohedral crystal lattice, intralayer interactions between ferritin molecules in the (0001) plane oriented along the ab-plane are mediated by $Ca^{2+}$ ions and two pairs of D84 and Q86 side chains.
Figure 16D:
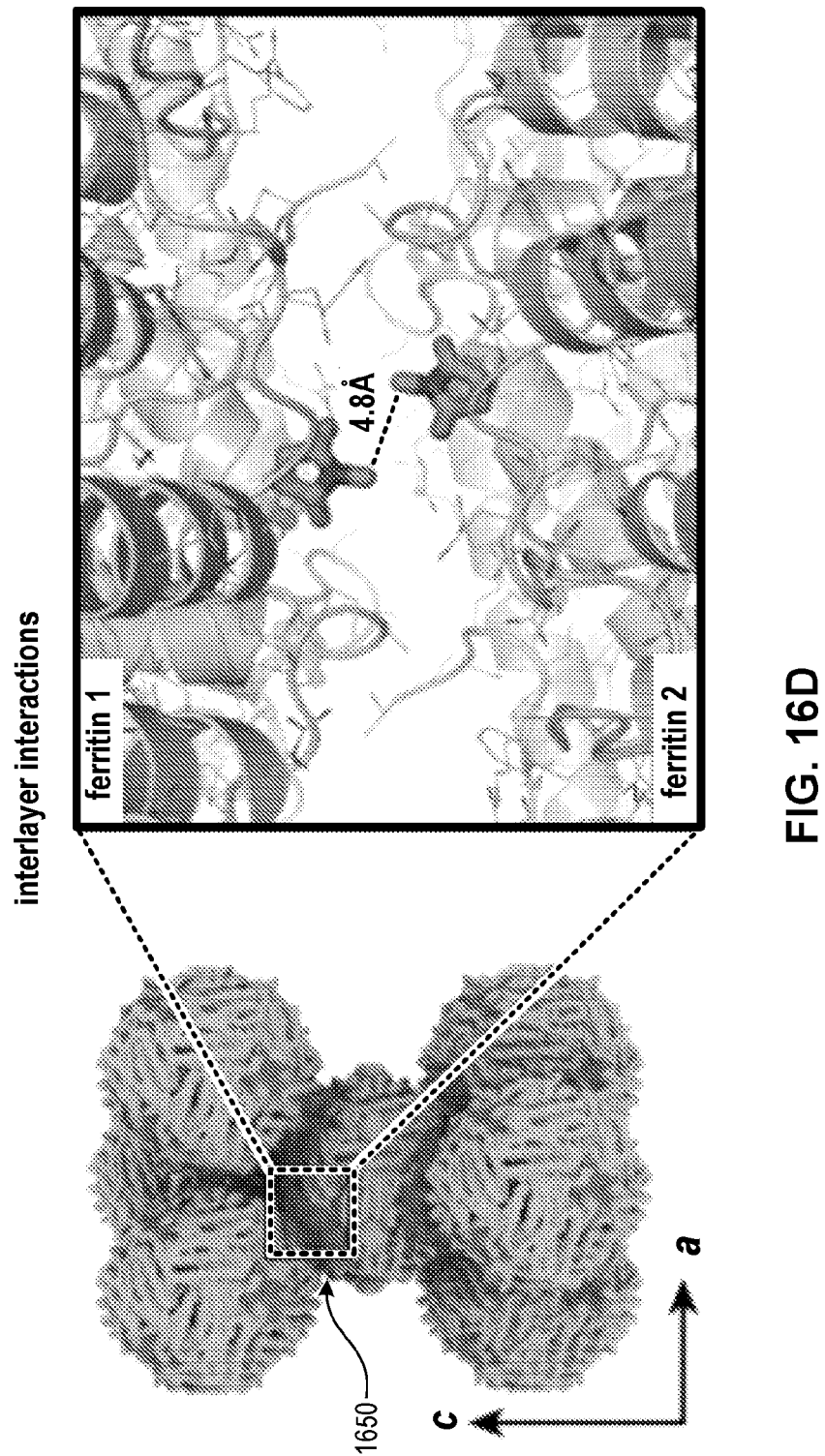
FIG. 16D shows that, in the rhombohedral crystal lattice, interlayer interactions, oriented along the c axis, are mediated by ferritin surfaces that include hydrophobic patches formed by the RAFT agents.

FIG. 16C shows that, in the rhombohedral crystal lattice, intralayer interactions between ferritin molecules in the (0001) plane oriented along the ab-plane are mediated by $Ca^{2+}$ ions (e.g., 1630, 1640 shown in FIG. 16C) and two pairs of D84 and Q86 side chains.

FIG. 16D shows that, in the rhombohedral crystal lattice, interlayer interactions, oriented along the c axis, are mediated by ferritin surfaces that include hydrophobic patches (e.g., 1650 shown in FIG. 16D) formed by the RAFT agents.

There have been extensive efforts toward designing hydrogel-based materials that display muscle-like, directional motion, and complex deformations in response to external stimuli. However, hydrogels inherently undergo isotropic volumetric changes. Therefore, multistep physical alignment/patterning strategies and external fields have to be applied to introduce anisotropic arrangements of polymer chains or embedded particles to obtain directional behavior with hydrogels. In PIX materials according to the present disclosure, the anisotropic structure of the rhombohedral $^{RAFT}$ferritin lattices and the specific positioning of the RAFT agents in these lattices create a unique opportunity to generate an anisotropic hydrogel network solely via (one-step) molecular self-assembly and also generate directional actuation.

Figure 16E:
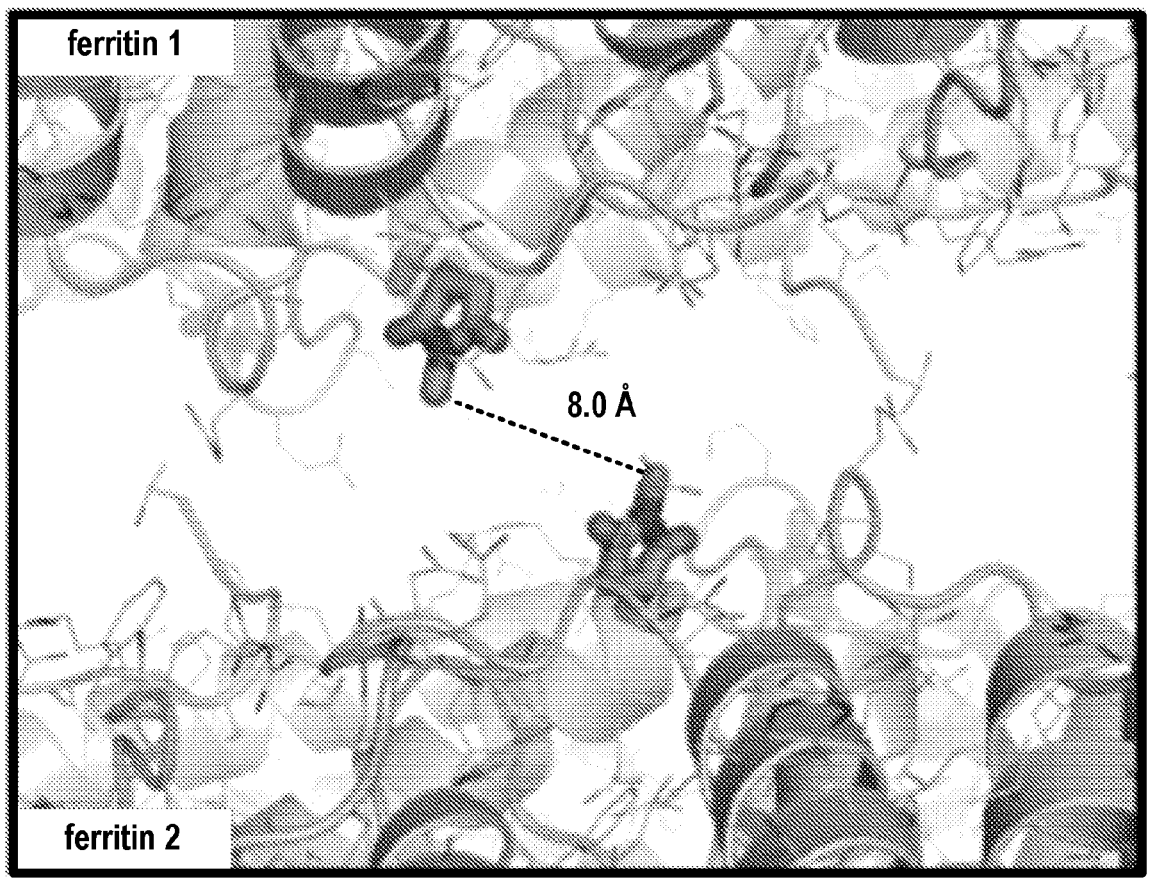
FIG. 16E shows that interlayer separation in rhombohedral $^{RAFT}$ferritin crystals according to an example embodiment increases by ca. 3 Å after acrylate infusion.

To investigate these properties, rhombohedral $^{RAFT}$ferritin crystals were first perfused with 1 M of acrylate monomers, which caused no visible loss in the integrity of the crystals. Interestingly, single-crystal X-ray diffraction (sc-XRD) measurements indicated that this treatment caused a 10-Å expansion of the lattice along the c axis whereas the a/b dimensions increased by only 2 Å (unit cell: a=b=128.9 Å, c=291.8 Å, PDB ID: 6WYH). The 2.2-Å resolution structure of the acrylate-soaked RAFT ferritin revealed a striking picture in which the neighboring hexagonal ferritin layers (i.e., the ab-planes) were separated from one another by 3-4 Å (FIG. 16E). This expansion eliminates any observable direct contact between the ferritin molecules along the c direction (and increases the interstitial solvent content of the lattice from 32% to 37%), while the $Ca^{2+}$-mediated intralayer interactions remain intact. These findings highlight the fluidity of the interlayer interactions and the anisotropy inherent in the rhombohedral crystals.

FIG. 16E shows that interlayer separation in rhombohedral $^{RAFT}$ferritin crystals according to an example embodiment increases by ca. 3 Å after acrylate infusion.

Figure 16F:
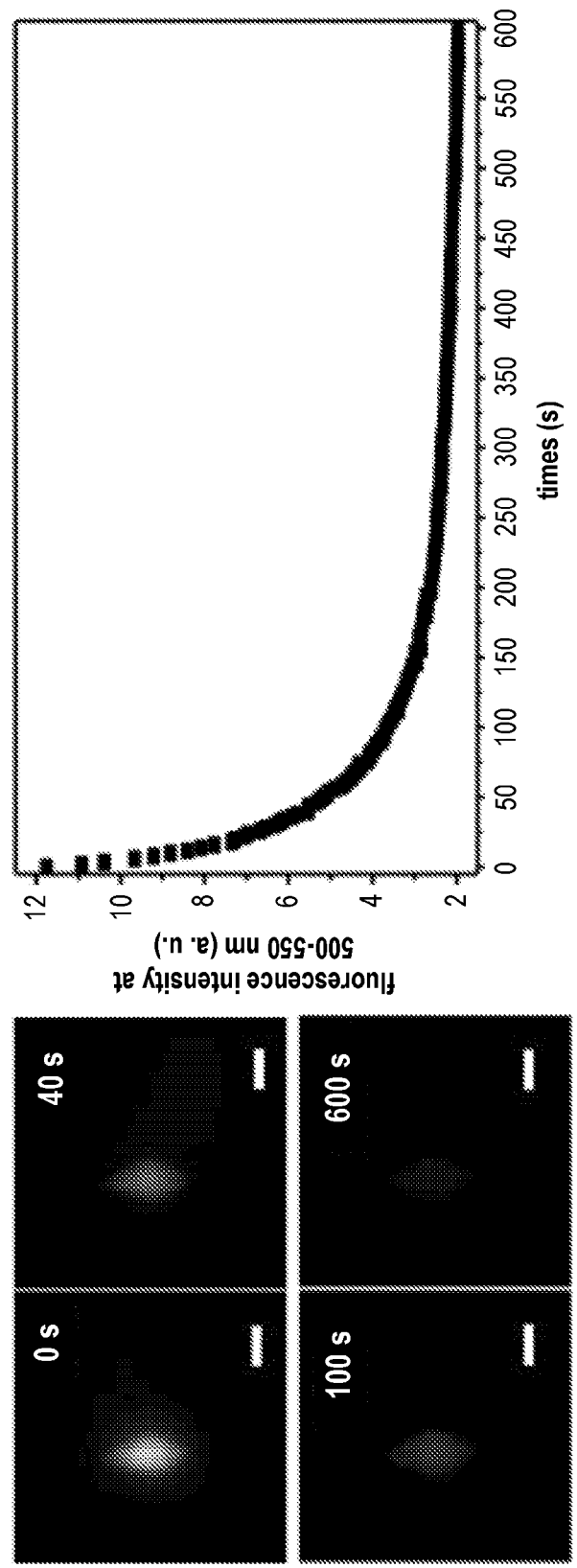
FIG. 16F illustrates formation of the polyacrylate polymer within rhombohedral $^{RAFT}$ferritin crystals according to an example embodiment.

The formation of the pA hydrogel network within $^{RAFT}$ferritin crystals was efficiently mediated by radical initiators VA-044 (0.2% w/v) or APS/TEMED (1% w/v). In crystallo polymerization was monitored by confocal microscopy, whereby we followed the quenching of the fluorescence of pyranine molecules (2max=512 nm) infused into the crystals (FIG. 16F). The process was typically complete in <2 min for a typical, 100 μm-sized crystal, but we incubated the acrylate-permeated $^{RAFT}$ferritin crystals with radical initiators for at least 5 min to ensure full hydrogel formation within the crystals. These procedures were carried out in the presence of 4 M NaCl to prevent crystal expansion during polymerization. The inclusion of chemical cross-linkers like N,N'-methylenebis(acrylamide) was unnecessary for the formation of a stable hydrogel owing to the extensive interactions between the ferritin surface and the carboxylate functional groups of pA, which yield a tightly interwoven physical network.

FIG. 16F illustrates formation of the pA within rhombohedral $^{RAFT}$ferritin crystals according to an example embodiment which was monitored by confocal fluorescence microscopy (left) through the disappearance of pyranine fluorescence, which is complete within 10 min (right, scale bars: 100 μm).

Figure 17A:
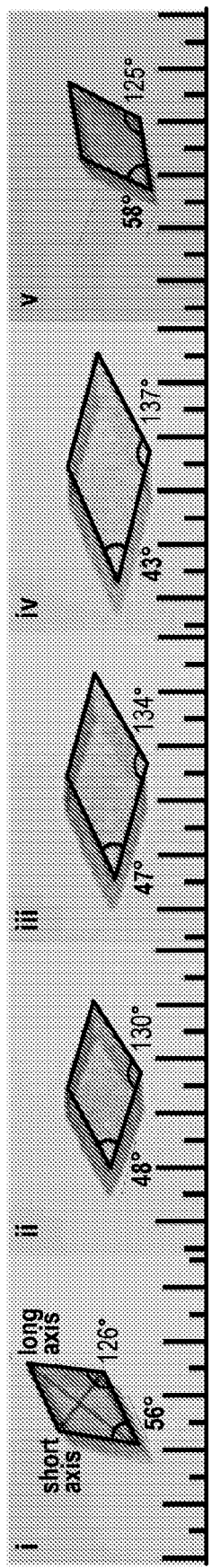
FIGS. 17A-17G illustrate anisotropic expansion and contraction behavior of rhombohedral $^{RAFT}$ferritin PIX materials according to the present disclosure.
Figure 17B:
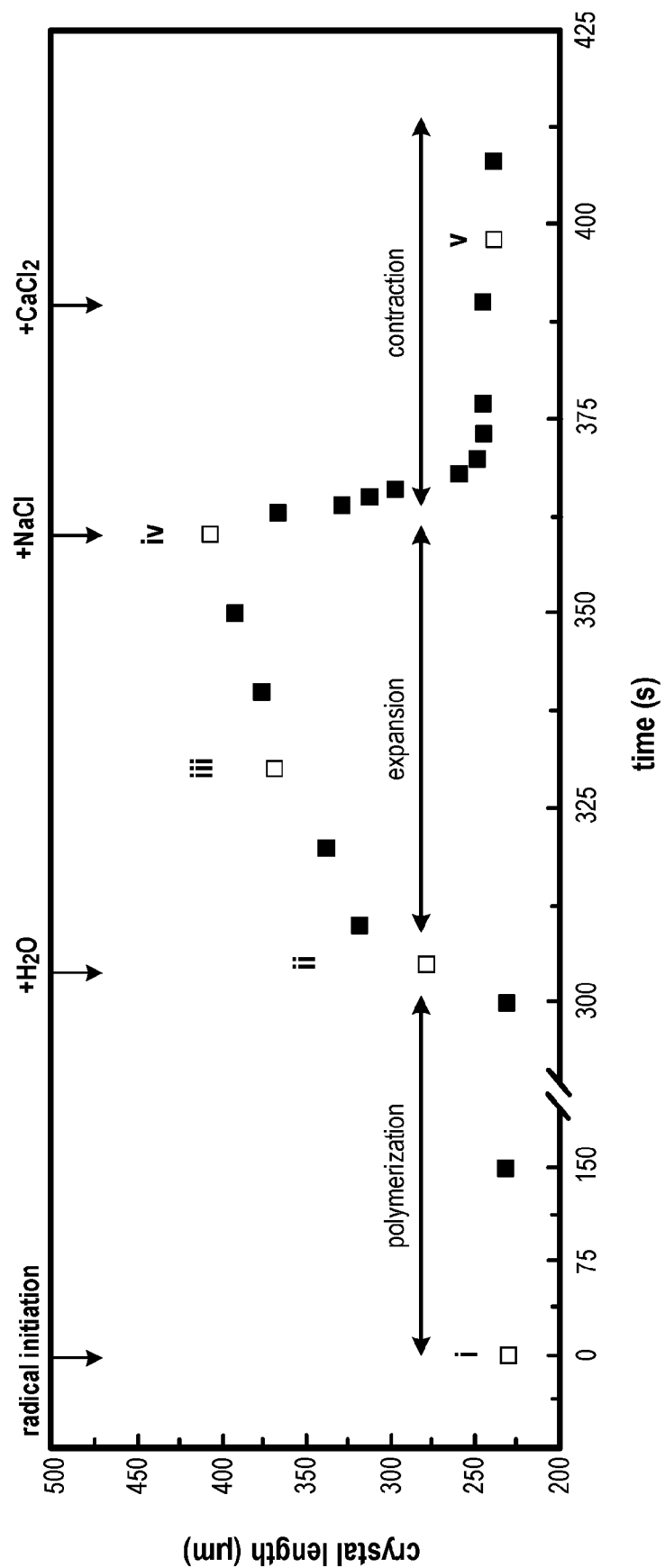
Figure 27:
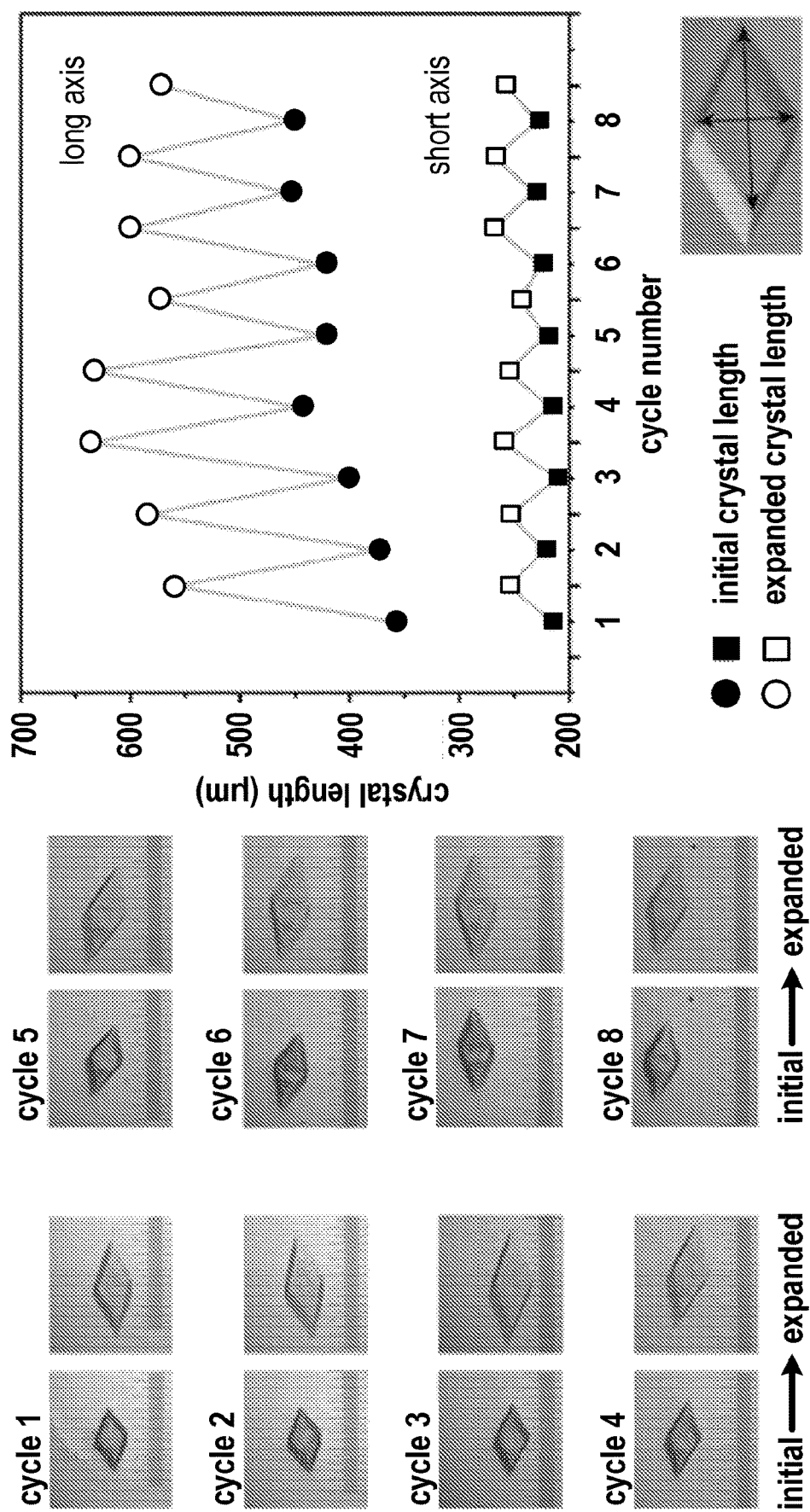
FIG. 27 illustrates successive expansion-contraction cycles of a single polymer-integrated crystal according to an example embodiment.

In an expansion experiment, the rhombohedral RAFT ferritin PIX were transferred into deionized water and monitored by light microscopy for 1-20 min (FIG. 17A). The expansion proceeded rapidly upon transfer and followed biphasic kinetics (Tfast≤10 s; Tslow >50 s), with the PIX growing to nearly 200% of their original dimensions within 1 min (FIG. 17B). When the same experiments were repeated with propionate, a nonpolymerizable acrylate analog, no expansion was observed, confirming that the pA polymer matrix was responsible for the reversible expansion of PIX. Although microcracks were sometimes visible during pA-induced expansion/contraction, the faceted crystal morphology was preserved throughout the process. Upon addition of NaCl and/or $CaCl_2$), the rhombohedral PIX contracted and regained their original dimensions within 5 s (FIGS. 17A, 17B). Roman numerals in the plot in FIG. 17B correspond to the images labeled with the same roman numerals in FIG. 17A. The expansion/contraction process was fully reversible over at least eight cycles as long as the expansion was stopped before 2 min (FIG. 27). FIG. 27 illustrates successive expansion-contraction cycles of a single rhombohedral RAFT ferritin PIX according to an example embodiment. Light micrographs of the crystal at initial and post-expansion stages in each cycle are shown on the left, and the corresponding changes in edge lengths upon expansion-contraction are shown on the right. The separation between the major ticks of the ruler is 100 μm. The long and short axes measured are indicated on an example crystal at bottom right.

Importantly, the structural dynamics of rhombohedral $^{RAFT}$ferritin PIX were highly anisotropic, as evidenced by (a) the increase in the macroscopic aspect ratio of the crystals (defined as short axis length/long axis length by over 50% after 1 min of expansion and (b) concomitant changes in the facet angles from ~56° and ~126° to ~43° and ~137°, respectively (FIG. 17A). In contrast to rhombohedral PIX, the expansion and contraction of cubic $^{RAFT}$ferritin PIX were isotropic at all times, suggesting that directional dynamics do not stem simply from RAFT-polymerization per se but likely from the higher density of the pA network in the interlayer interfaces containing the RAFT agents within the rhombohedral ferritin crystals. Indeed, upon assignment of crystal facet indices, we found that the long crystal axis, which showed disproportionate elongation compared to the short axis, aligned with the c-axis of the lattice along which the interlayer interfaces were oriented (FIG. 17C).

To elucidate lattice dynamics in molecular detail, we carried out time-dependent, small-angle X-ray scattering (SAXS) measurements on $^{RAFT}$ferritin PIX. In these experiments, in crystallo polymerization was initiated by X-ray irradiation, and the diffraction patterns of >100 PIX suspended in sample capillaries were collected. The SAXS symmetry was retained (FIGS. 17D and 17E). As in the case of light microscopy measurements, the continuous increase in anisotropy during crystal expansion was clearly evident and symmetry was retained (FIGS. 17D and 17E). As in the case of light microscopy measurements, the continuous increase in anisotropy during crystal expansion was clearly evident in the diffraction patterns. The unit cell became a=b=134.5 Å, c=383.5 Å after 1 min of expansion, corresponding to an increase in the microscopic aspect ratio (defined as c axis length/a axis length) by 25% and the cell volume by 43% (FIGS. 17E and 17F). After 5 min expansion, the long-range ferritin periodicity was still apparent from the presence of strong (003) and (101) peaks, which yield a unit cell of a=b=147.4 Å, c=436.9 Å (FIGS. 17D and 17E). These values correspond to increases in the cell aspect ratio and volume by 31% and 96%, respectively, compared to unexpanded crystals (FIGS. 17F and 17G). Consistent with light microscopy measurements, the kinetics for the growth of unit cell dimensions and the increase in longitudinal anisotropy was also nonmonotonic (FIGS. 17E and 17F). We attribute this behavior to a fast initial expansion of the dense pA network throughout the PIX, which attenuates as the overall polymer density decreases and polymer chain mobility increases. Time-dependent SAXS measurements were repeated for cubic $^{RAFT}$ferritin PIX, which confirmed that the cubic symmetry-thus the 3D isotropy—was retained throughout expansion.

Figure 17C:
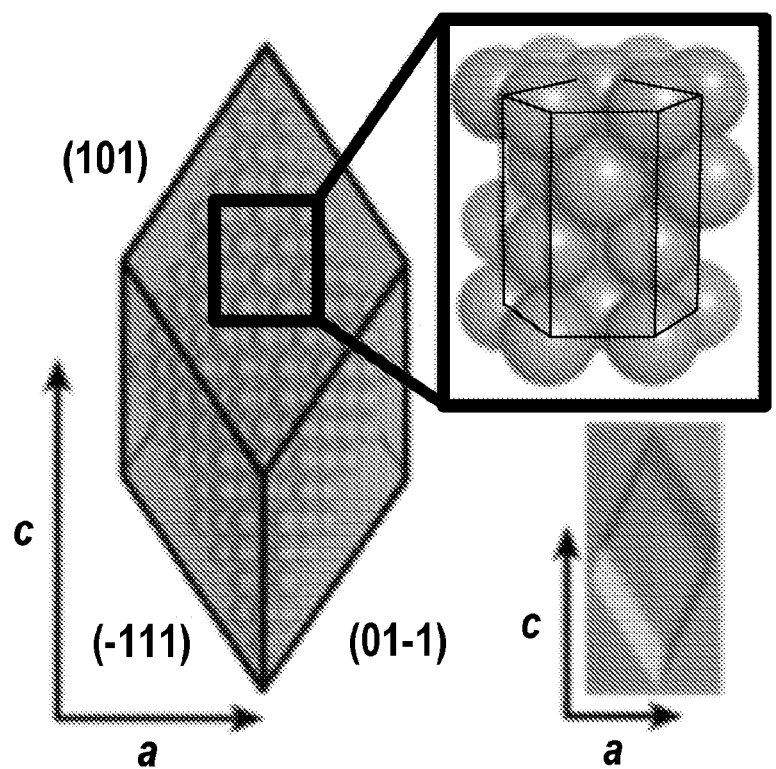
Figure 17D:
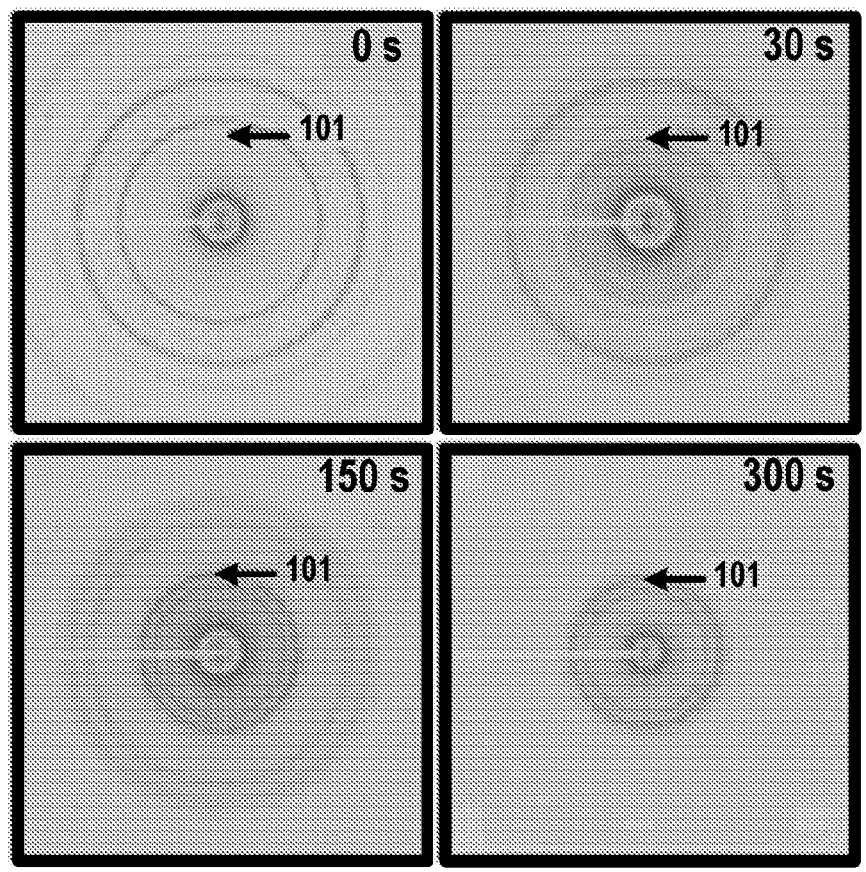
Figure 17E:
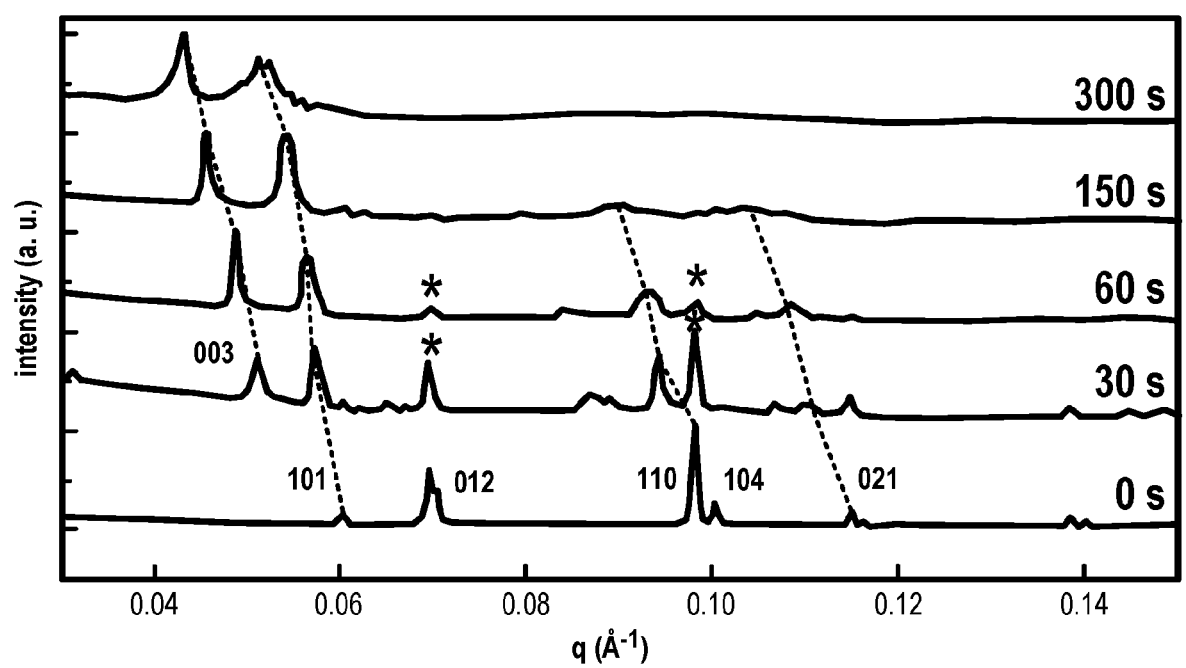
Figure 17F:
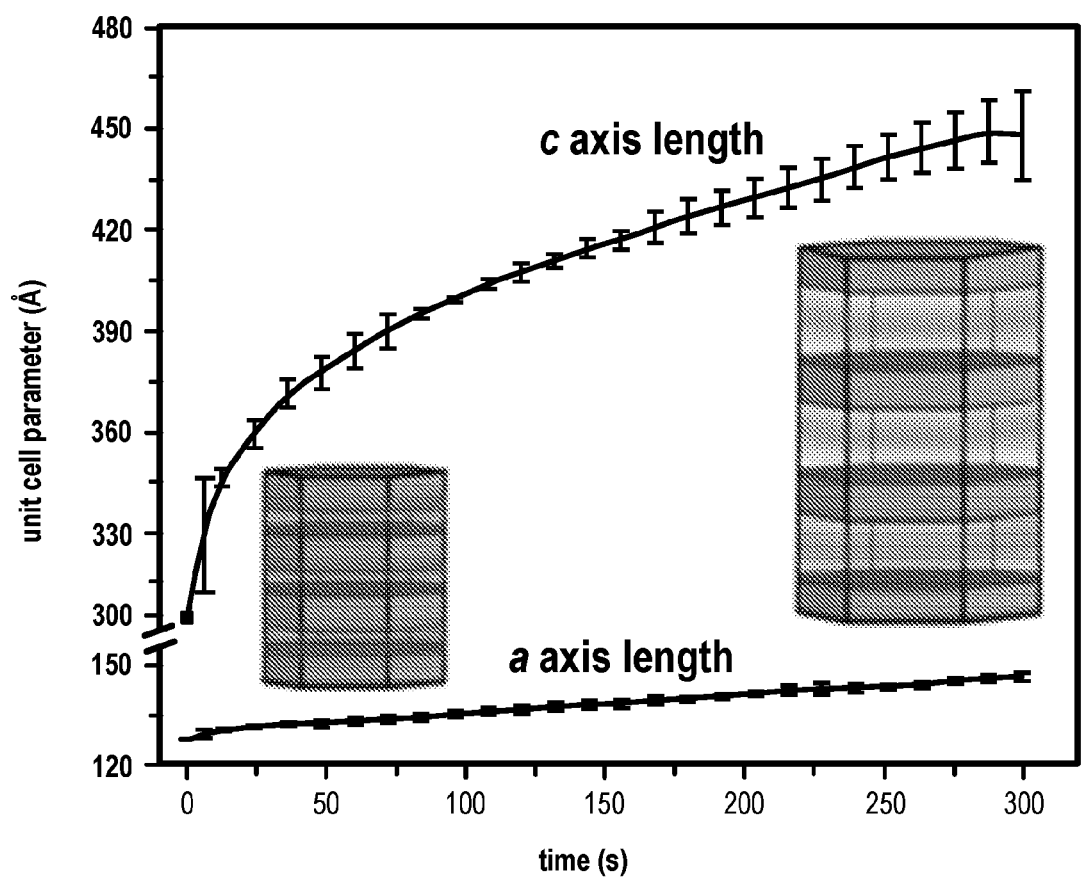
Figure 17G:
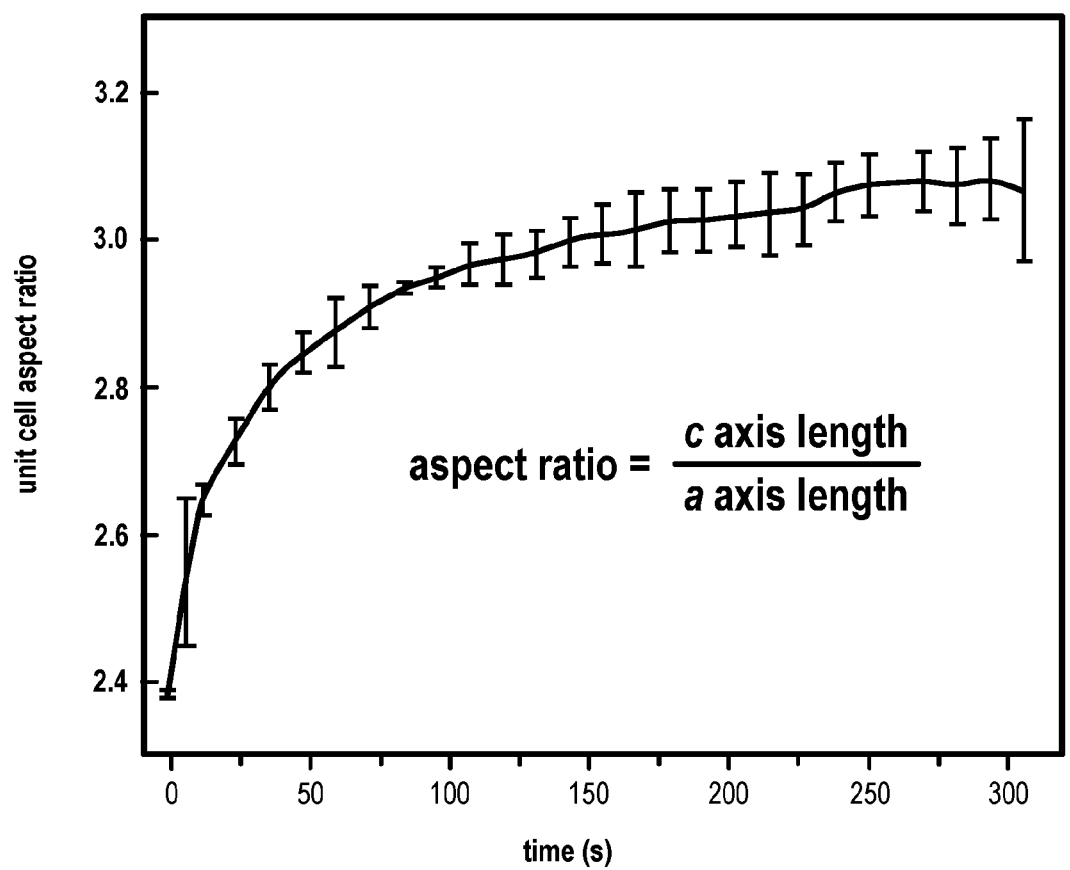

FIGS. 17A-17G illustrate anisotropic expansion and contraction behavior of rhombohedral $^{RAFT}$ferritin PIX materials according to the present disclosure. FIG. 17A illustrates monitoring of the anisotropic expansion and contraction of a single rhombohedral RAFT ferritin PIX by light microscopy. The separation between the major ticks of the ruler is 100 μm. FIG. 17B shows the corresponding changes in long-axis length of the same $^{RAFT}$ferritin PIX during polymerization, expansion, and contraction. FIG. 17C shows facet indices and lattice orientation in rhombohedral crystal of RAFT ferritin PIX material according to an example embodiment. FIG. 17D shows SAXS images collected at different time points during the expansion of rhombohedral $^{RAFT}$ferritin PIX and FIG. 17E shows the corresponding 1D SAXS profiles. The progression of peaks to lower angles (due to expansion of the unit cell) is indicated with black dashed lines. Peaks corresponding to the original lattice (due to unexpanded crystals) are visible throughout the process and designated with blue asterisks. FIG. 17F illustrates changes in the unit cell dimensions of rhombohedral PIX during expansion, calculated from the SAXS profiles shown in FIG. 17E. FIG. 17G shows changes in the aspect ratio (i.e., the anisotropy) of the unit cell of rhombohedral PIX during expansion. Error bars: standard deviation of triplicate measurements.

Figure 18A:
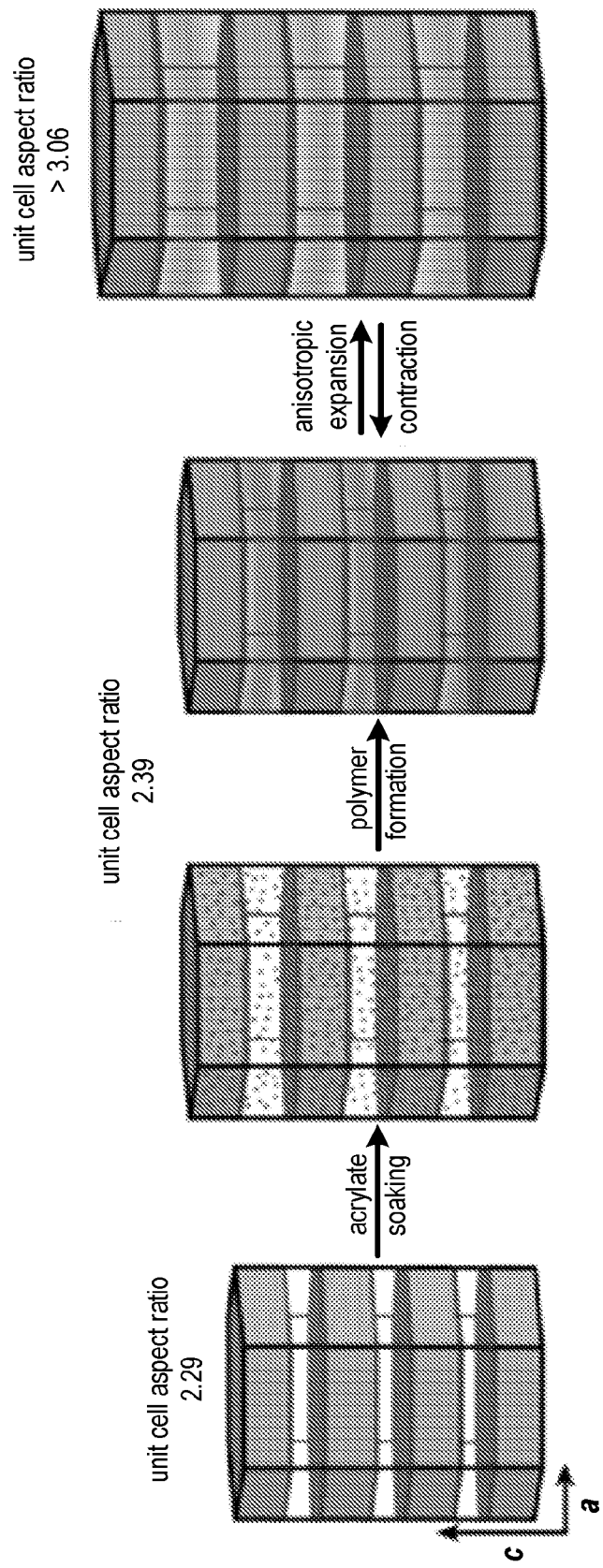
FIGS. 18A and 18B illustrate that anisotropic expansion/contraction of rhombohedral RAFT ferritin PIX materials according to the present disclosure is enabled by the anisotropic polymer matrix and is fully reversible.

Anisotropic distribution of the pA polymer matrix within rhombohedral RAFT ferritin crystals of PIX materials according to the present disclosure, can be attributed to a combination of two factors: (1) the specific interlayer positions of the RAFT agents which promote localized polymer growth and (2) the wide, weakly bound interlayer interfaces, which are further enlarged upon soaking with acrylate monomers. Both factors would lead to the interlayer zones developing a denser matrix of pA polymer compared to the tighter interfaces along the ab-planes, thus generating a lamellar pattern (FIG. 18A). Consequently, the hydration of the PIX produces a larger extent of lattice expansion parallel to the c-axis compared to that in the ab-plane (FIG. 18A). Although the pA network may display varying densities, it is continuous throughout the mesoporous lattice and forms extensive interactions with the ferritin molecules. The resulting dense mold thus allows the expanded ferritin lattice to fully revert to its original dimensions upon NaCl/CaCl$_2$)-induced dehydration. In fact, the sc-XRD measurements show that $^{RAFT}$ferritin PIX materials according to the disclosed technology fully regain their near-atomic-level crystallinity upon contraction after 5 min of expansion (FIG. 18B), meaning that ferritin molecules can return to their original lattice positions and orientations after having separated from one another by >20 Å in the ab-plane and >40 Å along the c-axis.

Figure 18B:
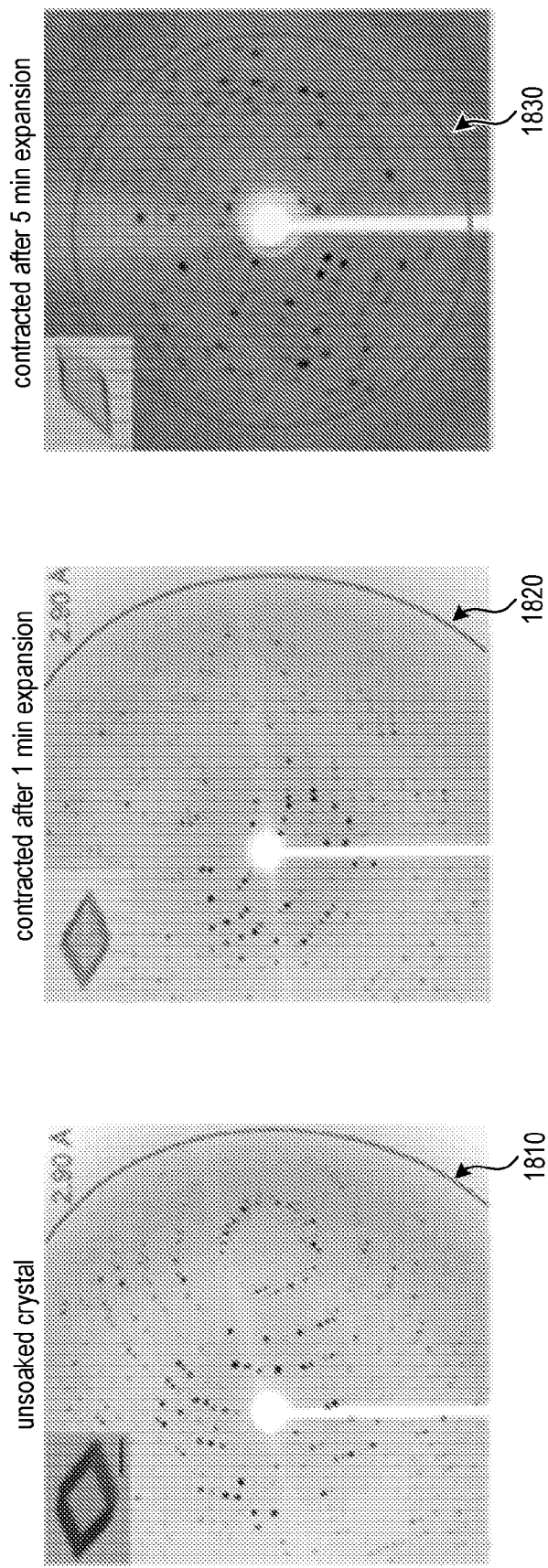

FIGS. 18A and 18B illustrate that anisotropic expansion/contraction of rhombohedral RAFT ferritin PIX materials according to the present disclosure is enabled by the anisotropic polymer matrix and is fully reversible. FIG. 18A shows a schematic summary for the generation of the anisotropic/layered pA network within rhombohedral $^{RAFT}$ferritin crystals, which dictates the anisotropic structural dynamics. FIG. 18B shows sc-XRD image (at T=298 K) of native rhombohedral $^{RAFT}$ferritin crystal (left), compared to those of a PIX contracted after 1 min of expansion (middle), and after 5 min of expansion (right). The diffraction limits are indicated with circles 1810, 1820, and 1830. Light micrographs of the crystals are shown in the insets; the scale bar and separation between the major ticks of the ruler are 100 μm.

To examine the link between the anisotropic pA distribution in RAFT ferritin PIX and localized polymer growth originating from the RAFT agents on ferritin surfaces, the $^{RAFT}$ferritin PIX were dissolved by treatment with ethylenediaminetetraacetic acid (EDTA) and analyzed by SDS-PAGE and GPC. Interestingly, these $^{RAFT}$ferritin PIX samples showed no evidence of covalent attachment between pA chains and ferritin molecules when in crystallo polymerization was induced with APS/TEMED and only minimal yields of graft-from polymerization when VA-044 was used as a radical initiator. The drastically diminished graft-from polymerization efficiencies are likely due to the steric occlusion of the RAFT agents within the interlayer interfaces and slower molecular diffusion within the crystals. These observations implied that the inherent anisotropy of the rhombohedral crystals was alone responsible for templating an anisotropic hydrogel network in ferritin PIX.

Figures 19A, 19B:
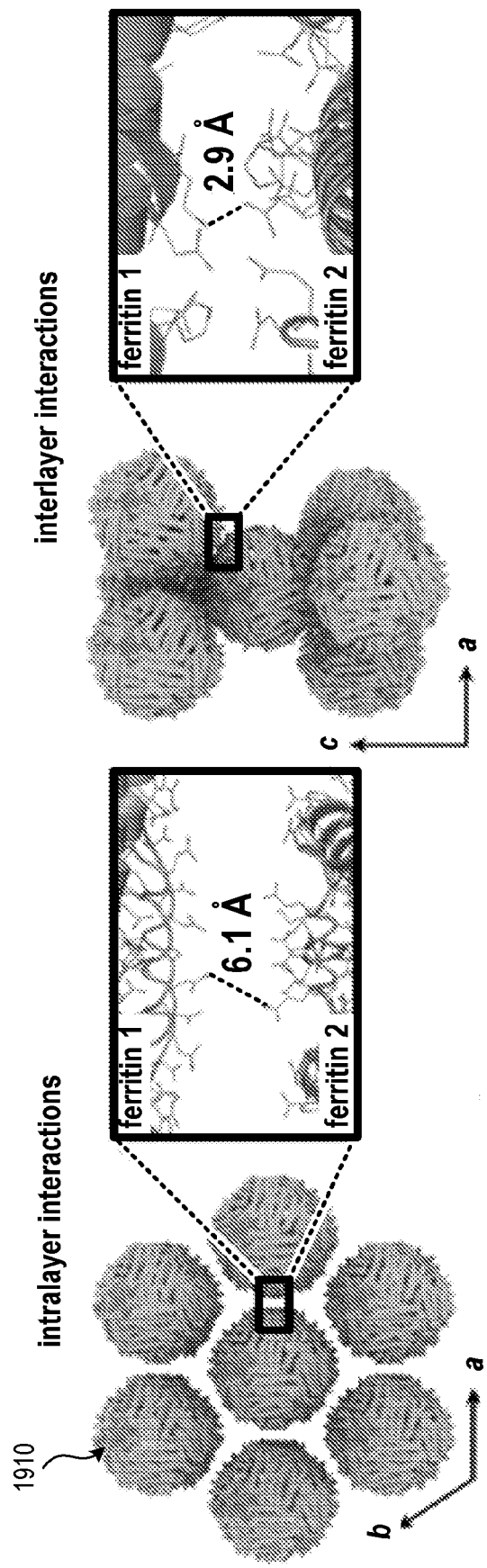
FIGS. 19A-19E show structural properties and anisotropy of $^{AC}$ferritin crystals and PIX materials with P3/21 symmetry according to the present disclosure.

An appropriate control system to test this possibility would be ferritin crystals that are also rhombohedral but lack covalently attached RAFT agents. Since the RAFT agents are directly involved in lattice packing interactions, we were not able to obtain isomorphous rhombohedral crystals using unmodified $^{C157}$ferritin. Yet, in the course of exhaustive screening, we found that a ferritin variant lacking Cys157 (termed ΔC) formed lattices with trigonal symmetry (P3:21; a=b =131.8 Å, c=301.8 Å, PDB ID: 7K26) and a rhombohedron-shaped crystal habit that is nearly identical to that of rhombohedral (i.e., H32-symmetric) $^{RAFT}$ferritin crystals. The 2.7-Å resolution structure of the trigonal crystals indeed revealed a similar hexagonal-layered packing arrangement with an interstitial solvent content of 44.5% but also indicated that the protein interfaces in these lattices substantially differ from those in their rhombohedral counterpart. Notably, the lattice packing interactions between ferritin molecules are mediated entirely by the interlayer interfaces directed along the c axis, whereas the intralayer interfaces in the ab-plane are ca. 6 Å wide at their narrowest point and devoid of direct ferritin-ferritin contacts (FIGS. 19A and 19B). Thus, in terms of the orientation of interstitial voids that can be filled with the pA matrix, the trigonal and rhombohedral lattices are orthogonal to one another.

Figure 19D:
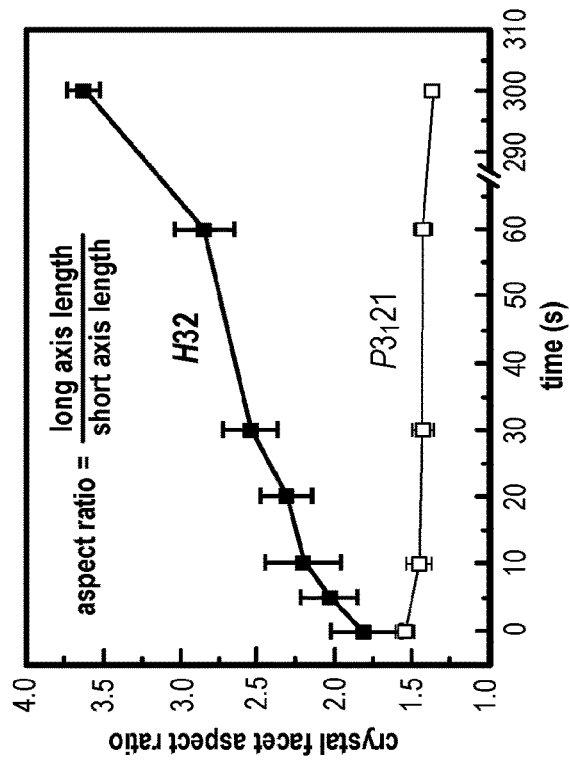
Figure 19E:
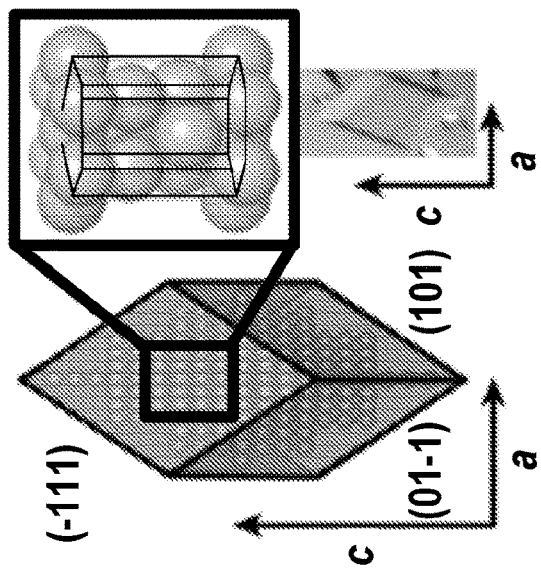
Figure 19C:
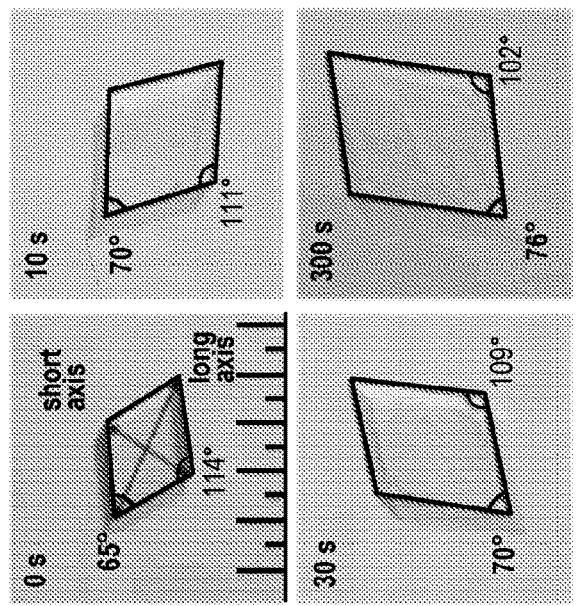

Despite the relative mechanical fragility of the trigonal crystals, pA matrices can be formed within them. The expansion/contraction properties of the resulting PIX were examined by light microscopy, which revealed that they also displayed anisotropic dynamics, but the direction of crystal expansion was orthogonal to that observed with rhombohedral RAFT ferritin PIX (FIGS. 19C and 19E). Whereas the rhombohedral PIX elongated to assume a lozenge shape (with the acute facet angles decreasing from ~60° to ~45°, FIG. 17A) upon expansion, the trigonal PIX expanded toward a more square-like shape (with the acute facet angles increasing from ~60° to 76°, FIG. 19C), with the overall aspect ratios of the two systems moving in opposite directions (FIG. 19D). These findings establish that 1) the anisotropy of the crystal lattices and the underlying orientation/structure of the protein-protein interfaces alone are sufficient for the formation of anisotropic hydrogel networks within PIX, and 2) they can be used to control the directionality of PIX dynamics.

FIGS. 19A-19E show structural properties and anisotropy of $^{ΔC}$ferritin crystals and PIX materials with P3:21 symmetry according to the present disclosure. FIG. 19A shows that $^{ΔC}$ferritin molecules along the ab-plane are devoid of any intralayer interactions. The closest side chains, Q86 and D84, are 6.1 A apart which precludes any salt-bridge interactions. FIG. 19B shows that interlayer interactions, oriented along the c axis, are mediated by surfaces that include hydrophobic patches. The closest noncovalent interaction is within 3.0 Å and formed by side chains K119 and E116.

Where the H32 lattice hydrophobic patches would be are highlighted in dark gray (e.g., 1910 in FIG. 19A). FIG. 19C shows light micrographs of P3121 symmetric PIX during expansion in water. The separation between the major ticks of the ruler is 100 µm. FIG. 19D shows that changes in the crystal facet aspect ratios of P3121 and H32 symmetric PIX during expansion display their respective anisotropic behavior. Error bars: standard deviation of triplicate measurements. FIG. 19E shows facet indices and lattice orientation in trigonal $^{AC}$ferritin PIX.

Figure 20A:
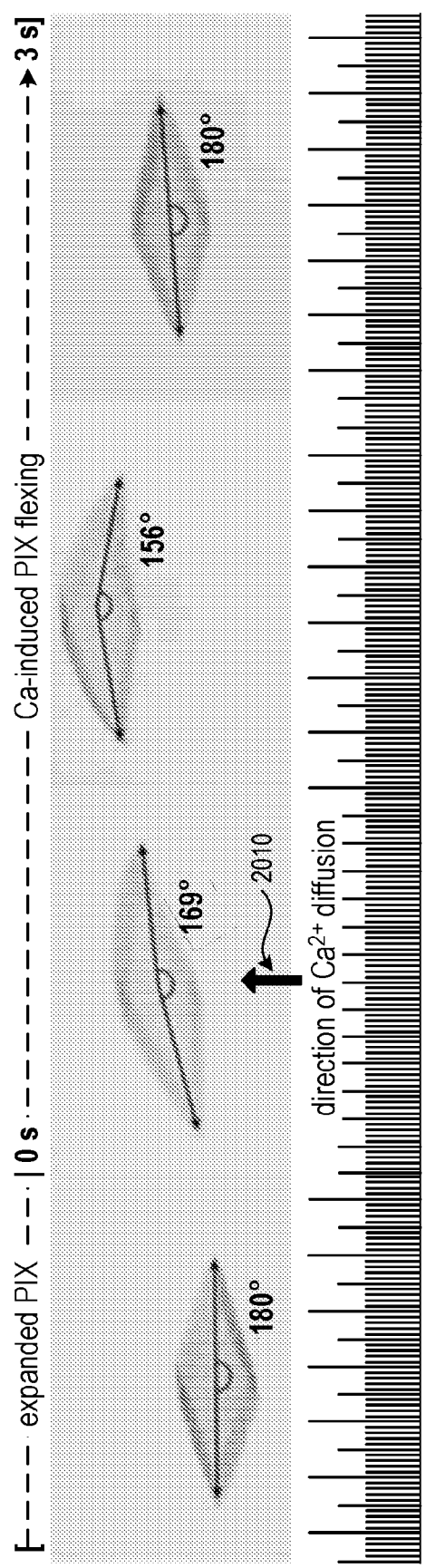
FIGS. 20A-20D show anisotropic mechanical and self-healing behavior of rhombohedral RAFT ferritin PIX materials according to the disclosed technology.
Figure 20B:
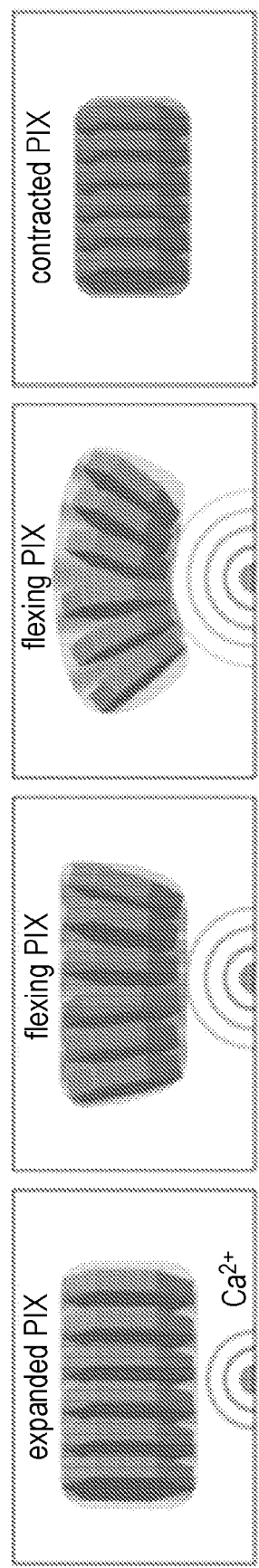

Rhombohedral $^{RAFT}$ferritin PIX materials according to the present disclosure exhibit anisotropic mechanical and self-healing properties. Analogous to the mechanical anisotropy of muscles enabled by their underlying anisotropic architecture, the directional alignment of polymer chains or embedded particles within hydrogels can yield anisotropic mechanical properties with respect to the direction of applied force and generate bending motions. This behavior was also borne out in expanded rhombohedral RAFT ferritin PIX according to the disclosed technology, which possess an alternating pattern of high- and low-molecular density regions aligned along the c-axis (FIGS. 20A-20D). When the expanded PIX were exposed to $Ca^{2+}$ ions to induce contraction, they underwent a drastic bending motion toward the direction of $Ca^{2+}$influx, with flexion angles of up ~25° in the absence of any apparent cracking. The PIX reverted to the original shape as the $Ca^{2+}$flux dissipated (FIG. 20A). The bending of the PIX arises from the compression of the hydrogel matrix perpendicular to the hexagonal ferritin ab-layers at the $Ca^{2+}$diffusion front and provides, in essence, a chemosensory/chemotactic motion (FIG. 20B). The actuation is remarkably rapid with a bending rate of $>10°$ $s^{-1}$, which is one-to-several orders of magnitude higher than those of recently reported supramolecular and hydrogel systems with some of the fastest reported actuation rates (1.5° $s^{-1}$ and 0.14° min-1, respectively). The rapid actuation by the PIX can be ascribed to the high packing density and the structural cooperativity of the integrated crystal-pA matrix.

Figure 20C:
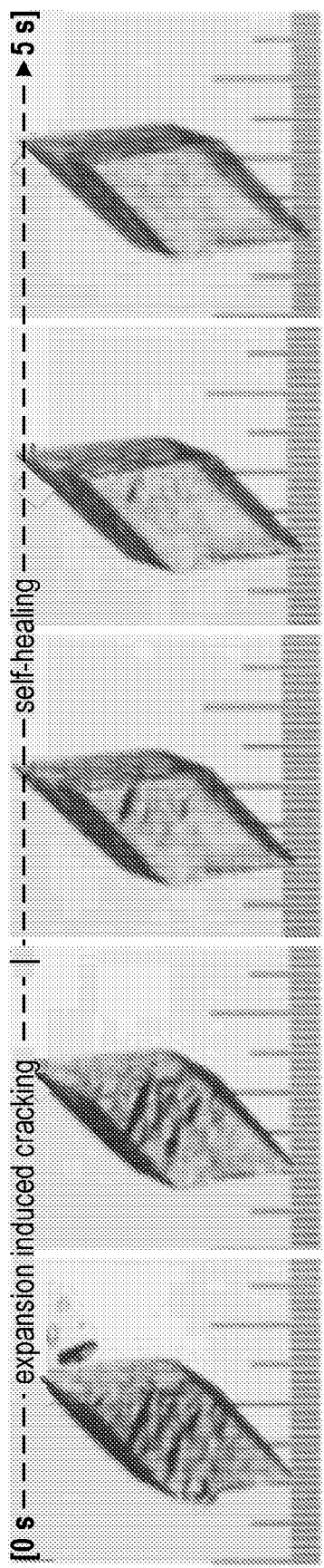

Under certain circumstances like excessive bending or fast expansion/contraction, the rhombohedral $^{RAFT}$ferritin PIX were observed to develop large fractures, sometimes >75 µm in length and >10 µm in width (FIG. 20C). Consistent with the mechanical anisotropy of these materials, the defects were overwhelmingly oriented along the short crystal axis (i.e., parallel to the hexagonal ferritin layers in the ab-planes) (FIG. 20C). Owing to the mobility of the hydrogel matrix and its reversible interactions with the ferritin molecules, these large defects were often scarlessly and autonomously healed. In extreme cases, such as that shown in FIG. 20D, the rhombohedral PIX could even undergo near-complete lamellar fracturing and accordion-like motions to adapt to $Ca^{2+}$fluxes in solution, followed by full recovery of their original polyhedral morphology within seconds. Such rapid, adaptive motions with attendant self-healing are more typical of soft biological devices like muscles rather than stiff molecular crystals.

Figure 20D:
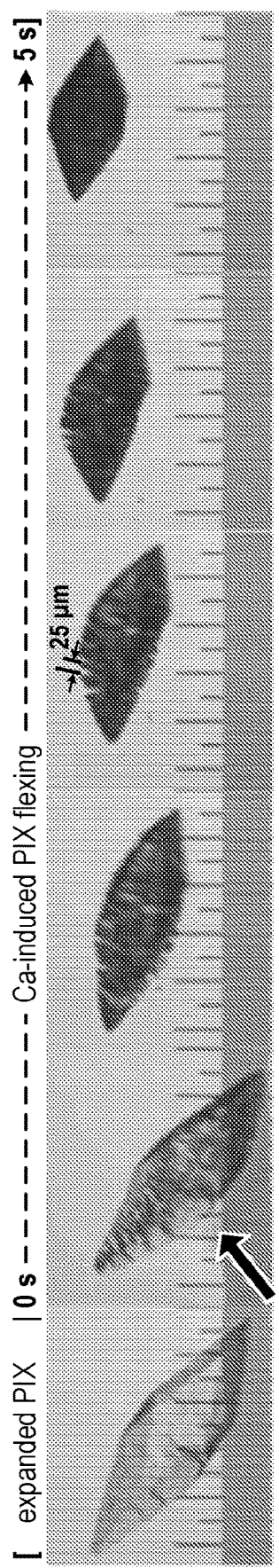

FIGS. 20A-20D show anisotropic mechanical and self-healing behavior of rhombohedral $^{RAFT}$ferritin PIX materials according to the disclosed technology. FIG. 20A shows light micrographs showing the bending motion of an expanded RAFT ferritin PIX flexing in response to $Ca^{2+}$flux (oriented along the arrow 2010). The separation between the major ticks of the ruler in all images is 100 µm. FIG. 20B shows schematic description for the cation-induced reversible bending motion of the rhombohedral $^{RAFT}$ferritin PIX due to the underlying hexagonal-layered lattice arrangement and the anisotropic distribution of the polymer network. FIG. 20C shows defects in rhombohedral RAFT ferritin PIX are overwhelmingly oriented in the direction of the ab-planes (orthogonal to the long crystal axis) and often spontaneously healed. FIG. 20D shows that $^{RAFT}$ferritin PIX can undergo substantial lamellar fracturing and accordion-like flexing motions in response to $Ca^{2+}$flux.

The disclosed techniques utilize PIX materials, which seamlessly combine the structural order and periodicity of crystals with the adaptive and tunable mechanical properties of polymeric networks, as a method to capture and release cargo. These materials have several unique properties discussed above. Through the physical integration of two disparate classes of materials, i.e., molecular crystals and hydrogel polymers, we can obtain an unprecedented combination of material attributes and mechanical behaviors: atomic-level order/coherence, directional motion, flexibility, rapid anisotropic actuation, chemical responsiveness, self-healing.

Key to the attainment of anisotropic properties in PIX materials according to the present disclosure is the ability of ferritin molecules to form lattices with distinct symmetries and protein-protein interfaces. These differences allowed the temptation of alternatively patterned hydrogel networks in situ, which ultimately enabled ferritin crystals that essentially possess the same macroscopic morphologies to display orthogonally directed motions. Control over the spatial distribution of polymer networks within protein crystals can be achieved using site-directed RAFT-polymerization strategies according to the present disclosure. Such strategies can offer important advantages such as the incorporation of polymers with a diverse range of functional groups into protein lattices (regardless of their chemical compatibility with the protein components), construction of multipolymer networks, and spatiotemporal control over polymer growth within lattices. Combined with the inherent chemical versatility and functions of proteins, covalently hybridized PIX materials according to the technology disclosed herein can offer, among other features and benefits, a unique platform for the study of protein-polymer interactions and the development of biocatalytic and molecular encapsulation/delivery systems with tunable and responsive mechanical properties.

The following techniques, procedures and methods were used to produce and characterize PIX materials according to the disclosed technology.

All reagents were purchased from commercial sources and used without further purification unless noted otherwise. Mass spectrometry (MS) of proteins and small molecules was carried out using electrospray ionization (ESI) on a Micromass Quattro Ultima Triple Quadrupole MS. NMR spectra were recorded on Varian Mercury (400 MHZ) and Bruker AVA (300 MHZ) spectrometers. NMR data are reported as follows: chemical shift, multiplicity (s=singlet, d=doublet, t=triplet, m=multiplet, dd=double doublets), and relative integrated peak area. The spectra were internally referenced to the residual solvent signal (DMSO, δ2.50 ppm).

The plasmid for the AC variant of human heavy-chain ferritin, devoid of all native cysteine residues (C90E, C102A, and C130A), was obtained via site-directed mutagenesis. C157 ferritin was prepared using QuikChange mutagenesis with primers obtained from Integrated DNA Technologies shown in Table 1. Mutant plasmids were transformed into XL-1 blue *E. coli* cells and purified with QIAprep Spin Miniprep kit (Qiagen). The variant was sequenced (Retrogen) to verify mutagenesis. When handling $^{C157}$ferritin, 2 mM DTT was added at each step during purification to prevent disulfide-mediated protein aggregation.

TABLE 1

Primers for site-directed mutagenesis.
(SEQ ID NOS: 1 and 2)

| Variant | Mutation | Primer Sequence |
|---|---|---|
| 157C ΔC | K157C | 5'-CCAACCTGCGTTGCATGGGTGCACC-3' 5'-GGTGCACCCATGCAACGCAGGTTGG-3' |

Figure 21:
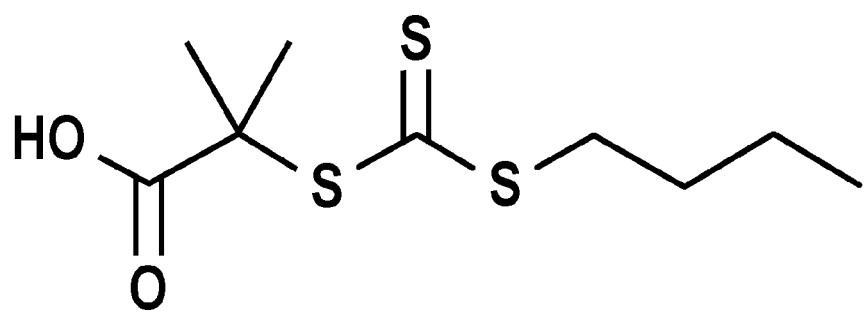
FIG. 21 shows an example structure of a 2-(((butylthio)carbonothioyl)thio)-2-methylpropanoic acid molecule.

To synthesize 2-(((butylthio)carbonothioyl)thio)-2-methylpropanoic acid (R1 in FIG. 25), tribasic potassium phosphate (22.88 g, 108 mmol) was dissolved in acetone (180 mL) and stirred for 5 h. 1-butanethiol (11.61 mL, 108 mmol) was added, and the solution was stirred for 1 h. The reaction was cooled to 0° C., and carbon disulfide (7.82 mL, 129 mmol) was added dropwise over 5 min. The combined solution was stirred for 2 h, followed by the addition of 2-bromo-2 methylpropionic acid (18 g, 108 mol). After stirring for 12 h, the solution was filtered, and the filtrate was concentrated in vacuo. A solution containing 10% HCl (200 mL) was added, and the reaction was stirred for 12 h. The product was extracted 2× with hexanes (50 mL), the organic layer was dried over anhydrous sodium sulfate, and the solvent was removed in vacuo. The solid was purified by silica gel chromatography with a gradient of 20-50% ethyl acetate in hexanes. The solvent was removed in vacuo, and the precipitate was dissolved in a minimal amount of hexanes. The resulting solution was cooled to −20° C., and crystals formed overnight. The crystals were filtered and dried in vacuo, yielding 20 g of product (74%). 1H NMR (400 MHZ, DMSO-d6): δ3.30 (t, J=7.3 Hz, 2H), 1.68-1.54 (m, 8H), 1.35 (m, J=15.0, 7.3 Hz, 2H), 0.87 (t, J=7.3 Hz, 3H). Measured molecular weight: (m/z)=253.15 m/z (Calculated: 253.03) (M+H+). FIG. 21 shows an example structure of a 2-(((butylthio)carbonothioyl)thio)-2-methylpropanoic acid molecule.

Figure 22:
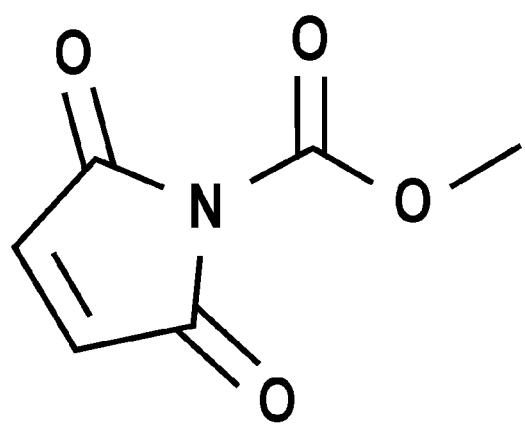
FIG. 22 shows an example structure of a N-(Methoxycarbonyl)maleimide molecule.

To synthesize N-(Methoxycarbonyl)maleimide (NMCM in FIG. 25), maleimide (388 mg, 4 mmol) and N-methylmorpholine (439 μL, 4 mmol) were dissolved in ethyl acetate (20 mL), cooled to 0° C., and stirred. Methylchloroformate (310 μL, 4 mmol) was added dropwise to the solution while stirring. After 30 min, the mixture was filtered, and the precipitants were washed with 10 mL ethyl acetate. The filtrate was collected, washed with 5 mL brine, dried over anhydrous sodium sulfate, and the remaining solvent was removed in vacuo, yielding 517 mg (83%). 1H NMR (300 MHz, DMSO): δ 7.17 (s, 2H), 3.83 (s, 3H). Measured molecular weight: (m/z)=156.03 m/z (Calculated: 156.11) (M+H+). FIG. 22 shows an example structure of a N-(Methoxycarbonyl)maleimide molecule.

Figure 23:
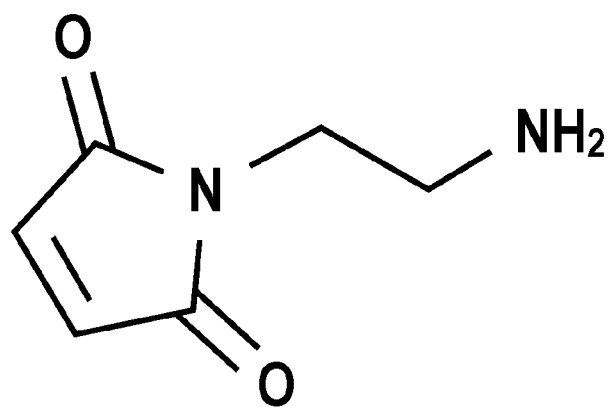
FIG. 23 shows an example structure of a N-(2-aminoethyl)-maleimide molecule.

To synthesize N-(2-aminoethyl)-maleimide (FIGS. 23 and 25), methyl 2,5-dioxo-2,5-dihydro-1H-pyrrole-1-carboxylate (6.43 g, 41.5 mmol) was dissolved in saturated NaHCO$_3$ (50 mL) and combined with a solution containing tert-butyl (2-aminoethyl) carbamate (6.56 mL, 41.5 mmol) in saturated NaHCO$_3$ (50 mL). The combined solution was stirred for 40 min at 0° C. and 50 min at room temperature. The reaction was again cooled to 0° C., and the pH was adjusted to ca. 3 with concentrated H2SO4. The solution was extracted 3× with ethyl acetate (20 ml), and the organic layer was dried over anhydrous sodium sulfate concentrated to a brown oil in vacuo. This oil was purified by silica gel chromatography (eluted with 50% ethyl acetate in hexanes). The flow-through was concentrated in vacuo yielding a white powder. The powder was dissolved in 50 mL dichloromethane and cooled to 0° C. Trifluoroacetic acid (50 mL) was added to the solution. The solution was stirred for 1 h at 0° C. and concentrated in vacuo. Chilled diethyl ether was added to the concentrated solution to precipitate out N-(2-aminoethyl)-maleimide as a white solid. The precipitate was filtered, washed with diethyl ether, and dried in vacuo, yielding 4.92 g of product (75%). 1H NMR (400 MHZ, DMSO-d6): δ 8.02 (s, 3H), 7.06 (s, 2H), 3.65 (t, J=5.8 Hz, 2H), 2.99 (t, J=5.8 Hz, 2H). Measured molecular weight: (m/z)=141.07 m/z (Calculated: 141.06) (M+H+). FIG. 23 shows an example structure of a N-(2-aminoethyl)-maleimide molecule.

Figure 24:
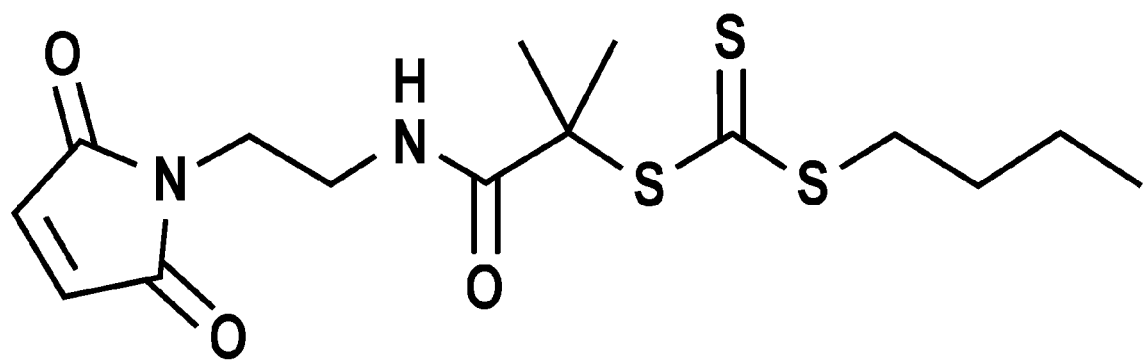
FIG. 24 shows an example structure of a maleimide-functionalized RAFT agent (R2) molecule.

To synthesize the maleimide-functionalized RAFT agent (R2 in FIG. 25), N-(2-aminoethyl)-maleimide (7.14 mmol, 1 g), HATU (7.78 mmol, 2.96 g), and DIPEA (19.46 mmol, 3.39 mL) was dissolved in dimethylformamide (30 mL) and stirred for 10 min. 2-(((butylthio)carbonothioyl)thio)-2-methylpropanoic acid (6.49 mmol, 1.637 g) was added in portions over 5 min, and the reaction was stirred for 12 h. Water (30 mL) was added, and the solution was extracted 3× with 20 mL of ethyl acetate. The organic layer was collected, dried over anhydrous sodium sulfate, and concentrated in vacuo. The product was purified by silica gel chromatography with 20-40% ethyl acetate in hexanes as the eluent. The solvent was removed in vacuo and dissolved in a minimal amount of hexanes. The resulting solution was cooled to −20° C., and crystals formed overnight. The crystals were filtered and dried in vacuo, yielding 2.10 g of product (86%). 1H NMR (300 MHz, DMSO-d6): δ 8.04 (t, J=5.8 Hz, 1H), 6.99 (s, 2H), 3.45 (t, J=5.8 Hz, 2H), 3.31-3.25 (m, 2H), 3.19 (dd, J=11.6, 5.8 Hz, 2H), 1.64-1.50 (m, 8H), 1.34 (m, J=14.3, 7.2 Hz, 2H), 0.87 (t, J=7.3 Hz, 3H). 13C NMR (300 MHz, DMSO-d6): δ 221.79, 171.48, 134.93, 57.76, 38.67, 38.33, 37.18, 36.37, 29.95, 25.77, 21.89, 13.88. Measured molecular weight: (m/z)=397.07 m/z (Calculated: 397.08) (M+Na+). FIG. 24 shows an example structure of a maleimide-functionalized RAFT agent (R2) molecule.

FIG. 25 shows a schematic representation of the synthesis of RAFT agent (R2). Precursors R1 (Scheme 1) and N-(2-aminoethyl)-maleimide (Scheme 2) are first synthesized separately and then combined via HATU-mediated coupling to synthesize R2 (Scheme 3).

The following procedures were performed to conjugate R2 to CIS7ferritin. A 100 mL solution was prepared with 4 μM $^{C157}$ferritin, 25 mM HEPES (pH 7.5), and 1 mM of TCEP-HCl. Then 2 mM (final concentration) of R2 (dissolved in dimethylformamide) was added dropwise over 5 min to a vigorously stirring solution. The mixture was stirred for 48 h at room temperature and monitored by ESI-MS. Measured molecular weight: (m/z)=21,445 m/z (Calculated: 21,405).

Graft-from polymerization with free $^{RAFT}$ferritin initiated with VA-044 was performed in the following manner. A 1.5-mL buffered solution containing 50 mM MES (pH 6.5), 1 M sodium acrylate, and 41 μM $^{RAFT}$ferritin was prepared in a 6 mL glass vial with a stir bar and sealed with a septum. The solution was degassed under a N$_2$ atmosphere. 50 μL of a degassed 50 mM stock solution of VA-044 was added, and the polymerization reaction stirred for 24 h at either room temperature or 40° C. After 24 h, a 100-uL aliquot was removed, exposed to air to quench the polymerization, and diluted to 2 mL with water. A control sample was prepared identically, except that the 41 μM $^{RAFT}$ferritin was replaced with 41 μM $^{ΔC}$ferritin and 1 mM R1.

Graft-from polymerization with free $^{RAFT}$ferritin initiated with APS/TEMED was performed as follows. A 300 μL solution containing $^{RAFT}$ferritin (41 μM), APS (1% (w/v)), TEMED (1% (v/v)), and sodium acrylate (1 M) was prepared and stirred for 5 min. Unreacted sodium acrylate, APS, TEMED, and short polymer chains were removed and replaced with water using a 30 kDa MWCO spin concentrator. A control sample was prepared identically, except that the 41 μM RAFT ferritin was replaced with 41 μM $^{AC}$ferritin and 1 mM R1.

For preparation of sodium acrylate-infused ferritin crystals, protein crystals were formed through sitting drop vapor diffusion. The conditions that gave octahedron-or rhombohedron-shaped crystals are detailed in Table 2 shown in FIG. 26. Smaller crystals could also be formed in larger quantities without a reservoir solution. After ferritin crystal formation (which takes 1-2 days), both the well and reservoir solutions were replaced with a solution containing 60 mM $CaCl_2$), 1 M sodium acrylate, and either 25 mM MES (pH 6.5) or 12.5 mM HEPES (pH 8.0). The trigonal ferritin crystals were soaked in a solution consisting of a 1:1 mixture of 2 M sodium acrylate and the reservoir solution. All crystals were soaked for >12 h to ensure complete monomer infusion. FIG. 26 shows example self-assembly conditions for different ferritin crystals according to the disclosed technology.

FIG. 28 shows a flow diagram of an example embodiment of a method 2800 of controllably entrapping a molecular cargo within a material according to the disclosed technology. The method 2800 includes a process 2810 of providing, in an environment containing molecules of the molecular cargo, a reversibly-expandable polymer-integrated crystal (PIX) material, comprising: a crystal comprising a plurality of protein molecules organized in a crystal lattice; and a polymer matrix formed within the crystal lattice of the crystal such that the polymer matrix encompasses molecules from the plurality of protein molecules. The method 2800 further includes a process 2820 of triggering an expansion of the PIX material by applying a first stimulus to the environment to cause the crystal lattice of the PIX material to expand. The method 2800 also includes a process 2830 of loading the molecules of the molecular cargo within the expanded crystal lattice of the PIX material. Furthermore, the method 2800 further includes a process 2840 of entrapping the molecular cargo within the PIX material by triggering a contraction of the PIX material by applying a second stimulus to the environment to cause the crystal lattice of the PIX material to contract with the loaded molecules of the molecular cargo contained within the crystal lattice.

FIG. 29 shows a flow diagram of an example embodiment of a method 2900 of controllably entrapping a charged molecular cargo in a material according to the disclosed technology. The method 2900 includes a process 2910 of providing, in an environment containing charged molecules of the molecular cargo, a polymer-integrated crystal (PIX) material, comprising: a crystal comprising a plurality of protein molecules organized in a crystal lattice; and a polymer matrix formed within the crystal lattice of the crystal such that the polymer matrix encompasses molecules from the plurality of protein molecules. The method 2900 further includes a process 2920 of keeping the PIX material in the environment for an amount of time without expanding the crystal lattice of the crystal of the PIX material. The method 2900 also includes a process 2930 of removing, without expanding the crystal lattice of the crystal of the PIX material, the PIX material from the environment immediately after said keeping the PIX material in the environment for the amount of time.

For monitoring of the expansion and contraction of PIX with light microscopy, single crystals were transferred with a mounted CryoLoop onto a glass slide with a microscopic ruler (OMAX). All images and videos were obtained on an SZX7 (Olympus) microscope equipped with an Infinity 1 CCD (Lumenera). A 10-μL solution containing 4 M NaCl, 1% (w/v) APS, and 1% (v/v) TEMED was added to the crystal. After 5 min of polymerization, the crystal was removed with a Cryoloop and placed on a clean glass slide. Water (10 μL) was added to the crystal to initiate the expansion of the PIX. The expansion was monitored for 5 to 20 min, depending on the sample. To initiate contraction, 10 μL of either 4 M NaCl or 1 M $CaCl_2$) was carefully injected into the solution containing the crystal. Reversible expansion-contraction could be repeated if NaCl was used to induce crystal contraction. Crystal size was determined by measuring the edge length of a facet relative to the microscopic ruler using the Fiji image processing package.

Polymerization of sodium acrylate-infused ferritin crystals initiated with VA-044 was performed in the following manner. After soaking the ferritin crystals in the sodium acrylate solution (as described above), the well and reservoir were replaced with a solution containing 4 M NaCl, 0.2% (w/v) VA-044, and 25 mM MES (pH 6.5). The tray was transferred into an anaerobic tent. After 48 h the crystal trays were removed and exposed to an aerobic environment to quench polymerization and expansion/contraction was monitored as described above.

During monitoring of pyranine fluorescence during in-crystallo polymerization, both cubic and rhombohedral $^{RAFT}$ferritin crystals were soaked in the 1 M sodium acrylate solution supplemented with 10 mM (0.5%) pyranine (Sigma-Aldrich). After 24 h, one single crystal was transferred onto a glass slide, and polymerization was initiated by adding 30 μL of 1% (w/v) APS, and 1% (v/v) TEMED in 4 M NaCl. Hydrogel polymerization throughout the crystal and the corresponding decrease of pyranine fluorescence was monitored with a 10× air objective on the confocal microscope as described above, using a filter to collect light at 500-550 nm (green channel). DIC and fluorescence (488 nm excitation) images were captured at 2-s intervals with 100-ms (DIC) and 100-ms (fluorescence) exposures.

To assess in-crystallo graft-from polymerization initiated with VA-044, cubic and rhombohedral ferritin crystals were prepared in 24-well culture plates without a reservoir solution. After two days, the crystals were harvested and collected into 1.5 mL Eppendorf tubes. The resulting supernatant was discarded, and 200 μL of the sodium acrylate solution (described above) was added. After soaking for >12 h, small portions of the crystal pellet (~7 μL each) were aliquoted into 0.65 mL Eppendorf tubes and transferred into an anaerobic tent. 75 μL of a solution containing 60 mM $CaCl_2$, 0.2% (w/v) VA-044, and 25 mM MES (pH 6.5) was added to each tube to initiate polymerization. The tubes were placed on a heat block at 40° C. Each sample was taken out of the tent and exposed to air at predetermined timepoints. The contents of each tube were transferred into a well of a 24-well culture plate. A 200 μL solution containing 25 mM EDTA (pH 7.0) was added into each well to dissolve the crystals. The plate was placed on a gel rocker >12 h.

To assess in crystallo graft-from polymerization initiated with APS/TEMED, ferritin crystals were prepared and transferred into a sodium acrylate solution, as described above. These crystals were then incubated with a 200 pL solution containing 4 M NaCl, 1% (w/v) APS, and 1% (v/v) TEMED. After 5 min, the crystals were pelleted, and the supernatant was discarded.

Expansion of PIX was monitored using SAXS as follows. Both cubic and rhombohedral $^{RAFT}$ferritin crystals were prepared and transferred into the sodium acrylate solution as described above. After soaking for 24 h, multiple crystals (n>100) were transferred to an Eppendorf tube. The crystals settled to the bottom overnight and were transferred, along with 50 μL of sodium acrylate solution, into 1.5-mm quartz capillaries (Hampton). The capillaries were sealed with modeling clay. The $^{RAFT}$ferritin crystals in capillaries were analyzed at beamline 4-2 of the Stanford Synchrotron Radiation Lightsource (SLAC National Accelerator Laboratory). Data were collected using collimated X-ray radiation (1.127 Å, 11 keV) calibrated with a silver behenate standard. Polymerization was initiated in-situ by the X-ray irradiation (1.5 s exposure), and images were collected every 6 s for up to 20 min. It is important to note that in this procedure, "polymerized" crystals immediately began expanding upon the commencement of data collection. SAXS measurements and polymerization occurred concomitantly. Scattered radiation was detected using a Rayonix225HE detector, and one-dimensional scattering data were obtained through azimuthal averaging of the two-dimensional data to produce plots of the scattering intensity as a function of the scattering vector length, $q=4\pi \sin(\theta)/\lambda$, where $\theta$ is one-half of the scattering angle and $\lambda$ is the wavelength of the X-rays used. Analysis of the one-dimensional data was performed using the powder diffraction processing software JADE (MDI).

For single-crystal X-ray diffraction of ferritin crystals at 100K, crystals were prepared and imaged using light microscopy, as described above. Single-crystal XRD data for the cubic, rhombohedral, and trigonal ferritin crystals were collected at 100 K at beamline 12-2 of SSRL, beamline 502 of ALS, and beamline 9-2 of SSRL. The data were integrated using iMosflm and scaled with Aimless. The structures for cubic, rhombohedral, acrylate-infused rhombohedral, and acrylate-infused trigonal ferritin crystals were determined at resolutions 1.25 Å, 2.27 Å, 2.22 Å, and 2.70 Å, respectively. Molecular replacement was performed with Phaser using the ferritin structure (PDB ID, 6B8F) as a search model. Rigid-body, positional, thermal, TLS, and atomoccupancy refinements were carried out using Phenix. Coot was used for iterative manual model building. All figures were produced with Pymol or ChimeraX.

Single-crystal X-ray diffraction of $^{RAFT}$ferritin crystals at 298K was performed in the following manner. $^{RAFT}$ferritin crystals were prepared as described above. A single crystal (>100 μm) was harvested using a mounted CryoLoop and transferred into a 0.1 mm special glass capillary (Hampton) loaded with 20 μL of the reservoir solution. The diameter of the capillary was smaller than the width of the selected crystal. The bottom ⅓ of the crystal loaded capillary was removed, and mild centrifugal force was applied to trap the crystal between the walls of the capillary. The ends of the capillary were sealed with clay, and the capillary was mounted onto an APEX II CCD diffractometer (Bruker) with Cu Kα radiation (1.5418 Å). Images were analyzed with the Apex III software (Bruker).

Indexing of the crystal facets for rhombohedral and trigonal ferritin crystals was done as follows. Rhombohedral and trigonal ferritin crystals were harvested with a mounted CryoLoop, cryoprotected with perfluoropolyether, and mounted onto an APEX II CCD diffractometer (Bruker) with Cu Kα radiation (1.5418 Å). Three sets of three images (30 s exposures, 1° ϕ rotation per image) were collected at starting at three different ϕ positions (0°, 60°, and 120°). Additionally, a 360° video was captured. The orientation matrix was determined through the XRD images and mapped onto the crystal facets using the Apex III software (Bruker).

An aspect of the disclosed embodiments relates to a reversibly-expandable polymer-integrated crystals (PIX) material for controllably encapsulating and releasing a molecular cargo, comprising: a crystal comprising a plurality of protein molecules organized in a crystal lattice; and a polymer matrix formed within and around the plurality of protein molecules in the crystal lattice of the crystal, wherein the polymer matrix is configured to cause the crystal lattice to expand and contract based on an applied external stimuli, such that the PIX material is operable to controllably entrap and controllably release a molecular cargo, wherein the PIX material is operable to capture the molecular cargo by loading the molecular cargo within the PIX material when the crystal lattice is expanded and entrapping the molecular cargo within the PIX material when the crystal lattice is contracted with the loaded molecular cargo contained within the polymer matrix, and wherein the PIX material is operable to release the molecular cargo by re-expanding the crystal lattice after contraction with the entrapped molecular cargo released therefrom.

In some example embodiments, applied external stimuli includes a lowered ionic strength or a change in pH in an external environment of the PIX material. According to some example embodiments, the crystal is formed by soaking the plurality of protein molecules in a polymer precursor to form the polymer matrix. In an example embodiment, the polymer precursor includes acrylic acid or acrylamide. In some example embodiments, the plurality of protein molecules includes ferritin. According to an example embodiment, the polymer matrix includes a hydrogel. In an example embodiment, the molecular cargo includes a protein, DNA, RNA, nanoparticle, or another large biological or nonbiological molecular entity.

Another aspect of the disclosed embodiments relates to a method for controllably entrapping and/or releasing molecular cargo, comprising: providing the reversibly-expandable polymer-integrated crystals (PIX) material as described in this patent disclosure, in an environment containing molecules; triggering an expansion of the material structure of the PIX material by applying a stimuli to the environment to cause the crystal lattice to expand; loading one or more molecular cargo within the expanded crystal lattice of the PIX material; and entrapping the molecular cargo within the PIX material by triggering a contraction of the material structure of the PIX material by applying a second stimuli to the environment to cause the crystal lattice to contract with the loaded one or more molecular cargo contained within the polymer matrix of the PIX material.

In some example embodiments, the method for controllably entrapping and/or releasing molecular cargo further comprises: triggering the expansion of the material structure of the PIX material by applying the stimuli to the environment to cause the crystal lattice to re-expand; and releasing the one or more molecular cargo from the expanded crystal lattice of the PIX material outside of the PIX material. In an example embodiment, the method further comprises triggering the contraction of the material structure of the PIX material by applying the second stimuli to the environment to cause the crystal lattice to re-contract. According to some example embodiments, the applied stimuli and/or applied second stimuli includes one or more of (i) a change an ionic strength of the environment; (ii) a change in pH of the environment; (iii) an addition of an organic solvent or detergent to the environment; (iv) an addition of a metal chelating agent to the environment; and/or (v) a change in temperature of the environment. In some example embodiments, the molecular cargo includes a large molecular entity including a protein, DNA, RNA, nanoparticle, or another large biological or nonbiological molecular entity.

Yet another aspect of the disclosed embodiments relates to a method for controllably entrapping a small, charged molecular cargo, comprising: providing the reversibly-expandable polymer-integrated crystals (PIX) material as described in this patent disclosure, in an environment containing small, charged molecules; attracting a small, charged molecule having a first net surface charge of positive or negative by charge interaction of a second charge exhibited by the polymer matrix of the PIX material, wherein the second charge is opposite that of the first net surface charge of the small molecule.

In some example embodiments, the small, charged molecular cargo includes lysozyme.

An aspect of the disclosed embodiments relates to a reversibly-expandable polymer-integrated crystal (PIX) material for controllably entrapping and releasing a molecular cargo, comprising: a crystal comprising a plurality of protein molecules organized in a crystal lattice; and a polymer matrix formed within the crystal lattice of the crystal such that the polymer matrix encompasses molecules from the plurality of protein molecules, wherein the polymer matrix is configured to cause the crystal lattice to expand in response to a first stimulus and configured to cause the crystal lattice to contract, when the crystal lattice is expanded, in response to a second stimulus which is different from the first stimulus, wherein the PIX material is operable to capture the molecular cargo by loading the molecules of the molecular cargo within the crystal lattice of the PIX material when the crystal lattice is expanded and is operable to entrap the molecules of the molecular cargo within the PIX material by contracting the crystal lattice with the loaded molecules of the molecular cargo contained within the crystal lattice, and wherein the PIX material is operable to release the molecules of the molecular cargo, comprising re-expanding the crystal lattice after entrapment of the molecules of the molecular cargo within the PIX material.

In some example embodiments, said loading the molecules of the molecular cargo within the crystal lattice of the PIX material when the crystal lattice is expanded comprises allowing the molecules of the molecular cargo to permeate the polymer matrix of the PIX material from an environment outside the PIX material. According to some example embodiments, the polymer matrix includes a hydrogel. In an example embodiment, the hydrogel is a polyacrylate hydrogel. In some example embodiments, the plurality of protein molecules includes ferritin molecules. According to an example embodiment, the ferritin molecules are conjugated with a reversible addition-fragmentation chain-transfer (RAFT) agent. In an example embodiment, the RAFT agent is a maleimide-functionalized trithiocarbonate RAFT agent. According to some example embodiments, the RAFT agent is a cysteine-specific RAFT agent. In some example embodiments, each molecule from the ferritin molecules includes a single set of surface-exposed cysteine residues at positions 157 flanking the ferritin C4 symmetry axes. According to some example embodiments, the crystal is an isotropic crystal. In certain example embodiments, the crystal has a cubic symmetry. In another example embodiment, the crystal is an anisotropic crystal. According to an example embodiment, the crystal has a rhombohedral or a trigonal symmetry. In some example embodiments, the PIX material is operable to expand anisotropically in response to the first stimulus. According to some example embodiments, the PIX material is operable to reversibly expand in response to the first stimulus by more than 100% in volume. In some example embodiments, the molecular cargo includes a protein, a DNA, an RNA, or a nanoparticle. In an example embodiment, the first stimulus includes one or more of: (i) a change in ionic strength of an environment comprising the PIX material; (ii) a change in a pH of the environment; (iii) an addition of an organic solvent or a detergent to the environment; (iv) an addition of a metal chelating agent to the environment; and/or (v) a change in a temperature of the environment. According to an example embodiment, the second stimulus includes one or more of: (i) a change in ionic strength of an environment comprising the PIX material; (ii) a change in a pH of the environment; (iii) an addition of an organic solvent or a detergent to the environment; (iv) an addition of a metal chelating agent to the environment; and/or (v) a change in a temperature of the environment. In some example embodiments, the crystal is a self-assembled protein crystal.

Another aspect of the disclosed embodiments relates to a method of controllably entrapping a molecular cargo within a material, comprising: providing, in an environment containing molecules of the molecular cargo, a reversibly-expandable polymer-integrated crystal (PIX) material, comprising: a crystal comprising a plurality of protein molecules organized in a crystal lattice; and a polymer matrix formed within the crystal lattice of the crystal such that the polymer matrix encompasses molecules from the plurality of protein molecules; triggering an expansion of the PIX material by applying a first stimulus to the environment to cause the crystal lattice of the PIX material to expand; loading the molecules of the molecular cargo within the expanded crystal lattice of the PIX material; and entrapping the molecular cargo within the PIX material by triggering a contraction of the PIX material by applying a second stimulus to the environment to cause the crystal lattice of the PIX material to contract with the loaded molecules of the molecular cargo contained within the crystal lattice.

In some example embodiments, said loading the molecules of the molecular cargo within the expanded crystal lattice of the PIX material comprises allowing the molecules of the molecular cargo to permeate the polymer matrix of the PIX material from the environment. According to some example embodiments, the method further comprises triggering another expansion of the PIX material by applying the first stimulus to the environment to cause the crystal lattice of the PIX material to re-expand; and releasing the molecules of the molecular cargo from the re-expanded crystal lattice of the PIX material outside of the PIX material. In an example embodiment, said releasing the molecules of the molecular cargo comprises allowing the molecules of the molecular cargo to diffuse from the PIX material into the environment. In some example embodiments, the method further comprises triggering another contraction of the PIX material by applying the second stimuli to the environment to cause the crystal lattice of the PIX material to re-contract. According to some example embodiments, the first stimulus and/or the second stimulus includes one or more of: (i) a change in ionic strength of an environment comprising the PIX material; (ii) a change in a pH of the environment; (iii) an addition of an organic solvent or a detergent to the environment; (iv) an addition of a metal chelating agent to the environment; and/or (v) a change in a temperature of the environment. In some example embodiments, the molecular cargo includes a protein, a DNA, an RNA, or a nanoparticle. In an example embodiment, the second stimulus is different from the first stimulus.

Yet another aspect of the disclosed embodiments relates to a method of controllably entrapping a charged molecular cargo in a material, comprising: providing, in an environment containing charged molecules of the molecular cargo, a polymer-integrated crystal (PIX) material, comprising: a crystal comprising a plurality of protein molecules organized in a crystal lattice; and a polymer matrix formed within the crystal lattice of the crystal such that the polymer matrix encompasses molecules from the plurality of protein molecules, wherein each molecule from the charged molecules has a first electric charge, and wherein the polymer matrix of the PIX material has a second electric charge having a sign opposite to a sign of the first electric charge; keeping the PIX material in the environment for an amount of time without expanding the crystal lattice of the crystal of the PIX material; and removing, without expanding the crystal lattice of the crystal of the PIX material, the PIX embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

---

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic primer

<400> SEQUENCE: 1
ccaacctgcg ttgcatgggt gcacc                                          25

<210> SEQ ID NO 2
<211> LENGTH: 25
<212> TYPE: DNA
<213> ORGANISM: Artificial Sequence
<220> FEATURE:
<223> OTHER INFORMATION: Synthetic primer

<400> SEQUENCE: 2
ggtgcaccca tgcaacgcag gttgg                                          25
```

--- material from the environment immediately after said keeping the PIX material in the environment for the amount of time.

In some example embodiments, the molecular cargo includes a protein, a DNA, an RNA, or a nanoparticle. In an example embodiment, the protein is a lysozyme.

It is intended that the specification, together with the drawings, be considered exemplary only, where exemplary means an example. As used herein, the singular forms "a," "an" and "the" are intended to include the plural forms as well, unless the context clearly indicates otherwise. Additionally, the use of "or" is intended to include "and/or," unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate

What is claimed is:

1. A reversibly-expandable polymer-integrated crystal (PIX) material for controllably entrapping and releasing a molecular cargo, comprising:
    a crystal comprising ferritin molecules organized in a crystal lattice, wherein the ferritin molecules are conjugated with a reversible addition-fragmentation chain-transfer (RAFT) agent; and
    a polymer matrix comprising polyacrylate formed within the crystal lattice of the crystal such that the polymer matrix encompasses the ferritin molecules,
    wherein the polymer matrix is configured to cause the crystal lattice to expand in response to a first stimulus and configured to cause the crystal lattice to contract, when the crystal lattice is expanded, in response to a second stimulus which is different from the first stimulus,
    wherein the PIX material is operable to capture the molecular cargo by loading molecules of the molecular cargo within the crystal lattice of the PIX material when the crystal lattice is expanded and is operable to entrap the molecules of the molecular cargo within the PIX material by contracting the crystal lattice with the loaded molecules of the molecular cargo contained within the crystal lattice, and wherein the PIX material is operable to release the molecules of the molecular cargo, comprising re-expanding the crystal lattice after entrapment of the molecules of the molecular cargo within the PIX material.

2. The PIX material of claim 1, wherein said loading the molecules of the molecular cargo within the crystal lattice of the PIX material when the crystal lattice is expanded comprises allowing the molecules of the molecular cargo to permeate the polymer matrix of the PIX material from an environment outside the PIX material.

3. The PIX material of claim 1, wherein the polymer matrix includes a hydrogel.

4. The PIX material of claim 3, wherein the hydrogel is a polyacrylate hydrogel.

5. The PIX material of claim 1, wherein the RAFT agent is a maleimide-functionalized trithiocarbonate RAFT agent.

6. The PIX material of claim 1, wherein the RAFT agent is a cysteine-specific RAFT agent.

7. The PIX material of claim 6, wherein each molecule from the ferritin molecules includes a single set of surface-exposed cysteine residues at positions 157 flanking the ferritin $C_4$ symmetry axes.

8. The PIX material of claim 1, wherein the crystal is an isotropic crystal.

9. The PIX material of claim 8, wherein the crystal has a cubic symmetry.

10. The PIX material of claim 1, wherein the crystal is an anisotropic crystal.

11. The PIX material of claim 10, wherein the crystal has a rhombohedral or a trigonal symmetry.

12. The PIX material of claim 10, wherein the PIX material is operable to expand anisotropically in response to the first stimulus.

13. The PIX material of claim 1, wherein the PIX material is operable to reversibly expand in response to the first stimulus by more than 100% in volume.

14. The PIX material of claim 1, wherein the molecular cargo includes a protein, a DNA, an RNA, or a nanoparticle.

15. The PIX material of claim 1, wherein the first stimulus includes one or more of: (i) a change in ionic strength of an environment comprising the PIX material; (ii) a change in a pH of the environment; (iii) an addition of an organic solvent or a detergent to the environment; (iv) an addition of a metal chelating agent to the environment; and/or (v) a change in a temperature of the environment.

16. The PIX material of claim 1, wherein the second stimulus includes one or more of: (i) a change in ionic strength of an environment comprising the PIX material; (ii) a change in a pH of the environment; (iii) an addition of an organic solvent or a detergent to the environment; (iv) an addition of a metal chelating agent to the environment; and/or (v) a change in a temperature of the environment.

17. The PIX material of claim 1, wherein the crystal is a self-assembled protein crystal.

18. A method of controllably entrapping a molecular cargo within a material, comprising:

providing a reversibly-expandable polymer-integrated crystal (PIX) material in an environment containing molecules of the molecular cargo that includes a protein, a DNA, an RNA, or a nanoparticle, the reversibly-expandable polymer-integrated crystal (PIX) material, comprising:

a crystal comprising ferritin molecules organized in a crystal lattice, wherein the ferritin molecules are conjugated with a reversible addition-fragmentation chain-transfer (RAFT) agent; and a polymer matrix comprising polyacrylate formed within the crystal lattice of the crystal such that the polymer matrix encompasses the ferritin molecules;

triggering an expansion of the PIX material by applying a first stimulus to the environment to cause the crystal lattice of the PIX material to expand;

loading the molecules of the molecular cargo within the expanded crystal lattice of the PIX material; and entrapping the molecular cargo within the PIX material by triggering a contraction of the PIX material by applying a second stimulus to the environment to cause the crystal lattice of the PIX material to contract with the loaded molecules of the molecular cargo contained within the crystal lattice.

19. The method of claim 18, wherein said loading the molecules of the molecular cargo within the expanded crystal lattice of the PIX material comprises allowing the molecules of the molecular cargo to permeate the polymer matrix of the PIX material from the environment.

20. The method of claim 18, further comprising:

triggering another expansion of the PIX material by applying the first stimulus to the environment to cause the crystal lattice of the PIX material to re-expand; and releasing the molecules of the molecular cargo from the re-expanded crystal lattice of the PIX material outside of the PIX material.

21. The method of claim 20, wherein said releasing the molecules of the molecular cargo comprises allowing the molecules of the molecular cargo to diffuse from the PIX material into the environment.

22. The method of claim 20, further comprising:

triggering another contraction of the PIX material by applying the second stimuli to the environment to cause the crystal lattice of the PIX material to re-contract.

23. The method of claim 18, wherein the first stimulus and/or the second stimulus includes one or more of: (i) a change in ionic strength of an environment comprising the PIX material; (ii) a change in a pH of the environment; (iii) an addition of an organic solvent or a detergent to the environment; (iv) an addition of a metal chelating agent to the environment; and/or (v) a change in a temperature of the environment.

24. The method of claim 18, wherein the second stimulus is different from the first stimulus.

25. A method of controllably entrapping a charged molecular cargo in a material, comprising:

providing a polymer-integrated crystal (PIX) material in an environment containing charged molecules of a molecular cargo that includes a protein, a DNA, an RNA, or a nanoparticle, the polymer-integrated crystal (PIX) material, comprising:

a crystal comprising ferritin molecules organized in a crystal lattice, wherein the ferritin molecules are conjugated with a reversible addition-fragmentation chain-transfer (RAFT) agent; and a polymer matrix comprising polyacrylate formed within the crystal lattice of the crystal such that the polymer matrix encompasses the ferritin molecules, wherein each molecule from the charged molecules has a first electric charge, and wherein the polymer matrix of the PIX material has a second electric charge having a sign opposite to a sign of the first electric charge;

keeping the PIX material in an environment for an amount of time without expanding the crystal lattice of the crystal of the PIX material; and removing, without expanding the crystal lattice of the crystal of the PIX material, the PIX material from the environment immediately after said keeping the PIX material in the environment for the amount of time.

26. The method of claim 25, wherein the protein includes at least one of lysozyme, cytochrome C, green fluorescent protein (GFP), bovine serum albumin (BSA), catalase, or streptavidin.

27. The method of claim 25, wherein the polymer matrix includes a polyacrylate hydrogel.

28. The method of claim 25, wherein the RAFT agent is a maleimide-functionalized trithiocarbonate RAFT agent.

29. The method of claim 18, wherein the polymer matrix includes a polyacrylate hydrogel.

30. The method of claim 18, wherein the RAFT agent is a maleimide-functionalized trithiocarbonate RAFT agent.

* * * * *